United States Patent
Johnson

(10) Patent No.: US 9,185,889 B2
(45) Date of Patent: Nov. 17, 2015

(54) CD4 T-CELLS AND CD8ZETA CELLS INVOLVED IN MAMMALIAN HOST RESPONSE TO EPITHELIAL CELL INFECTIONS AND USES THEREOF

(75) Inventor: Raymond M. Johnson, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 13/579,136

(22) PCT Filed: Feb. 15, 2011

(86) PCT No.: PCT/US2011/024934
§ 371 (c)(1),
(2), (4) Date: Oct. 31, 2012

(87) PCT Pub. No.: WO2011/100761
PCT Pub. Date: Aug. 18, 2011

(65) Prior Publication Data
US 2013/0047274 A1 Feb. 21, 2013

Related U.S. Application Data

(60) Provisional application No. 61/304,578, filed on Feb. 15, 2010, provisional application No. 61/367,110, filed on Jul. 23, 2010, provisional application No. 61/367,115, filed on Jul. 23, 2010.

(51) Int. Cl.
| | |
|---|---|
| *C12N 5/00* | (2006.01) |
| *A61K 48/00* | (2006.01) |
| *A01K 67/027* | (2006.01) |
| *C12Q 1/68* | (2006.01) |
| *G01N 33/15* | (2006.01) |
| *G01N 33/53* | (2006.01) |
| *G01N 33/68* | (2006.01) |

(52) U.S. Cl.
CPC ........... *A01K 67/027* (2013.01); *A01K 67/0271* (2013.01); *A01K 67/0276* (2013.01); *C12Q 1/68* (2013.01); *G01N 33/15* (2013.01); *G01N 33/53* (2013.01); *G01N 33/68* (2013.01); *A01K 2207/12* (2013.01); *A01K 2217/075* (2013.01); *A01K 2217/206* (2013.01); *A01K 2227/105* (2013.01); *A01K 2267/0337* (2013.01); *A01K 2267/0387* (2013.01)

(58) Field of Classification Search
CPC ................................ C12Q 1/68; C12Q 1/6837
See application file for complete search history.

(56) References Cited

U.S. PATENT DOCUMENTS

| | | |
|---|---|---|
| 5,850,004 A | 12/1998 | MacMicking et al. |
| 2001/0006950 A1 | 7/2001 | Punnonen et al. |
| 2007/0134261 A1 | 6/2007 | Hancock et al. |

OTHER PUBLICATIONS (Kimchi-Sarfaty et al., 2007, Science, pp. 525-528.*
Kimchi-Sarfaty et al., 2007, Science, pp. 525-528; p. 527.*
Kennell, Progr Nucleic Acid Res. Mol. Biol. 11: 259-301, 1971.*
Stone et al (Immunology, 126(2): 165-176, 2009).*
International Searching Authority, International Search Report for PCT/US2011/024934, issued Dec. 2011.
International Searching Authority, Written Opinion for PCT/US2011/024934, issued Dec. 2011.
International Searching Authority, International Preliminary Report on Patentability for PCT/US2011/024934, issued Aug. 2012.
Igietseme, J. U. et al. Chlamydial Infection in Inducible Nitric Oxide Synthase Knockout Mice. Infection and Immunity Apr. 1998, vol. 66, No. 4, pp. 1282-1286.

\* cited by examiner

*Primary Examiner* — Deborah Crouch
*Assistant Examiner* — Magdalene Sgagias
(74) *Attorney, Agent, or Firm* — Faegre Baker Daniels LLP

(57) ABSTRACT

MHC class II-restricted *Chlamydia*-specific CD4 T cell clones recognize infected upper reproductive tract epithelial cells as early as 12 hours post infection. The timing and degree of T cell activation are dependent on the interferon milieu. Different interferons have different effects on T-cell activation; interferon IFN-β blunts IFN-γ induced up regulation of epithelial cell surface MHC class II and T cell activation. A subset of CD4 T-cells that was especially good at clearing *Chlamydia* infections from the genital tracts of infected mice was found to express the genes Casd1 and Plac8. The mouse Casd1 genes shares some 95 percent identity with the human gene. The differential expression of either Plac8 or Casd1 in COD cells in response to an infection of epithelial tissue provides a ready methodology for the identification of individuals exposed to epithelial infections and a tool for developing vaccines against pathogens that infect epithelial tissue.

23 Claims, 39 Drawing Sheets

FIG. 8

```
                                                 75
SEQ. ID NO.3  human Casd1 extracellular domain    (1) SRRYRGMDSCEYLLSSGRFLGEKVWQPHSCMMHKYKISEAKNCLVDKHIAFIGDSRIRQLFYSFVKIINPQFKE
SEQ. ID NO.4  Mouse Casd1 extracellular domain    (1) -
                                                      SRRYRGMDSCEYLLSSGRFLGEKVWQPHSCMMHKYKISEAKTCLVDKHIAFIGDSRIRQLFYSFVKIINPQFKE
                                                 76
                                                 150
              human Casd1 extracellular domain   (76) EGMKHEMIPFEDKTASVKVDFLWHPEVNGSMKQCIKVWTEDS░░AKPHVIVAGAATWSIKIHNGSSEAL░QYKMMI
              Mouse Casd1 extracellular domain   (75) EGNKHEMIPFEDKAASVKVDFLWHPEVNGSMKQCIKVWTEDS░░LKPHVIVAGAATWSIKIHNGSEEAL░QYKMMI
                                                 151
                                                 225
              human Casd1 extracellular domain  (151) TSIAPLIEKLAKTSDVYWVLQDPYYEDLLSENRKMITNEKIDAYNEAAVSILMSSTRMSKSNVKMFSVSKLIAQE
              Mouse Casd1 extracellular domain  (150) TSIAPLIEKLAKTSDVYWVLQDPYYEDLLSENRKMITNEKIDAYNEAAVSILMSSTRTSKSNMYKMFSVSKLIAQE
                                                 226
                                                 272
              human Casd1 extracellular domain  (226) TIMESIDGLIHIPESSRET░AMILMNVYCNK░░KPVDGSCCQPRPP░T
              Mouse Casd1 extracellular domain  (225) TIMESIDGLIHIPESSRET░AMILMNVYCNK░░KPVDGSCCQPRPP░T
```

FIG. 9

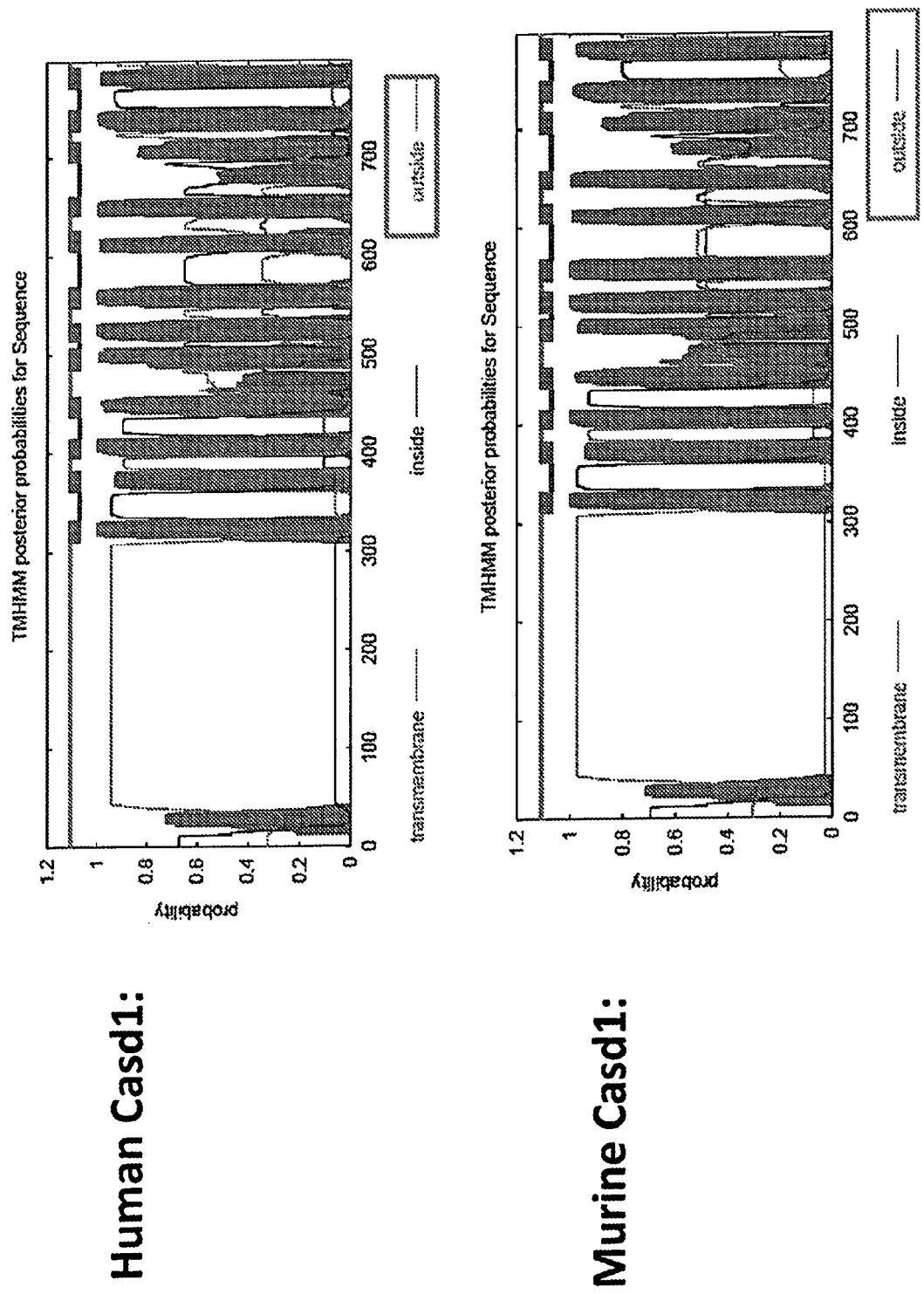

SEQ. ID NO.5 human MQAQMPYVMTQMTQPGVGPGP APQMSMNQIQIGMCDCFSDCGKCLGGTFCFPCL

SEQ. ID NO.6 mouse- MAQMPTVMTQFGFVR---APQMSMNQTSMCDCFSDCGKCLGGTFCFPCL

GCCVALDMMECLCGTCVMRTLYRTLYRTRYGIPSICDDYMATLCCPHCTLC
GCCVALDMMECLCGTTVLMRTLYRTLYRTRYGIPSICDDYMVTLFCPVVSMC

QMKRD INFRRAMRTF
QMKRD IVRPRAMMAF

Homology: Conserved 87%; identity 81.7%

FIG. 11

Reference mRNA sequences translated and compared using Vector NTI 11 Advance 11 software

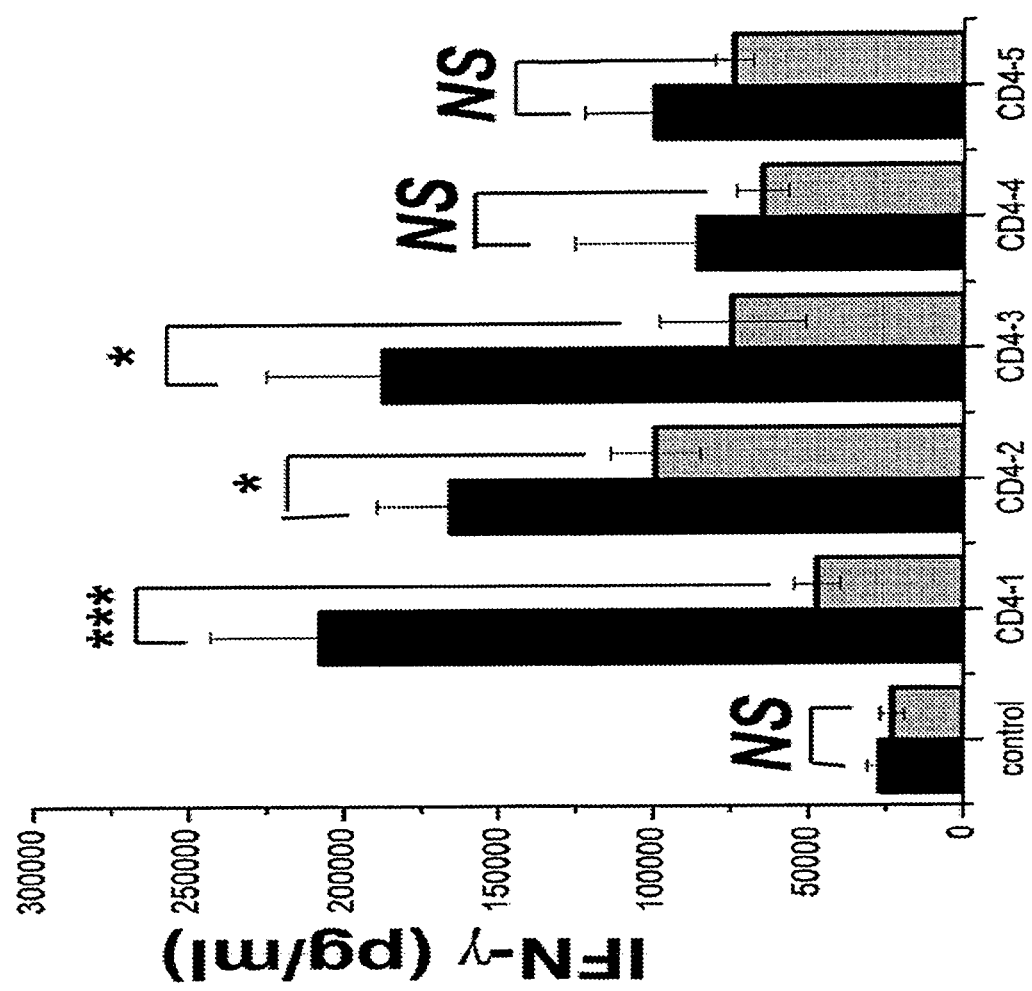

SEQUENCE LISTING

<160> NUMBER OF SEQ ID NOS: 6

<210> SEQ ID NO 1
<211> LENGTH: 675
<212> TYPE: PRT
<213> ORGANISM: Mus musculus

<400> SEQUENCE: 1

```
Met Ala Ala Leu Ala Tyr Asn Leu Gly Lys Arg Glu Ile Asn His Tyr
1               5                   10                  15

Phe Ser Val Arg Ser Ala Lys Val Leu Ala Leu Val Ala Val Leu Leu
            20                  25                  30

Leu Ala Ala Cys His Leu Ala Ser Arg Arg Tyr Arg Gly Asn Asp Ser
        35                  40                  45

Cys Glu Tyr Leu Leu Ser Ser Gly Arg Phe Leu Gly Glu Lys Val Trp
    50                  55                  60

Gln Pro His Ser Cys Met Met His Lys Tyr Lys Ile Ser Glu Ala Lys
65                  70                  75                  80

Thr Cys Leu Val Asp Lys His Ile Ala Phe Ile Gly Asp Ser Arg Ile
                85                  90                  95
```

```
Arg Gln Leu Phe Tyr Ser Phe Val Lys Ile Ile Asn Pro Gln Phe Lys
                100                 105                 110
Glu Glu Gly Asn Lys His Glu Asn Ile Pro Phe Glu Asp Lys Ala Ala
            115                 120                 125
Ser Val Lys Val Asp Phe Leu Trp His Pro Glu Val Asn Gly Ser Met
        130                 135                 140
Lys Gln Cys Ile Lys Val Trp Thr Glu Asp Ser Val Leu Lys Pro His
145                 150                 155                 160
Val Ile Val Ala Gly Ala Thr Trp Ser Ile Lys Ile His Asn Gly
                165                 170                 175
Ser Glu Glu Ala Leu Ala Gln Tyr Lys Met Asn Ile Thr Ser Ile Ala
            180                 185                 190
Pro Leu Leu Glu Lys Leu Ala Lys Thr Ser Asp Val Tyr Trp Val Leu
        195                 200                 205
Gln Asp Pro Val Tyr Glu Asp Leu Leu Ser Glu Asn Arg Lys Met Ile
    210                 215                 220
Thr Asn Glu Lys Ile Asp Ala Tyr Asn Glu Ala Ala Val Ser Ile Leu
225                 230                 235                 240
Asn Ser Ser Thr Arg Thr Ser Lys Ser Asn Val Lys Met Phe Ser Val
                245                 250                 255
Ser Lys Leu Ile Ala Gln Glu Thr Ile Met Glu Ser Leu Asp Gly Leu
            260                 265                 270
His Leu Pro Glu Ser Ser Arg Glu Thr Ser Ala Met Ile Leu Met Asn
        275                 280                 285
Val Tyr Cys Asn Lys Val Val Lys Pro Val Asp Gly Ser Cys Cys Gln
    290                 295                 300
Pro Arg Pro Pro Leu Thr Leu Ile Gln Lys Leu Ala Ala Cys Phe Phe
305                 310                 315                 320
Thr Leu Ser Ile Ile Gly Tyr Phe Ile Phe Tyr Val Ile His Arg Asn
                325                 330                 335
Ala His Arg Lys Asn Lys Pro Cys Thr Asp Leu Glu Ser Gly Glu Glu
            340                 345                 350
Lys Lys Asn Ile Ile Asn Thr Pro Val Ser Ser Leu Glu Ile Leu Leu
        355                 360                 365
Gln Ser Phe Cys Lys Leu Gly Leu Ile Met Ala Tyr Phe Tyr Met Cys
    370                 375                 380
Asp Arg Ala Asn Leu Phe Met Lys Glu Asn Lys Phe Tyr Thr His Ser
385                 390                 395                 400
Ser Phe Phe Ile Pro Ile Ile Tyr Ile Leu Val Leu Gly Val Phe Tyr
                405                 410                 415
Asn Glu Asn Thr Lys Glu Thr Lys Val Leu Asn Arg Glu Gln Thr Asp
            420                 425                 430
Glu Trp Lys Gly Trp Met Gln Leu Val Ile Leu Ile Tyr His Ile Ser
        435                 440                 445
Gly Ala Ser Thr Phe Leu Pro Val Tyr Met His Ile Arg Val Leu Val
    450                 455                 460
Ala Ala Tyr Leu Phe Gln Thr Gly Tyr Gly His Phe Ser Tyr Phe Trp
465                 470                 475                 480
Ile Lys Gly Asp Phe Gly Ile His Arg Val Cys Gln Val Leu Phe Arg
                485                 490                 495
Leu Asn Phe Leu Val Val Val Leu Cys Ile Val Met Asp Arg Pro Tyr
            500                 505                 510
```

```
Gln Phe Tyr Tyr Phe Val Pro Leu Val Thr Val Trp Phe Met Val Ile
    515                 520                 525

Tyr Val Thr Leu Ala Leu Trp Pro Gln Ile Thr Gln Lys Lys Ala Asn
530                 535                 540

Gly Asn Phe Phe Trp Tyr Leu Gly Leu Leu Lys Leu Gly Leu Leu
545                 550                 555                 560

Leu Leu Cys Ile Trp Phe Leu Ala Tyr Ser Gln Gly Ala Phe Glu Lys
            565                 570                 575

Ile Phe Ser Leu Trp Pro Leu Ser Lys Cys Phe Glu Leu Glu Gly Ser
                580                 585                 590

Val Tyr Glu Trp Trp Phe Arg Trp Arg Leu Asp Arg Tyr Val Val Phe
    595                 600                 605

His Gly Val Leu Phe Ala Phe Ile Tyr Leu Ala Leu Gln Arg Arg Gln
    610                 615                 620

Ile Leu Ser Glu Gly Lys Gly Glu Pro Leu Phe Ser Asn Lys Ile Ser
625                 630                 635                 640

Asn Phe Leu Leu Phe Val Ser Val Val Ser Phe Leu Thr Tyr Ser Ile
                645                 650                 655

Trp Ala Ser Ser Cys Lys Asn Lys Ala Glu Cys Asn Glu Leu His Pro
                660                 665                 670

Ser Val Ser
    675

<210> SEQ ID NO 2
<211> LENGTH: 675
<212> TYPE: PRT
<213> ORGANISM: Homo sapiens

<400> SEQUENCE: 2

Met Ala Ala Leu Ala Tyr Asn Leu Gly Lys Arg Glu Ile Asn His Tyr
1               5                   10                  15

Phe Ser Val Arg Ser Ala Lys Val Leu Ala Leu Val Ala Val Leu Leu
                20                  25                  30

Leu Ala Ala Cys His Leu Ala Ser Arg Arg Tyr Arg Gly Asn Asp Ser
            35                  40                  45

Cys Glu Tyr Leu Leu Ser Ser Gly Arg Phe Leu Gly Glu Lys Val Trp
50                  55                  60

Gln Pro His Ser Cys Met Met Lys Tyr Lys Ile Ser Glu Ala Lys
65                  70                  75                  80

Asn Cys Leu Val Asp Lys His Ile Ala Phe Ile Gly Asp Ser Arg Ile
                85                  90                  95

Arg Gln Leu Phe Tyr Ser Phe Val Lys Ile Ile Asn Pro Gln Phe Lys
            100                 105                 110

Glu Glu Gly Asn Lys His Glu Asn Ile Pro Phe Glu Lys Thr Ala
            115                 120                 125

Ser Val Lys Val Asp Phe Leu Trp His Pro Glu Val Asn Gly Ser Met
130                 135                 140

Lys Gln Cys Ile Lys Val Trp Thr Glu Asp Ser Ile Ala Lys Pro His
145                 150                 155                 160

Val Ile Val Ala Gly Ala Thr Trp Ser Ile Lys Ile His Asn Gly
                165                 170                 175

Ser Ser Glu Ala Leu Ser Gln Tyr Lys Met Asn Ile Thr Ser Ile Ala
            180                 185                 190

Pro Leu Leu Glu Lys Leu Ala Lys Thr Ser Asp Val Tyr Trp Val Leu
            195                 200                 205
```

```
Gln Asp Pro Val Tyr Glu Asp Leu Leu Ser Glu Asn Arg Lys Met Ile
    210                 215                 220

Thr Asn Glu Lys Ile Asp Ala Tyr Asn Glu Ala Ala Val Ser Ile Leu
225                 230                 235                 240

Asn Ser Ser Thr Arg Asn Ser Lys Ser Asn Val Lys Met Phe Ser Val
                245                 250                 255

Ser Lys Leu Ile Ala Gln Glu Thr Ile Met Glu Ser Leu Asp Gly Leu
            260                 265                 270

His Leu Pro Glu Ser Ser Arg Glu Thr Thr Ala Met Ile Leu Met Asn
        275                 280                 285

Val Tyr Cys Asn Lys Ile Leu Lys Pro Val Asp Gly Ser Cys Cys Gln
    290                 295                 300

Pro Arg Pro Val Thr Leu Ile Gln Lys Leu Ala Ala Cys Phe Phe
305                 310                 315                 320

Thr Leu Ser Ile Ile Gly Tyr Leu Ile Phe Tyr Ile Ile His Arg Asn
                325                 330                 335

Ala His Arg Lys Asn Lys Pro Cys Thr Asp Leu Glu Ser Gly Glu Glu
            340                 345                 350

Lys Lys Asn Ile Ile Asn Thr Pro Val Ser Ser Leu Glu Ile Leu Leu
        355                 360                 365

Gln Ser Phe Cys Lys Leu Gly Leu Ile Met Ala Tyr Phe Tyr Met Cys
    370                 375                 380

Asp Arg Ala Asn Leu Phe Met Lys Glu Asn Lys Phe Tyr Thr His Ser
385                 390                 395                 400

Ser Phe Phe Ile Pro Ile Ile Tyr Ile Leu Val Leu Gly Val Phe Tyr
                405                 410                 415

Asn Glu Asn Thr Lys Glu Thr Lys Val Leu Asn Arg Glu Gln Thr Asp
            420                 425                 430

Glu Trp Lys Gly Trp Met Gln Leu Val Ile Leu Ile Tyr His Ile Ser
        435                 440                 445

Gly Ala Ser Thr Phe Leu Pro Val Tyr Met His Ile Arg Val Leu Val
    450                 455                 460

Ala Ala Tyr Leu Phe Gln Thr Gly Tyr Gly His Phe Ser Tyr Phe Trp
465                 470                 475                 480

Ile Lys Gly Asp Phe Gly Ile Tyr Arg Val Cys Gln Val Leu Phe Arg
                485                 490                 495

Leu Asn Phe Leu Val Val Val Leu Cys Ile Val Met Asp Arg Pro Tyr
            500                 505                 510

Gln Phe Tyr Tyr Phe Val Pro Leu Val Thr Val Trp Phe Met Val Ile
        515                 520                 525

Tyr Val Thr Leu Ala Leu Trp Pro Gln Ile Ile Gln Lys Lys Ala Asn
    530                 535                 540

Gly Asn Cys Phe Trp His Phe Gly Leu Leu Lys Leu Gly Phe Leu
545                 550                 555                 560

Leu Leu Phe Ile Cys Phe Leu Ala Tyr Ser Gln Gly Ala Phe Glu Lys
                565                 570                 575

Ile Phe Ser Leu Trp Pro Leu Ser Lys Cys Phe Glu Leu Lys Gly Asn
            580                 585                 590

Val Tyr Glu Trp Trp Phe Arg Trp Arg Leu Asp Arg Tyr Val Val Phe
        595                 600                 605

His Gly Met Leu Phe Ala Phe Ile Tyr Leu Ala Leu Gln Lys Arg Gln
    610                 615                 620
```

```
Ile Leu Ser Glu Gly Lys Gly Glu Pro Leu Phe Ser Asn Lys Ile Ser
625                 630                 635                 640

Asn Phe Leu Leu Phe Ile Ser Val Val Ser Phe Leu Thr Tyr Ser Ile
            645                 650                 655

Trp Ala Ser Ser Cys Lys Asn Lys Ala Glu Cys Asn Glu Leu His Pro
            660                 665                 670

Ser Val Ser
        675

<210> SEQ ID NO 3
<211> LENGTH: 271
<212> TYPE: PRT
<213> ORGANISM: Homo sapiens

<400> SEQUENCE: 3

Ser Arg Arg Tyr Arg Gly Asn Asp Ser Cys Glu Tyr Leu Leu Ser Ser
1               5                   10                  15

Gly Arg Phe Leu Gly Glu Lys Val Trp Gln Pro His Ser Cys Met Met
            20                  25                  30

His Lys Tyr Lys Ile Ser Glu Ala Lys Asn Cys Leu Val Asp Lys His
        35                  40                  45

Ile Ala Phe Ile Gly Asp Ser Arg Ile Arg Gln Leu Phe Tyr Ser Phe
50                  55                  60

Val Lys Ile Ile Asn Pro Gln Phe Lys Glu Glu Gly Asn Lys His Glu
65                  70                  75                  80

Asn Ile Pro Phe Glu Asp Lys Thr Ala Ser Val Lys Val Asp Phe Leu
                85                  90                  95

Trp His Pro Glu Val Asn Gly Ser Met Lys Gln Cys Ile Lys Val Trp
            100                 105                 110

Thr Glu Asp Ser Ile Ala Lys Pro His Val Ile Val Ala Gly Ala Ala
        115                 120                 125

Thr Trp Ser Ile Lys Ile His Asn Gly Ser Ser Glu Ala Leu Ser Gln
130                 135                 140

Tyr Lys Met Asn Ile Thr Ser Ile Ala Pro Leu Leu Glu Lys Leu Ala
145                 150                 155                 160

Lys Thr Ser Asp Val Tyr Trp Val Leu Gln Asp Pro Val Tyr Glu Asp
                165                 170                 175

Leu Leu Ser Glu Asn Arg Lys Met Ile Thr Asn Glu Lys Ile Asp Ala
            180                 185                 190

Tyr Asn Glu Ala Ala Val Ser Ile Leu Asn Ser Ser Thr Arg Asn Ser
        195                 200                 205

Lys Ser Asn Val Lys Met Phe Ser Val Ser Lys Leu Ile Ala Gln Glu
210                 215                 220

Thr Ile Met Glu Ser Leu Asp Gly Leu His Leu Pro Glu Ser Ser Arg
225                 230                 235                 240

Glu Thr Thr Ala Met Ile Leu Met Asn Val Tyr Cys Asn Lys Ile Leu
                245                 250                 255

Lys Pro Val Asp Gly Ser Cys Cys Gln Pro Arg Pro Pro Val Thr
            260                 265                 270

<210> SEQ ID NO 4
<211> LENGTH: 271
<212> TYPE: PRT
<213> ORGANISM: Mus musculus
```

-continued

```
<400> SEQUENCE: 4

Ser Arg Arg Tyr Arg Gly Asn Asp Ser Cys Glu Tyr Leu Ser Ser
1               5                   10                  15

Gly Arg Phe Leu Gly Glu Lys Val Trp Gln Pro His Ser Cys Met Met
            20                  25                  30

His Lys Tyr Lys Ile Ser Glu Ala Lys Thr Cys Leu Val Asp Lys His
        35                  40                  45

Ile Ala Phe Ile Gly Asp Ser Arg Ile Arg Gln Leu Phe Tyr Ser Phe
    50                  55                  60

Val Lys Ile Ile Asn Pro Gln Phe Lys Glu Glu Gly Asn Lys His Glu
65                  70                  75                  80

Asn Ile Pro Phe Glu Asp Lys Ala Ala Ser Val Lys Val Asp Phe Leu
                85                  90                  95

Trp His Pro Glu Val Asn Gly Ser Met Lys Gln Cys Ile Lys Val Trp
            100                 105                 110

Thr Glu Asp Ser Val Leu Lys Pro His Val Ile Val Ala Gly Ala Ala
        115                 120                 125

Thr Trp Ser Ile Lys Ile His Asn Gly Ser Glu Glu Ala Leu Ala Gln
    130                 135                 140

Tyr Lys Met Asn Ile Thr Ser Ile Ala Pro Leu Leu Glu Lys Leu Ala
145                 150                 155                 160

Lys Thr Ser Asp Val Tyr Trp Val Leu Gln Asp Pro Val Tyr Glu Asp
                165                 170                 175

Leu Leu Ser Glu Asn Arg Lys Met Ile Thr Asn Glu Lys Ile Asp Ala
            180                 185                 190

Tyr Asn Glu Ala Ala Val Ser Ile Leu Asn Ser Ser Thr Arg Thr Ser
        195                 200                 205

Lys Ser Asn Val Lys Met Phe Ser Val Ser Lys Leu Ile Ala Gln Glu
    210                 215                 220

Thr Ile Met Glu Ser Leu Asp Gly Leu His Leu Pro Glu Ser Ser Arg
225                 230                 235                 240

Glu Thr Ser Ala Met Ile Leu Met Asn Val Tyr Cys Asn Lys Val Val
                245                 250                 255

Lys Pro Val Asp Gly Ser Cys Cys Gln Pro Arg Pro Pro Leu Thr
            260                 265                 270

<210> SEQ ID NO 5
<211> LENGTH: 115
<212> TYPE: PRT
<213> ORGANISM: Homo sapiens

<400> SEQUENCE: 5

Met Gln Ala Gln Ala Pro Val Val Val Thr Gln Pro Gly Val Gly
1               5                   10                  15

Pro Gly Pro Ala Pro Gln Asn Ser Asn Trp Gln Thr Gly Met Cys Asp
            20                  25                  30

Cys Phe Ser Asp Cys Gly Val Cys Leu Cys Gly Thr Phe Cys Phe Pro
        35                  40                  45

Cys Leu Gly Cys Gln Val Ala Asp Met Asn Glu Cys Cys Leu Cys
    50                  55                  60

Gly Thr Ser Val Ala Met Arg Thr Leu Tyr Arg Thr Arg Tyr Gly Ile
65                  70                  75                  80

Pro Gly Ser Ile Cys Asp Asp Tyr Met Ala Thr Leu Cys Cys Pro His
                85                  90                  95
```

```
Cys Thr Leu Cys Gln Ile Lys Arg Asp Ile Asn Arg Arg Ala Met
            100                 105                 110

Arg Thr Phe
        115

<210> SEQ ID NO 6
<211> LENGTH: 112
<212> TYPE: PRT
<213> ORGANISM: Mus musculus

<400> SEQUENCE: 6

Met Ala Gln Ala Pro Thr Val Ile Val Thr Gln Pro Gly Phe Val Arg
1               5                   10                  15

Ala Pro Gln Asn Ser Asn Trp Gln Thr Ser Leu Cys Asp Cys Phe Ser
                20                  25                  30

Asp Cys Gly Val Cys Leu Cys Gly Thr Phe Cys Phe Thr Cys Leu Gly
            35                  40                  45

Cys Gln Val Ala Ala Asp Met Asn Glu Cys Cys Leu Cys Gly Thr Thr
        50                  55                  60

Val Ala Met Arg Thr Leu Tyr Arg Thr Arg Tyr Gly Ile Pro Gly Ser
65                  70                  75                  80

Ile Cys Asp Asp Tyr Met Val Thr Leu Phe Cys Pro Val Cys Ser Val
                85                  90                  95

Cys Gln Leu Lys Arg Asp Ile Asn Arg Arg Arg Ala Met Asn Ala Phe
            100                 105                 110
```

CD4 T-CELLS AND CD8ZETA CELLS INVOLVED IN MAMMALIAN HOST RESPONSE TO EPITHELIAL CELL INFECTIONS AND USES THEREOF

PRIORITY CLAIM

This application is a national stage application of International Application Number PCT/US2011/024934, filed Feb. 15, 2011, titled CD4 T-CELLS INVOLVED IN MAMMALIAN HOST RESPONSE TO EPITHELIAL CELL INFECTION AND USES THEREOF, which claims the benefit of U.S. provisional patent application No. 61/367,115 filed on Feb. 15, 2010, provisional patent application No. 61/367,110 filed Jul. 23, 2010 and provisional application No. 61/304,578 filed May 15, 2010. The disclosure of each application is expressly incorporated herein by reference in its entirety.

STATEMENT OF GOVERNMENTAL RIGHTS

This invention was made with government support under AI070514 awarded by the National Institutes of Health. The Government has certain rights in the invention.

FIELD OF THE INVENTION

Some aspects of the invention relate to identifying a subset of CD4-T cells and components thereof that participate in clearing infections from mammalian epithelial tissue and using the same to screen for vaccines.

BACKGROUND

*Chlamydia trachomatis* is the most common bacterial sexually transmitted infection in the developed world with 2-3 million actively-infected individuals in the U.S. (Prevention, 2007) and similar numbers in Europe (Low, 2004). In women *C. trachomatis* infections can ascend into the upper reproductive tract causing pelvic inflammatory disease and scarring with resulting infertility and ectopic pregnancies. Standard public health measures including provision of antibiotic therapy and partner tracing have not significantly decreased the incidence of *C. trachomatis* infections. There is a general consensus among *Chlamydia* basic scientists and clinicians that development of a *Chlamydia* vaccine is a health care priority.

Unfortunately our understanding of the immunobiology of T cell interactions with *Chlamydia*-infected epithelial cells is limited, and most of the existing studies are limited by the use of epithelial tumors as antigen presenting cells (APC). While tumor cell lines have morphologic features consistent with an epithelial lineage, it is unclear whether their immunobiology remains intact after tumorgenesis and evasion of host immunosurveillance. Understanding cellular immunity at the epithelial interface is critical for developing new vaccine strategies and identifying surrogate markers for vaccine efficacy prior to initiating clinical trials.

Given the huge impact that infections with *Chlamydia* has on human health and the problems with currently available treatments for and vaccinations against this pathogen, there is a pressing need for increased understanding of how the mammalian immune system interacts with this pathogen. Some aspects and embodiments of the invention address these needs.

SUMMARY

Some embodiments include methods for screening for a vaccine and or detecting an immunological response to an antigen, comprising the steps of: providing a mammal, wherein the animal is susceptible to an infectious agent; exposing the animal to a compound, where the compound may provide immunity to the infectious agent; and analyzing a sample recovered from the animal after the exposing step for evidence that the animal expresses a gene with at least 90 percent homology to either or both Casd1 (SEQ ID NO. 1) and/or a gene encoding the protein Plac8 (SEQ ID NO. 5). In some embodiments the gene expressed has at least 90 percent homology to Casd1. In some embodiments the mammal is a human in still other embodiments the mammal is a mouse.

Some aspects include making and using a transgenic mouse, in which some cells in the mice are engineered to express iNOS activity and also to express a plurality of epithelial cells that do not exhibit iNOS activity. During the course of making these mice some of these mice may include an iNOS gene/exon flanked by loxP sites. In some embodiments the mice are homozygous in an iNOS gene/exon flanked by loxP sites.

Some aspects of the invention include a method of making a transgenic mouse that include the step of making a knockin mouse in which the mouse includes a copy of a gene encoding Cre-recombinase under the control of an epithelial-specific promotor; wherein the Cre-recombinase recognizes adjacent loxP sites and excises the DNA residing between the adjacent loxP sites and the expression of said copy of gene encoding Cre-recombinase is under the control of the epithelial-specific promotor. In some embodiments the mice are homozygous in said copy of the gene encoding Cre-recombinase. In some embodiments the mice include a copy of a gene encoding Cre-recombinase, an epithelial-specific promotor and an iNOS gene/exon flanked by loxP site, in which the gene encoding Cre-recombinase is under the control of the epithelial-specific promoter.

Still other aspects include a method for modeling *Chlamydia* infections, comprising the steps of: providing at least one mouse, wherein the mouse includes cells that express iNOS activity and epithelial cells that do not express iNOS activity, supplying a pathologic species of *Chlamydia* and contacting the mouse with a pathologic species of *Chlamydia*. In some embodiments the method for modeling *Chlamydia* in mice also includes the step of: observing the progression of *Chlamydia* infection in a mouse after the mouse is placed in contact with a pathologic species of *Chlamydia*. In some embodiments the strain of *Chlamydia* used to infect the mice is a strain normally found to infect humans. Still other embodiments include the steps of: treating a mouse with at least one compound that is intended to interfere with the ability of at least one species of *Chlamydia* to infect mice or humans. In some embodiments the mice are observed after treating or vaccinating them with at least one compound intended to interfere with an infection caused by *Chlamydia* for evidence that the compound effects the progression and/or development of the infection.

Some embodiments of the invention include methods of identifying an agent that elicits an immune response in the epithelial tissue of a mammal. These methods may comprise the steps of providing a mammal which is susceptible to an infection of its epithelial tissue. Exposing the mammal to an agent, for example a putative antigen, which may elicit an immune response and then analyzing a sample from the mammals epithelial tissue for evidence of either or both CD8zeta cells or a types of CD4 T-cells that expresses a Casd1 and/or Plac 8. In some embodiments the mammal is either a mouse or a human. In some embodiments the samples are assayed for evidence of an immune response predominately localized to the epithelial layer by assaying multiple samples from the same animal. In some embodiments the method being with a naïve animal. Multiple sampling usually includes taking at least one sample before exposure to the agent and at least one sample after exposure to the agent.

In some embodiments evidence that the mammal has mounted an epithelial tissue based immune response is evidence that Casd1 or its equivalent gene was expressed in response to contacting the agent with the mammal. Evidence of such a response includes, but is not limited to, the presence in the sample of at least one of the polypeptides selected from the group consisting of: SEQ ID NO. 1, SEQ ID NO. 2, SEQ ID NO. 3, SEQ ID NO. 4, SEQ ID NO. 5, SEQ ID NO. 6, or at least one unique sequence of amino acids from at least one of them.

Method for identifying such cells include, but are not limited to: using flow cytometry to search for CD4 T-cells that express Casd1 and/or Plac8; measuring the level of at least one mRNA that encodes at least one unique portion of either Casd1 and/or Plac 8 using of a micro array chip wherein said chip includes at least one portion that interacts with a gene product of Casd1 and/or Plac8; contacting the sample with at least antibody that binds to at least one portion of a polypeptide selected from the group consisting of: SEQ ID NO. 1, SEQ ID NO. 2, SEQ ID NO. 3, SEQ ID NO. 4, SEQ ID NO. 5, SEQ ID NO. 6 and real time PCR. In some embodiments the antibodies are labeled for ready detection. In some embodiments the antibodies are used in Western blots or another form of antibody based identification.

In some embodiments the gene expressed in CD4 t-cells found in the epithelial tissue of animal exposed to an epithelial pathogen expressed has at least 80 percent homology to either human or murine Casd 1. In some embodiments the cells may also express a gene that has at least 80 percent homology to Plac8. In still other embodiments the genes expressed in the mammal in response to the agent and which are evidence of epithelial tissue based immune response have upwards of 85 or 90 or 95 percent homology to at least one of the following genes, Casd1 or Plac8.

In some embodiments the mammal used to identify an agent that elicits an epithelial tissue based immune response is a transgenic mouse in which the mouse is genetically altered such that the cells in its epithelial tissue of the transgenic mouse do not exhibit iNOS activity while cells in other portions of the transgenic mouse's body may exhibit iNOS activity.

In some embodiments the agent used to elicit the immune response in the animal is intended to elicit a response to at least one microorganism that infects the epithelial cell layer of a mammal. Such organisms include, but are not limited to, bacteria such as *Chlamydia*. In some embodiments the agents tested are antigens to either or both *C. muridarum* and *C. trachomatis*.

Still other embodiments of the invention include kits for identifying an agent that elicits an immune response in mammalian epithelial tissue. These kits may comprise at least one reagent that preferentially interacts with CD8zeta cells of a subset of CD4 T-cells that express Casd1 and/or Plac8 genes or homologous genes thereof and that are found in the epithelial tissue of mammals. In some embodiments the kits may include an antibody that binds to at least one portion of at least one amino acid sequence selected from the group consisting of: SEQ ID NO. 1, SEQ ID NO. 2, SEQ ID NO. 3, SEQ ID NO. 4, SEQ ID NO. 5, SEQ ID NO. 6. In some embodiments the antibodies may be labelled for ready detection. Some kits may further include additional reagents such as a second labelled antibody that binds to the first antibody.

In some embodiments the kits comprise at least one reagent which is a portion of a nucleic acid that hybridizes to a portion of the mRNA produced by the expression of Casd1 and/or Plac8. In some embodiments the nucleic acid may be attached to a surface such as chip, bead, well plate and the like.

Still other embodiments of the invention include transgenic animals, comprising, for example a transgenic mouse, in which the transgenic mouse is genetically altered such that the epithelial cells of the transgenic mouse does not express iNOS, while tissue in the remainder of the animal may still express iNOS activity. In some transgenic animals the epithelial cells that do not express iNOS include epithelial issue located in the upper reproductive tract of the transgenic mouse.

In some the transgenic mice the epithelial cells comprising the epithelial tissue in the upper reproductive tract lack an iNOS gene. In still other embodiments the cells of the epithelial layer may express an iRNA that selectively interferes with the translation of the proteins of the iNOS system in the epithelial layer.

Some embodiments of the invention include methods of making transgenic animals that are better models for how diseases such as *Chlamydia* infect, progress and respond to treatments and vaccinations in humans than are wild type animals and many commercially available transgenic animal modes. In some embodiments the animals, for example transgenic mice, are made by a process comprising the steps of: providing a first mouse, said first mouse being homozygous for an iNOS allele, wherein said iNOS allele comprises an iNOS gene flanked by loxP sites; supplying a second mouse, said second being homozygous or heterologous for a Cre-recombinase gene under the control of an epithelial-specific promoter; crossing said first mouse with said second mouse, wherein said step of crossing produces a plurality of first progeny mice; crossing at least two first progeny mice with each other; and selecting for a second progeny mouse homozygous for the iNOS allele comprising an iNOS gene flanked by loxP sites and having at least one allele comprising the Cre-recombinase gene under the control of an epithelial-specific promoter. These methods of maintaining a transgenic animal colony may further include the step of crossing a first mouse (homozygous iNOS flanked by loxP) with said second progeny mice including at least one allele comprising the Cre-recombinase gene under the control of an epithelial-specific promoter, producing a third progeny, wherein 100% of said third progeny mice inheriting an allele with Cre-recombinase gene under the control of an epithelial-specific promoter will be iNOS negative in the epithelial cells including its reproductive tract.

SUMMARY OF SEQUENCE DATA

SEQ ID NO. 1 Murine Casd1 amino acid sequence.
SEQ ID NO. 2 Human Casd1 amino acid sequence.
SEQ ID NO. 3 Human Casd1 extracellular domain amino acid sequence.
SEQ ID NO. 4 Murine Casd1 extracellular domain amino acid sequence.
SEQ ID NO. 5 A portion of human Plac8 amino acid sequence.
SEQ ID NO. 6 A portion of mouse Plac8 amino acid sequence.

BRIEF DESCRIPTION OF THE FIGURES

FIG. 8. A comparison of the entire Casd1 amino acid sequences from mice (SEQ ID. No. 1) and from humans (SEQ ID. No. 2). About 97.2% of the amino acids are conserved and about 94.5% of the amino acids are identical.

FIG. 9. Comparison of the TMHMM predicted Extracellular domain of the Casd1 human (SEQ ID. No. 3) and mouse (SEQ ID. No. 4).

FIG. 10. Results of an analysis of the likely structure of the protein expressed by the Casd1 gene: upper panel, human; lower panel, mouse.

FIG. 11. Comparison of the Plac8 amino-acid sequence human (SEQ ID. No. 5) and mouse (SEQ ID. No. 6).

FIG. 16A. Graph of IFN-γ (pg ml$^{-1}$) produced by different CD4 T-cell clones co-cultured with ultraviolet-light-inactivated *C. muridarum* pulsed syngeneic C57BL/6J (H-2 IA$^b$; black bars) or bm12 (H-2 IA$^{bm12}$; gray bars) irradiated splenocytes.

DESCRIPTION

Figure 1A:
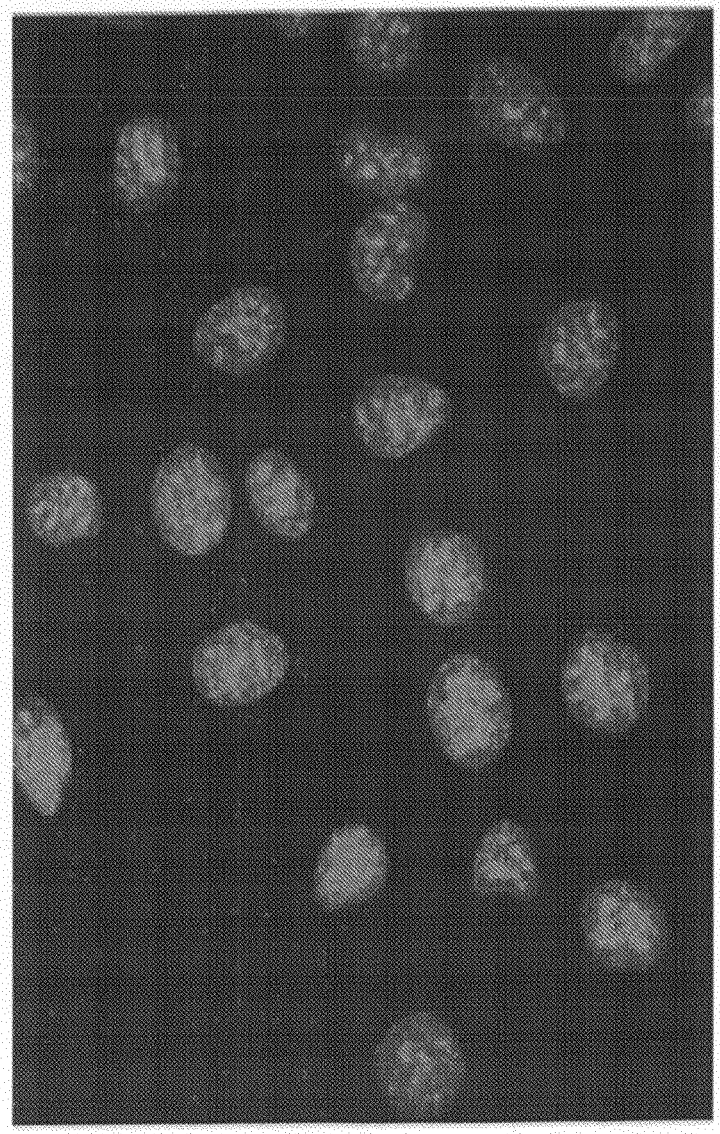
FIG. 1A. Characterization of oviduct epithelial cell line C57epi.1 ($H-2K^b$). A) Control stained with an irrelevant antibody specific for $H-2K^k$. Nuclei visualized with DAPI counter stain.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates is within the scope of this invention.

Histopathology studies show that *C. trachomatis* replicates predominantly in the reproductive tract epithelium during natural human infections (Kiviat, et al., 1986; Swanson, et al., 1975) and experimental murine *C. muridarum* infections (Morrison and Caldwell, 2002). Inclusions are not seen in other cell types even though *Chlamydia* can undergo limited replication in macrophages and dendritic cells (Steele, et al., 2004). It is unlikely that replication in non-epithelial cell lineages makes a major contribution to genital tract shedding. The mouse model for *Chlamydia* genital tract infections supports a critical role for CD4 T cells in protective immunity as mice deficient in MHC class II cannot control *C. muridarum* genital tract infections (Morrison, et al., 1995), and CD4 T cell depletion is detrimental to resolution of primary genital tract infections (Morrison and Morrison, 2005). Because *C. muridarum* replicates in epithelial cells lining the reproductive tract, the most straightforward mechanism for clearing the genital tract would involve *Chlamydia*-specific CD4 T cell interactions with infected epithelial cells. However in the absence of any data supporting this specific interaction, other indirect mechanisms based on CD4 T cell production of IFN-γ and provision of help to B cells and CD8 T cells have been proposed as the mechanism for clearance (Roan and Starnback, 2008).

*C. muridarum*-specific CD4 T cell lines protective in adoptive transfer studies were shown to control *C. muridarum* replication in polarized epithelial monolayers (Igietseme, et al., 1994). The mechanism of control was dependent on IFN-γ and physical interaction of T cells with the infected epithelial cells via LFA-1. In the presence of IFN-γ, T cell engagement of epithelial cells via LFA-1 was shown to augment epithelial nitric oxide production above that induced by IFN-γ alone, and nitric oxide was shown to be the effector molecule responsible for controlling *Chlamydia* replication (Igietseme, et al., 1996). This anti-*Chlamydia* effector mechanism did not require that the CD4 T cell clone recognize the infected epithelial monolayer in an antigen-specific fashion, as the same pre-activated CD4 T cell clone controlled *C. psittaci* replication in polarized epithelial monolayers even though it does not recognize a *C. psittaci* antigen.

Epithelial cells are semiprofessional antigen presenting cells and, in their unperturbed state, likely play a role in immunotolerance at mucosal surfaces (Marelli-Berg and Lechler, 1999). However in inflammatory environments, such as transplant rejection and graft-versus-host-disease, epithelial cells change their immunophenotype including up regulation of MHC class II (Copin, et al., 1995; Nakhleh, et al., 1989). In trachoma, an eye infection caused by *Chlamydia trachomatis* serovars A-C, conjunctival epithelial cells from human clinical specimens had upregulated cell surface MHC class II and were presumably competent to present antigens to CD4 T cells (el-Asrar, et al., Br. J. Ophthalmol, 73:276-282; 73:399-400, 2005). In vitro studies have shown that rat and murine uterine epithelial cells process and present exogenous ovalbumin to OVA-specific CD4 T cells (Prabhala and Wira, 1995; Wira, et al., 2005). However in vitro processing and presentation of concentrated extracellular ovalbumin to CD4 T cells by uterine epithelial cells does not directly address whether *Chlamydia* antigens sequestered in membrane-bound inclusions get processed and presented to *Chlamydia*-specific CD4 T cells in vivo. The mechanics of CD4 T cell contributions to resolution of genital tract infections remain unclear.

As reported herein, an epithelial cell line from the upper reproductive tract of a female C57BL/6 mouse, and a panel of ten *Chlamydia*-specific CD4 T cell clones from immune C57BL/6 mice that previously self-cleared *C. muridarum* genital tract infections was derived. These reagents allowed for the direct investigation of a) whether *Chlamydia*-specific CD4 T cells can recognize *C. muridarum* infected reproductive tract epithelial cells, b) when during the time course of infection recognition occurs, and c) the role of interferons in modulating epithelial interactions with CD4 T cells. Discussed herein are the results of these investigations.

Derivation of biologically intact upper reproductive tract epithelial cell lines and *Chlamydia*-specific CD4 T cell clones from mice that self-cleared primary *C. muridarum* genital tract infections gave us the opportunity to investigate basic *Chlamydia* pathogenesis questions related to CD4 T cell interactions with infected epithelial cells. The first question addressed was whether *Chlamydia*-specific CD4 T cells could recognize infected reproductive tract epithelial cells. Compared with professional antigen presenting cells, epithelial cells express low levels of MHC class II, lack critical costimulatory molecules, and lack an obvious antigen presentation pathway for *Chlamydia* antigens. There have been doubts about whether CD4 T cells directly mediate clearance through interactions with infected reproductive tract epithelial cells (Roan and Starnbach, 2008), though depletion studies show a dominant role for CD4 T cells in primary infection (Morrison and Morrison, 2005) and knockout mice show an absolute dependence on MHC class II for clearance of *C. muridarum* from the genital tract (Morrison, et al., 1995). Data presented here clearly show that *Chlamydia*-specific CD4 T cells can recognize infected epithelial cells in antigen-specific fashion, including engagement of the CD4 co-receptor by epithelial MHC class II molecules.

The timing of *Chlamydia*-specific CD4 T cell recognition of infected epithelial cells over the course of infection was investigated. When T cells recognize infected targets is an important mechanistic consideration as delayed recognition narrows the window for an effector mechanism to act before non-infectious reticulate bodies transition to infectious elementary bodies. This investigation shows that CD4 T cell recognition of infected epithelial cells occurred roughly 12-18 h post-infection, and that recognition was influenced by type 1 and 2 interferons. This window of time is relatively late during the replication cycle of *C. muridarum* in oviduct epithelial cells (Nelson, et al., 2005), but is theoretically early enough to allow T cell-mediated disruption of replication by either disabling the epithelial host cell (incubator) or by directly attacking the inclusion, for example by production of nitric oxide (Igietseme, et al., 1996).

The ability of the CD4 T cell clones disclosed herein was stringently tested to determine if they could control *Chlamy-* dia replication in vitro by using them at an effector to target ratio of <1 in flat bottom tissue culture plates, which provide an additional surface area challenge for physically small lymphocytes. Eight of the ten CD4 T cell clones controlled replication of *C. muridarum* in the oviduct epithelial cell line even though T cell activation by infected epithelial cells was clearly sub-maximal as reflected by lower IFN-γ production (50-100-fold) and lack of proliferation compared with activation by antigen-pulsed irradiated splenocytes. Interestingly the CD4 T cells that could control replication in vitro had two phenotypes. On set of CD4 clones (uvmo-1,-2,-3) was able to control *C. muridarum* replication with or without IFN-γ pretreatment of epithelial cells; the other set (LN4-10,-12,-13, Sp14-10,-11) was dependent on IFN-γ pre-treatment of the epithelial cells prior to infection. An hypothesis consistent with these results is that the existence of *Chlamydia*-specific CD4 T cell clones that can control *C. muridarum* without exogenous IFN-γ pretreatment of epithelial cells provides an explanation for the near normal clearance kinetics of 99.9% *C. muridarum* from the genital tract of IFN-γ knockout mice (Cotter, et al., 1997; Perry, et al., 1997). Also consistent with these results is that this IFN-γ independent subset of CD4 T cells recognizes *Chlamydia* antigens that are efficiently processed, making it to the cell surface bound to MHC class II molecules at very low levels of MHC class II expression. Alternatively, this T cell subset may have high affinity TCRs that allow activation with relatively few antigen-MHC complexes on the epithelial cell surface. While it is not possible or necessary to draw conclusions based on the limited numbers of T cell clones from each derivation strategy, it is interesting that the three most effective CD4 clones came from a culture system in which the APC was a naïve splenocyte pulsed with U.V.-inactivated *C. muridarum*. Because the inoculum was low, ~2.5 IFU per naïve splenocyte, this suggests either very efficient processing of select *C. muridarum* antigens, or a bias of the culture system toward selection of T cells with high affinity TCR. Either scenario suggests that development of a successful subunit vaccine could depend on choosing specific *Chlamydia* antigen(s).

The geographic source of the *Chlamydia*-specific CD4 T cell clones did not appear to be predictive of their ability to control in vitro replication of *C. muridarum* in epithelial cells. The most effective and least effective CD4 T cell clones came from the spleens of immune mice. CD4 clones derived from lymph nodes draining the reproductive tract were not more effective that those from splenocytes. The finding that *Chlamydia*-specific CD4 T cells (ummo-4 & LN4-11) could be activated yet ineffective for controlling replication raises the possibility that ineffective CD4 T cell responses contribute to inflammatory damage without contributing to clearance.

It is tempting to attribute T cell-mediated control of *Chlamydia* replication in vitro to an indirect IFN-γ based mechanism such as induction of nitric oxide because the three most effective CD4 T cell clones (uvmo-1,-2,-3) make the most IFN-γ in response to infected epithelial cells. However production of IFN-γ in response to infected epithelial cells only loosely correlated with the ability of individual CD4 T cell clones to control *C. muridarum* replication, and none of the five CD4 T cell clones dependent on IFN-γ pretreatment were able to control *C. muridarum* replication when exogenous IFN-γ was added to epithelial monolayers at the time of infection; arguing against a direct effect of IFN-γ. In addition, *C. muridarum* replicating in murine epithelial cells (as reported herein, see also Nelson, et al., 2005; Roshick, et al., 2006), and mouse embryonic fibroblasts (Al-Zeer, et al., 2009; Coers, et al., 2008), is largely indifferent to recombinant IFN-γ. This makes it highly unlikely that IFN-γ of T cell origin, which would not be present until several hours after recognition (12-18 h post-infection), could directly contribute to the anti-*Chlamydia* effector mechanism of these clones. Inhibition of nitric oxide production does not interfere with CD4 T cell clones (uvmo-1,-2,-3) ability to control *C. muridarum* replication in vitro (Jayarapu, et al., 2010). These data support the hypothesis that the major role of IFN-γ at the epithelial interface during infection is to up regulate MHC class II on epithelial cells in order to efficiently activate *Chlamydia*-specific CD4 T cells.

These results illustrate that infection modestly blunted up regulation of cell surface MHC class II when IFN-γ was added at the time of infection but not when added 14 h prior to infection; consistent with data published by Zhong et al for *C. trachomatis* serovar L2 (Zhong, et al., 1999). An hypothesize that can account for these findings is that for the CD4 T cell clones dependent on IFN-γ pretreatment, IFN-γ is needed to up regulate MHC class II in order to increase the availability of MHC class II molecules to present *Chlamydia* antigens at the cell surface, though the effects IFN-γ effects on antigen processing cannot be ruled out. At the low levels of epithelial cell surface MHC class II seen with simultaneous IFN-γ addition and infection, the modest infection-associated blunting of MHC class II up regulation resulted in significant attenuation of CD4 T cell-mediated control of *C. muridarum* replication for the five IFN-γ dependent CD4 T cell clones; presumably through decreasing T cell recognition and/or activation. The in vivo importance of infection interference with IFN-γ-mediated up regulation of MHC class II however is unclear, as Darville et al (Darville, et al., Infect Immun 69:7419-7424, 2001) have shown physiologic IFN-γ levels in genital secretions by day three post *C. muridarum* infection, and El-Asrar et al have shown up regulated epithelial MHC class II in human trachoma clinical specimens (el-Asrar, et al., Br. J. Ophthalmol, 73:276-282; 73:399-400, 2005). These data combined with in vitro IFN-γ pretreatment data suggest that the host may be able to overcome this evasion tactic by ‘pretreating’ the vulnerable reproductive tract epithelium with IFN-γ prior to impending infection of individual epithelial cells.

Type 1 and 2 interferons modulated T cell activation by infected epithelial cells in this report, and *C. muridarum* infections of IFN-knockout mice have yielded interesting results in the existing literature. In wild type mice both type 1 (IFN-α/β) and type 2 interferon (IFN-γ) are part of the inflammatory milieu during *Chlamydia* genital tract infections. Nagarajan et al have shown that IFNAR1 knockout mice lacking the receptor for IFN-α/β clear *C. muridarum* from the genital tract more efficiently and with less oviduct pathology than wild type mice (Nagarajan, et al., 2008). As shown herein IFN-γ pretreatment of epithelial cells dramatically improved CD4 T cell activation by infected epithelial cells, and that this effect was greatly attenuated when IFN-β was included during pretreatment. The rate of *C. muridarum* genital tract clearance by different mouse strains has been correlated with the timing and magnitude of IFN-γ responses (Darville, et al., Infect Immun, 69:3556-3561; 69:7419-7424, 2001), which occur before demonstrable recall cellular immunity has developed (Su, et al., 1999). It is possible that the balance of IFN-β vs IFN-γ within an individual may be an important parameter affecting resolution of genital tract infections.

IFN-β attenuation of IFN-γ enhanced T cell activation correlated with marked attenuation of IFN-γ-induced MHC class II expression on C57epi.1 epithelial cells. This finding is consistent with previously described IFN-β blockade of IFN- γ-inducible MHC class II expression (Lu, et al., 1995). IFNAR1 knockout mice likely clear *C. muridarum* from the genital tract faster because the reproductive tract epithelium expresses higher levels of MHC class II, and on that basis infected epithelial cells more efficiently activate the CD4 T cells, allowing a larger fraction of *Chlamydia*-specific CD4 T cells to participate in clearance. MHC class II levels on C57epi.1 cells were only slightly higher in IFN-β/γ pretreated epithelial cells than IFN-β pretreated cells, and both were higher than on untreated cells; i.e. IFN-γ knockout mice (type 1 only interferon milieu) likely have some epithelial MHC class II, and that level is sufficient for IFN-γ independent CD4 T cell clones like uvmo-1,-2,-3 described in this report to mediate clearance, albeit with a lower efficiency, consistent with the observed low level residual genital tract shedding of *C. muridarum* in IFN-γ knockout mice.

Based on the demonstrated ability of *C. muridarum*-specific CD4 T cell clones to recognize infected upper reproductive tract epithelial cells and control *Chlamydia* replication in them, it is reasonable to interpret the CD4 depletion data (Morrison and Morrison, 2005) and MHC class II knockout mouse study (Morrison, et al., 1995) as showing a critical role for CD4 T cells in directly clearing *Chlamydia* from the genital tract. These results do not address the controversial role of CD8 T cells, do not rule out a redundant non-critical role for CD8 T cells in genital tract clearance. These data suggest that not all *Chlamydia*-specific $T_h1$ cells, even those generated during the course of a genital tract infection, are capable of contributing to clearance. Identification of the protective CD4 T cell sub-subset(s) and the antigens that they recognize may be critical for development of an effective *Chlamydia* vaccine. Accordingly, CD4 T-cell clones isolated from the reproductive tracts of mice that effectively cleared infections caused by *Chlamydia* were analyzed to isolate genes that were differentially expressed by these clones.

Referring now to Table 2, the clone (designated 'ineffective') is unable to control *Chlamydia* replication in epithelial cells in vitro; the clone (designated intermediate) does an ok job controlling *Chlamydia*, but the mechanism for controlling replication is not likely relevant in humans; while the clones (designated as effective x2) do an excellent job of controlling *Chlamydia* in addition, as indicated by their elevated level of Plac8, their mechanism is relevant to the immune response in humans. Plac8 (SEQ ID NO. 5 and 6) is an antibacterial peptide that is common to mice (SEQ ID NO. 6) and humans (SEQ ID NO. 5).

The critical gene identified herein involved in this immune response is Casd1 (SEQ ID NOs. 1 and 2), which is absent on the ineffective clone (−31.68 fold) and absent on the intermediate clone (−35.14 fold). It is present on both of the effective clones. A 30-fold is essentially all vs. none. Casd1 appears to be a protein without a known function or publication track record. Referring now to FIG. 8, Casd1 is >95% identical between mouse (SEQ ID NO. 2) and human (SEQ ID NO. 1). Referring now to FIG. 10, Casd1 has a predicted 271 an extracellular domain i.e. a potential cell surface marker for T cells that can interact with infected epithelial cells to control intracellular bacterial and possibly intracellular viral, protozoan, and fungal pathogens. Referring now to FIG. 9, the putative extracellular domain of Casd1 shows even higher levels of identify between the mouse (SEQ ID No. 4) and human forms (SEQ ID No. 3). Casd1 can serve as a surrogate marker for protective mucosal immunity in vaccine trials. Some methods for screening for a vaccine may include the steps of: vaccinating an animal or human, then evaluating for expansion of pathogen-specific Casd1+ CD4 T cells by flow cytometry. Plac8 could be similarly be used as vaccine surrogate marker utilizing the technique of intracellular staining with flow cytometry. The ability to evaluate a vaccine by an easy surrogate is the critical step for assessing early stage vaccines. The results obtained with *Chlamydia*, are also applicable to other intracellular bacteria including *Neisseria gonorrhea, salmonella, listeria, mycoplasma pneumonia, legionella*, and potentially any intracellular microbial pathogen. The same genes may also be important for the control of viral infections, including but not limited to, infections caused by viruses such as RSV, parainfluenza, metopneumovirus, rhinovirus, corona virus, rotavirus and the like. Nearly all viruses, except those transmitted by mosquitos, invade at a mucosal/epithelial surface.

EXPERIMENTAL

Materials and Methods

Mice

Female C57BL/6 and Balb/c mice were purchased from Harlan Laboratories (Indianapolis, Ind.). Female C57BL/6J, B6.C-H2$^{bm12}$/KhEg, and B6.C-H2$^{bm1}$/ByJ female mice were purchased from The Jackson Laboratory (Bar Harbor, Me.). All mice were housed in Indiana University Purdue University-Indianapolis (IUPUI) specific-pathogen-free (SPF) facilities. The IUPUI Institutional Animal Care and Utilization Committee approved all experimental protocols.

Cells, Bacteria, and Culture Reagents

C57epi.1 is a cloned oviduct epithelial cell line derived from a C57BL/6 mouse (H-2$^{b}$) using the methodology previously described (Derbigny, et al., 2005; Derbigny, et al., 2007; Johnson, R. M., 2004) except for initial ex vivo culture in SFM media supplemented with bovine pituitary gland extract (Gibco/Invitrogen, Carlsbad, Calif.) for several passages prior to switching to epithelial cell media supplemented as described below. The cultured C57epi.1 cells are grown at 37° C. in a 5% $CO_2$ humidified incubator in epithelial-cell media (1:1 Dulbecco's modified Eagle medium:F12K (Sigma; St. Louis, Mo.)), supplemented with 10% characterized fetal bovine serum (HyClone; Logan, Utah), 2 mM L-alanyl-L-glutamine (Glutamax I; Gibco/Invitrogen), 5 μg of bovine insulin/ml, and 12.5 ηg/ml of recombinant human FGF-7 (keratinocyte growth factor; Sigma). C57epi.1 cells were fixed in 1:1 acetone methanol and stained with an anti-cytokeratin monoclonal antibody AE1/AE3 (Cappel ICN; Irvine, Calif.) or control antibody 36-5-7 (anti-H-2K$^{k}$; BD Biosciences, San Diego, Calif.) and counterstained with DAPI (nuclear stain) to confirm an epithelial lineage as previously described (Johnson, R. M., 2004).

Mycoplasma-free *Chlamydia muridarum* (Nigg isolate), previously known as *C. trachomatis* strain mouse pneumonitis (MoPn), was grown in McCoy cells (American Type Culture Collection #CRL-1696). The titers of mycoplasma-free *C. muridarum* stocks were determined on McCoy cells with centrifugation as previously described (Johnson, R. M., 2004). U.V.-inactivated *C. muridarum* stocks were made by diluting concentrated stocks in sucrose-phosphate-glutamic acid buffer (SPG buffer), then exposing 3-4 ml of diluted stock in a sterile petri dish to 1200 J twice in a UV-Crosslinking Cabinet (Spectralinker, Spectronics corporation, Westbury, N.Y.). No viable *C. muridarum* inclusions were detectable in inoculated McCoy cell monolayers after U.V. inactivation.

"Soluble *C. muridarum* antigen" was prepared by infecting C57epi.1 epithelial cell monolayers in 4-175 $cm^2$ tissue culture flasks with *C. muridarum* at 3 IFU per cell. At 32 hours the monolayers were harvested with glass bead agitation in 15 ml of residual media per flask. Debris was pelleted with a low speed spin (1,400 rpm {464 g} for 10 minutes) and supernatant collected; then EBs were pelleted out of medium (depleted) with a high speed spin (16,000 rpm {25,000 g} for 30 minutes). The resulting supernatant was concentrated with a 10,000 kd molecular weight cutoff centrifugal filter (Amicon-15; Millipore Bilerica, Mass.), aliquoted and stored at −80 C.

Infection of Mice

C57BL/6 mice were treated with 2.5 mg of depo-progesterone (Depo-Provera; Pfizer NY, N.Y.) injected subdermally one week prior to infection. Vaginal infections were accomplished with $5 \times 10^4$ IFU of *C. muridarum* in 10 µl of SPG buffer. Mice were swabbed 7 days later to confirm infection. Vaginal swab IFU were recovered in SPG buffer and quantified using McCoy cell monolayers as previously described (Johnson, R. M., 2004).

Generation of CD4 T Cell Clones

T cell cultures were grown in RPMI 1640 (Sigma) supplemented with 10% characterized fetal bovine serum (HyClone), 2 mM L-alanyl-L-glutamine (Glutamax I; Gibco/Invitrogen), 25 µg/ml gentamicin (Sigma), and $5 \times 10^{-5}$M 2-mercaptoethanol (Sigma). This supplemented media is referred to as T cell media for the remainder of the text. Secondary mixed lymphocyte culture supernatants (2° MLC) were prepared by combining $25 \times 10^6$ C57BL/6 splenocytes with $25 \times 10^6$ U.V.-irradiated (1500 rads) Balb/c splenocytes in an upright 25 cm² flask containing 20 ml of DMEM supplemented with 10 mM Hepes, 10% characterized fetal bovine serum (HyClone), 2 mM L-alanyl-L-glutamine (Gibco/Invitrogen), 25 µg/ml gentamicin (Sigma), and $5 \times 10^{-5}$M 2-mercaptoethanol (Sigma); DME CM. Ten days later the viable C57BL/6 T cells were recovered and stimulated with irradiated Balb/c splenocytes; $10 \times 10^6$ C57BL/6 T cells+$25 \times 10^6$ irradiated Balb/c splenocytes in 20 ml of DME CM in an upright 25 cm² flask for 20 h. Supernatants were collected, filtered through 0.22 um filters, aliquoted, and stored at −80° C. until use.

*Chlamydia*-specific CD4 T cell clones were derived from immune C57BL/6 (H-$2^b$) female mice that had cleared a primary *C. muridarum* genital tract infection and were seven days into clearing a secondary vaginal challenge with *C. muridarum*. Immune splenocytes harvested from mice were plated at $12.5 \times 10^6$ cells per well in tissue culture treated 12 well plates, in T cell media containing murine recombinant IL-1α (2 ηg/ml), IL-6 (2 ηg/ml), IL-7 (3 ηg/ml), IL-15 (4 ηg/ml), human recombinant IL-2 (100 units/ml), 20% 2° MLC, and 10 µg of U.V.-inactivated *C. muridarum* (~2.5 IFU equivalents per splenocyte) or 15 µl of soluble *C. muridarum* antigen (~1.5 cm² infected monolayer equivalents). The resulting polyclonal T cell populations were serially passed and limiting diluted to obtain CD4 T cell clones. CD4 T cell clones designated uvmo-1, uvmo-2, uvmo-3, and uvmo-4 were derived from four independent polyclonal T cell lines originating from immune splenocytes of four different mice using U.V.-inactivated *C. muridarum* as antigen. These T cell clones also recognize irradiated splenocytes pulsed with U.V.-inactivated *C. muridarum* grown up in C57epi.1 (H-$2^b$) epithelial cells, ruling out specificity for McCoy alloantigens originating from the McCoy fibroblasts used to propagate *C. muridarum* (data not shown). CD4 clones designated LN4-10, LN4-11, LN4-12, and LN4-13 were derived from the lymph nodes draining the reproductive tract (inguinal, ilieac, and para-aortic), and Sp14-10 and Sp1-11 from immune splenocytes, of a fifth mouse using "soluble *C. muridarum* antigen". With the exception of IL-2, the recombinant T cell growth factors used reflect those secreted by infected epithelial cells (Johnson, R. M., 2004) and bone marrow derived dendritic cells pulsed with heat-killed *C. muridarum* (Shaw, et al., 2001), which are remarkably similar. All T cell clones listed above were CD4$^+$CD8$^-$ by flow cytometry (data not shown).

For routine passage of clones uvmo-1,-2,-3, $1 \times 10^5$ CD4 clone cells were plated in 24 well tissue culture-treated wells containing 1.5 ml of T cell media/15% MLC supernatant supplemented with murine IL-1α (2 ηg/ml), IL-6 (2 ηg/ml), IL-7 (2 ηg/ml), IL-15 (4 ηg/ml), and human recombinant IL-2 (75 units/ml) plus $5 \times 10^6$ γ-irradiated C57BL/6 splenocytes (1200 rads) that had been pre-pulsed at 37° C. with 2.5 IFU equivalent U.V.-irradiated *C. muridarum* per splenocyte for 30 minutes. The remaining clones (uvmo-4, LN4-10,-11,-12,-13, and Sp14-10,-11) were passed using the same conditions except the irradiated splenocytes came from female mice that had self-cleared a *C. muridarum* genital tract infection (i.e. immune-irradiated splenocytes) and the antigen was 1.5 cm² equivalent "soluble *C. muridarum* antigen" per $5 \times 10^6$ irradiated splenocytes. Immune-irradiated splenocytes are likely better able to efficiently process antigens present in low concentrations in the soluble antigen preparation (Rock, et al., 1984). *Chlamydia*-specific CD4 T cell clones were passed every 6-8 days under these conditions. For the experiments in this manuscript T cells were used on day 7 of their culture cycle. Recombinant murine cytokines were purchased from a commercial vendor (R&D systems, Minneapolis, Minn.). Human recombinant IL-2 was obtained from Chiron Corporation (Emeryville, Calif.).

Epithelial Cell Infections

C57epi.1 cells were plated in 6-, 12-, 24-, or 48-well tissue culture plates and were used when confluent. Cells were infected with 3 inclusion-forming-units (IFU) of *C. muridarum* per cell in 0.25-2 ml of culture medium depending on the culture plate format. The plates were centrifuged at 1200 RPM (300 g) in a table-top centrifuge for 30 minutes then incubated at 37° C. in a 5% CO$_2$ humidified incubator without change of medium for 3-21 h, depending upon the assay. Mock-infected wells received an equivalent volume of sucrose SPG buffer lacking *C. muridarum*.

Antibodies and Flow Cytometry

T cells were dislodged from tissue culture plastic by removal of media and incubation for 5 minutes in Versene (PBS/EDTA). C57epi.1 cells were dislodged from tissue culture plastic using a versene wash followed by Hank's salt-based enzyme free cell dissociation buffer (Sigma). Cells were stained for 20 minutes on ice in PBS/2% BSA with: PE-coupled 53-5.8 (CD8β), PE-coupled YTS191.1 (CD4) (Cedarlane Laboratories; Burlington, N.C.), FITC-coupled Mouse IgG2a (control antibody), PE-coupled Rat IgG2b (control antibody), PE-coupled M5/114.15.2 (MHC class II), GK1.5 (CD4; low endotoxin/no azide), Rat IgG2a (control; low endotoxin/no azide) (Ebioscience; San Diego, Calif.). Cells were fixed with 1% paraformaldehyde after staining Cells were analyzed at the IU Cancer Center Flow Cytometry Facility using a FACScan cytometer (BD Biosciences).

ELISA Determination of IFN-γ

Relative interferon-gamma (IFN-γ) levels were determined by ELISA using monoclonal antibodies XMG1.2, according to the manufacturer's protocol (Pierce-Endogen; Rockford, Ill.). Recombinant murine IFN-γ (R&D Systems) was used as the standard.

T Cell Proliferation Assays

Epithelial cell targets were treated with 50 µg/ml of mitomycin C for 20 minutes at 37° C., washed twice with versene, then dislodged with enzyme free cell dissociation buffer, filtered through a 40 µM nylon filter, and counted. $5 \times 10^4$ T cells with $5 \times 10^4$ epithelial cells were co-cultured in 200 µl of T cell media. At 36 hours culture supernatants were harvested (50 μl) for cytokine analysis and wells pulsed with 0.5 μCi of $^3$H thymidine per well for 12 h. Proliferation assays were harvested on glass fiber filters and counted using a Packard Matrix 9600 direct beta counter.

Replication

To test whether the CD4 clones could control the *Chlamydia* replication in vitro, C57epi.1 monolayers in 48 well plates were untreated, or treated with IFN-γ (10 ηg/ml) for 14 h prior to infection or at the time of infection with 3 IFU of *C. muridarum* per cell. After addition of *C. muridarum* the plates were spun at 1200 rpm (300 g) for 30 minutes. Four hours after infection the inoculum was removed CD4 T cell clones were added in T cell media. 36 h post-infection, wells were scraped, harvested, and stored at −80° C. until *C. muridarum* titers determined on McCoy monolayers as previously described (Johnson, R. M., 2004). Recombinant murine IFN-γ at all concentrations tested (up to 1000 ρg/ml) had no effect on *C. muridarum* titrations done on the McCoy monolayers; maximum IFN-γ carryover in dilutions used for quantifying *C. muridarum* was <50 ρg/ml.

Preparation of T-Cells for Microarray Analysis

*Chlamydia*-specific T cell clones uvmo-1 (known as uvmo-4 in publication), sp14-10, 2-14 (known as uvmo-2 in publication), and 3-10 (known as uvmo-3 in publication) were derived from immune C57BL/6 mice that had previously cleared a genital tract infection with *Chlamydia muridarum*. The antigen presenting cell in culture for uvmo-1 and sp14-10 was irradiated splenocytes from immune C57BL/6 mice. The antigen presenting cell in culture for 2-14 and 3-10 was irradiated splenocytes from naïve C57BL/6 mice. The *Chlamydia* antigen for uvmo-1, 2-14, and 3-10 was ultraviolet irradiated *Chlamydia muridarum*. The antigen for clone sp14-10 was a *C. muridarum* infected cell lysates depleted of elementary bodies by centrifugation.

Microarray Analysis

The four T cell clones grown as described in the above were harvested at the end of their usual culture cycle, purified by histopaque 1083 centrifugation to remove debris from irradiated splenocyte APC, then cultured for 2.5 days in usual media supplemented with secondary mixed lymphocyte culture supernatant (15% vol/vol), recombinant IL-1a, IL-2, IL-6, IL-7, IL-15. On day 2.5 the media was aspirated off the adherent T cells, and then T cells lysed and total RNA isolated using the RNAeasy Kit with DNAse treatment available from Qiagen (Valencia, Calif.) according the manufacturers protocol. The experiment was performed four times. Total RNA was delivered to the Indiana University Center for Medical Genomics who performed Principle Component Analysis (PCA) mapping using a mouse gene 1.0 ST array purchased from Affymatrix, (Santa Clara, Calif.) and data analysis.

Analysis of Casd1 in Mice and Humans

The mouse and human Casd1 reference mRNA sequences were translated and compared were compared using the program Vector NTI 11 Advanced 11 software available from Invitrogen® (Carlsbad, Calif.). The tertiary structure of the protein was estimated using CBS Prediction Servers available at www.cbs.dtu.dk/services. Based on this analysis the region between residues 75 and 272 was estimated to be an extracellular domain. Equivalent regions of the mouse and human form of the protein were compared using Vector NTI 11 Advanced 11 software.

Statistical Analysis

Summary figures for each experimental investigation are presented as 'pooled' means and with their associated standard error of the mean (SEM). Figure legends indicate the number of independent experiments pooled to generate each figure. Student's two-tailed t test was used to assess significance of pooled experimental data. p values<0.05 were considered statistically significant.

1. Derivation and Characterization of the C57epi.1 Oviduct Epithelial Cell Line and *Chlamydia*-Specific CD4 T Cell Clones.

Figure 1B:
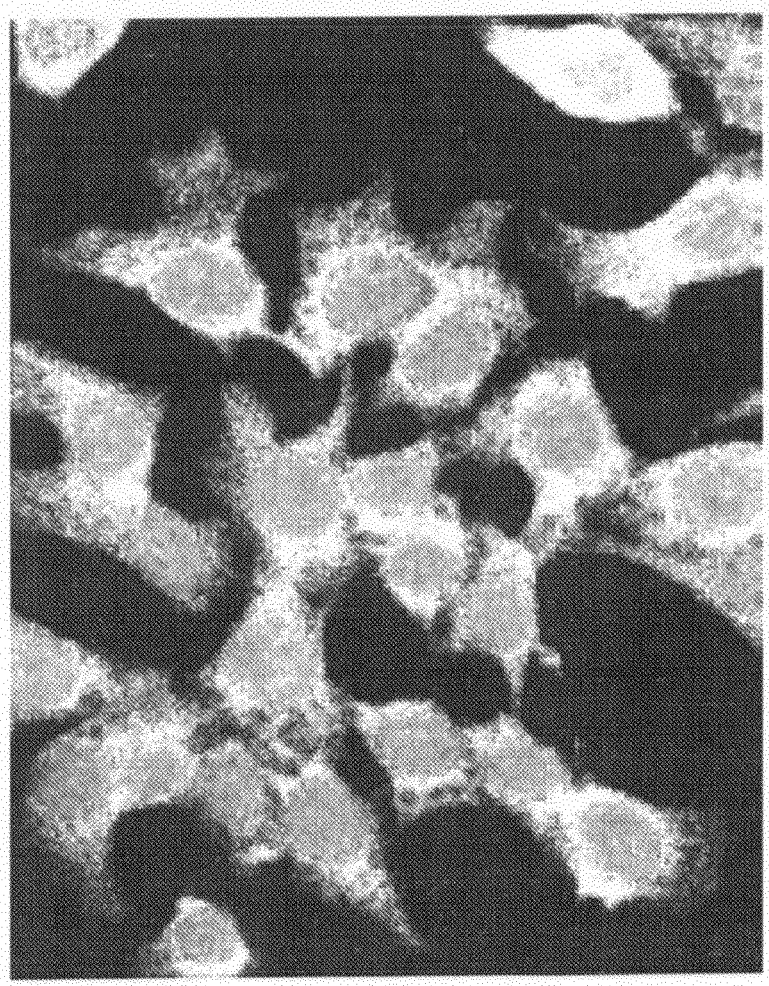
FIG. 1B. Staining for cytokeratins to confirm an epithelial lineage.
Figure 1C:
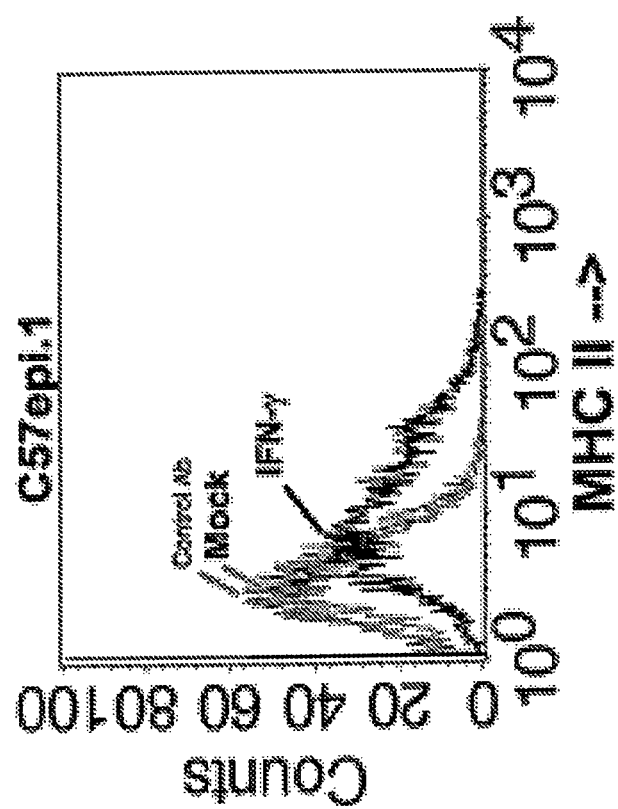
FIG. 1C. C57epi.1 cells were exposed to 10 ηg/ml IFN-γ for 29 h, then stained for MHC class II and analyzed by flow cytometry.

An upper reproductive tract epithelial cell line was derived from a C57BL/6 (H-2$^b$) mouse by limiting dilution cloning as described in the materials and methods. C57epi.1 epithelial cell monolayers in chamber slides were fixed and stained with control antibody (FIG. 1A.) and antibody specific for cytokeratins (FIG. 1B.). C57epi.1 cells express cytokeratins consistent with an epithelial lineage. Consistent with an epithelial lineage they also have IFN-γ-inducible MHC class II expression (FIG. 1C.).

There are no published murine CD4 or CD8 *Chlamydia*-specific T cell clones derived from mice that self-cleared primary genital tract infections. A panel of ten *C. muridarum*-specific CD4 T cell clones from five C57BL/6 (H-2$^b$) female mice that cleared primary genital infections was created. Immune lymphocytes were harvested from spleens and lymph nodes draining the genital tract one week into a second vaginal challenge. The *Chlamydia* antigens used to activate T cells in vitro were crude preparations of U.V.-irradiated *C. muridarum* elementary bodies and soluble *C. muridarum* antigens; the APCs for routine passage were naïve irradiated C57BL/6 splenocytes or immune-irradiated splenocytes. C57epi.1 cells were pretreated with IFN-γ, then mock-infected or infected with *C. muridarum* for 12 and 18 h prior to harvest for use as targets. The ten *C. muridarum*-specific CD4 T cell clones were tested for their ability to recognize mock-infected versus *C. muridarum*-infected C57epi.1 epithelial cells at 12 and 18 h post-infection. They were also tested for their ability to recognize mock-pulsed syngeneic irradiated naïve splenocytes (autoreactivity control) versus immune syngeneic irradiated splenocytes pulsed with U.V.-inactivated *C. muridarum* (specific antigen) (Table 1). The T cell assays were done in the presence of 10 μg/ml tetracycline to block synthesis of additional *Chlamydia* polypeptides and progression of infection. Immune-irradiated splenocytes pulsed with *C. muridarum* secreted a modest amount of IFN-γ without proliferating, while naïve irradiated splenocytes make no detectable IFN-γ under identical conditions (data not shown). For the splenocyte APC data in Table 1, the IFN-γ produced by immune-irradiated splenocytes pulsed with U.V.-inactivated *C. muridarum* in control wells lacking CD4 T cell clones was subtracted from IFN-γ produced in experimental wells containing antigen-pulsed immune-irradiated splenocytes plus CD4 T cell clones. This IFN-γ accounting procedure had no affect on the experimental conclusions.

As illustrated by the data in Table 1, all CD4 T cell clones, regardless of derivation strategy, were able to recognize infected epithelial cells and immune splenocytes pulsed with U.V.-inactivated *C. muridarum*. CD4 T cell clones differed in their ability to recognize infected epithelial cells at 12 h and 18 h post-infection; and T cell activation as measured by IFN-γ production was significantly less for infected epithelial cells than for antigen-pulsed immune splenocytes for all CD4 T cell clones. The limited number of T cell clones derived using the different strategies is too small to draw conclusions about derivation-specific differences in relative activation by antigen-pulsed splenocytes versus infected epithelial cells. However, it is clear from comparing each clone's activation by infected epithelial cells to its activation by antigen-pulsed irradiated splenocytes that *Chlamydia*-specific CD4 T cell activation by infected epithelial cells was sub-maximal for all clones tested.

TABLE 1

Summary of IFN produced in response to *C. muridarum* specific CD4 T-cell clones.
TABLE 1. IFN production by *C. muridarum*-specific CD4 T-cell clones[a]

| | IFN production (pg/ml) by: | | | | |
|---|---|---|---|---|---|
| | Epithelial cells | | | Immune splenocytes | |
| T-cell clone | Mock infected | Infected for 12 h | Infected for 12 h[b] | Mock infected | Pulsed[c] |
| uvmo-1[df] | 420 ± 180 | 590 ± 100 | 2,820 ± 640* | 1,212 ± 867 | 414,000 ± 70,000* |
| uvmo-2[df] | 29 ± 5 | 111 ± 48* | 2,800 ± 360* | 0 | 146,000 ± 44,000* |
| uvmo-3[df] | 45 ± 20 | 170 ± 24* | 3,630 ± 200* | 0 | 323,000 ± 67,000* |
| uvmo-4[dg] | 12 ± 6 | 56 ± 58 | 77 ± 53* | 0 | 176,000 ± 17,000* |
| LN4-10[eg] | 4 ± 26 | 26 ± 26 | 235 ± 56* | 0 | 86,700 ± 7,400* |
| LN4-11[eg] | 26 ± 17 | 35 ± 11 | 335 ± 90* | 0 | 86,000 ± 5,500* |
| LN4-12[eg] | 0 ± 4 | 0 ± 3 | 96 ± 38* | 0 | 125,000 ± 21,000* |
| LN4-13[eg] | 0 ± 5 | 0 ± 2 | 216 ± 100* | 0 | 97,000 ± 11,000* |
| Spl4-10[eg] | 0 ± 5 | 20 ± 25 | 273 ± 99* | 0 | 125,000 ± 21,000* |
| Spl4-11[eg] | 47 ± 7 | 71 ± 13* | 204 ± 45* | 0 | 39,000 ± 9,000* |

2. *C. Muridarum*-Specific CD4 T Cells Control *C. Muridarum* Replication in Epithelial Cells in Vitro with Variable Dependence on IFN-γ.

Igietseme et al (Igietseme, et al., 1994) showed that T cell lines that protected mice from vaginal infections with *C. muridarum* in adoptive transfer experiments were also able to control *C. muridarum* replication in a polarized epithelial tumor cell line in vitro. The panel of CD4 T cell clones was tested to determine the ability of specific clones to control *C. muridarum* replication in C57epi.1 epithelial cells (FIG. 2). Monolayers of C57epi.1 cells in 48 well plates (~200,000 epithelial cells per well) were untreated or treated with IFN-γ, either 14 h prior to infection or at the time of infection, then infected with *C. muridarum*. Four hours post-infection the inoculating media was removed and replaced with T cell media containing CD4 T cell clones; 150,000 T cells were added per well for an effector-to-target ratio of ~0.75:1. 32 h later the wells were harvested with additional SPG buffer and recovered *C. muridarum* titered on McCoy monolayers to score replication. Pretreatment of C57epi.1 with IFN-γ had a modest effect on *C. muridarum* replication in the control wells (media 15±10×10⁶ IFU/well vs IFN-γ treatment 4±2×10⁶ IFU/well; pooled means from two experiments, pvalue<0.001). IFUs recovered from experimental wells were compared with identically treated (untreated or IFN-γ treated) parallel control wells (no T cells) to calculate % control replication. This normalization controls for the difference in *C. muridarum* replication in the untreated vs. IFN-γ treated C57epi.1 cells.

Figure 2A:
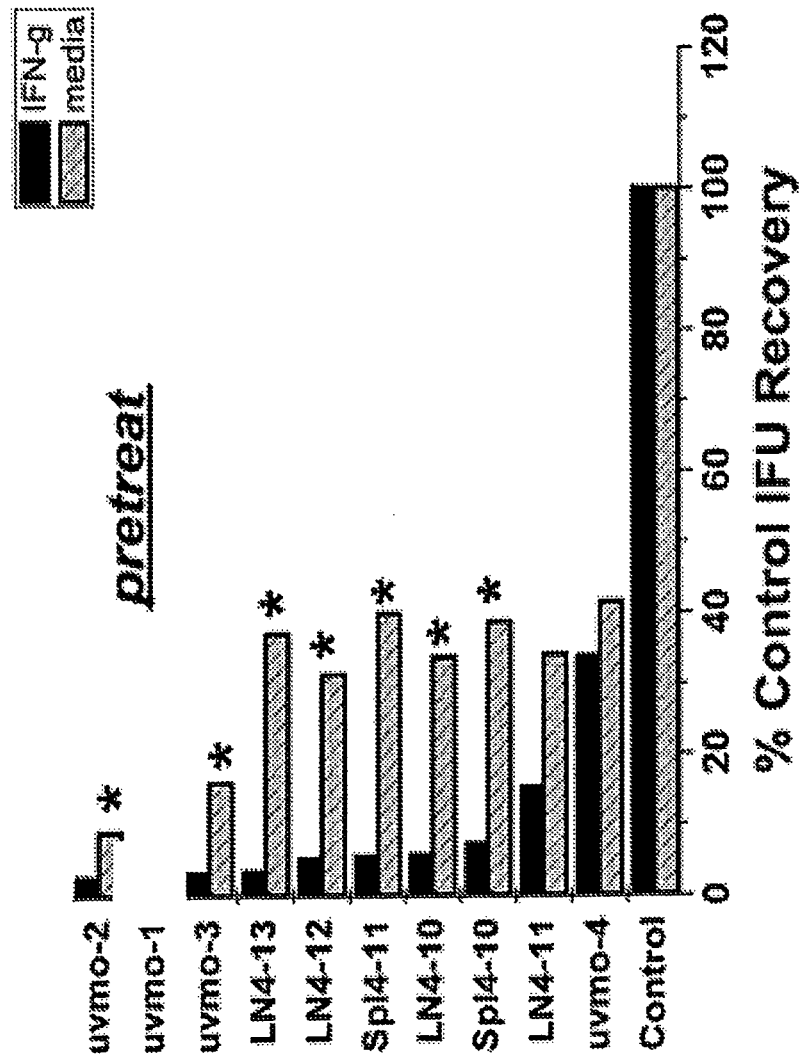
FIG. 2A. CD4 T cell clones control *C. muridarum* replication in epithelial cells pretreated with IFN-γ in vitro; correlation with IFN-γ inducible MHC class II expression in FIG. 2C FIG. 2B. CD4 T cells control *C. muridarum* in C57epi.1 monolayers simultaneously exposed to IFN-γ and infected with *C. muridarum*; correlation with IFN-γ inducible MHC class II expression in FIG. 2D.

Eight of the ten CD4 T cell clones were able to block>90% of *C. muridarum* replication when epithelial cells were treated with IFN-γ prior to infection (FIG. 2A., black bars). The two clones that could not were LN4-11 and uvmo-4. Control of replication only loosely correlated with each CD4 T cell clone's ability to make IFN-γ when activated by infected epithelial cells (see Table 1). The "ineffective" clone uvmo-4 (77 pg/ml) was one of the least activated-by-infected-epithelial-cell T cell clones, while the other "ineffective" clone LN4-11 (335 pg/ml) was in the middle. CD4 T cell clones that made less IFN-γ than LN4-11 (LN4-10,-13, Sp14-10,-11) were still able to control *C. muridarum* replication. Referring now to FIG. 2A. C57epi.1 monolayers were treated with 10 ηg/ml IFN-γ for 14 h prior to infection. Monolayers were then infected with 3 IFU per cell. CD4 T cell clones added 4 h later. Wells were harvested 36 h post-infection and IFU quantified. Seven of the ten clones showed improved control of *C. muridarum* replication with IFN-γ pretreatment of the epithelial monolayers (asterisks). Of note, three CD4 T cell clones (uvmo-1, uvmo-2, uvmo-3) were able to block≥80% *C. muridarum* replication without IFN-γ pretreatment of the epithelial monolayers.

Figure 2B:
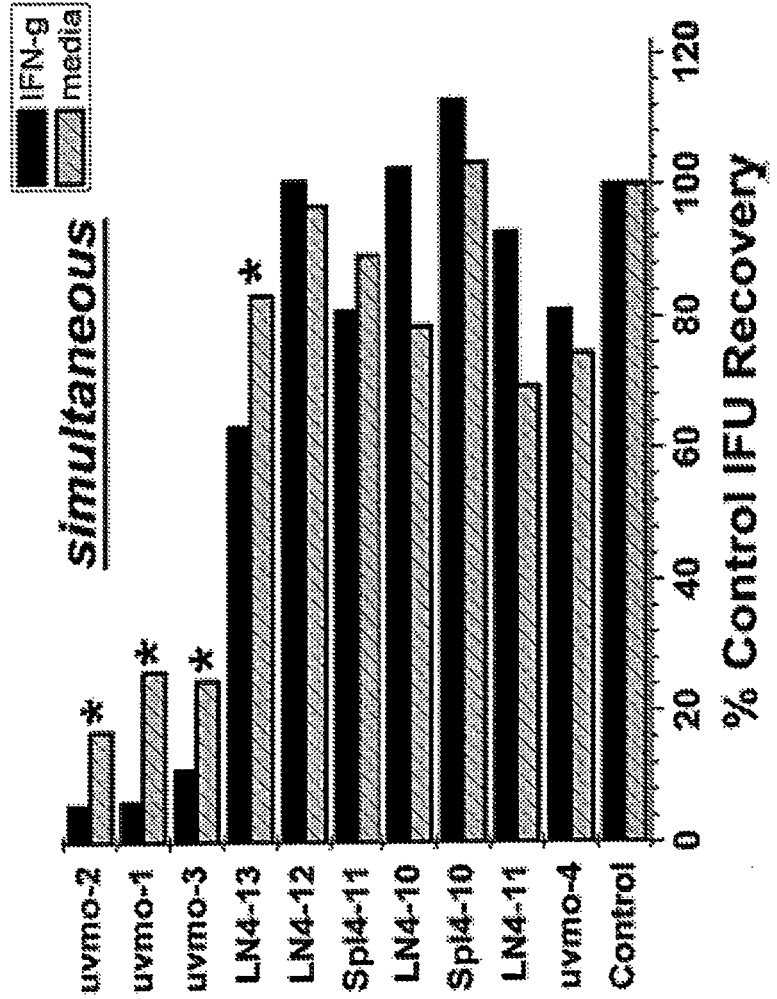
FIG. 2C. Flow cytometric analysis of MHC class II expression with 14 h IFN-γ pretreatment plus 18 h post-infection (approximating conditions in FIG. 2A).
FIG. 2D. MHC class II expression with simultaneous IFN-γ exposure and infection stained 18 h post-infection (approximating the conditions in FIG. 2B).
Figure 2C:
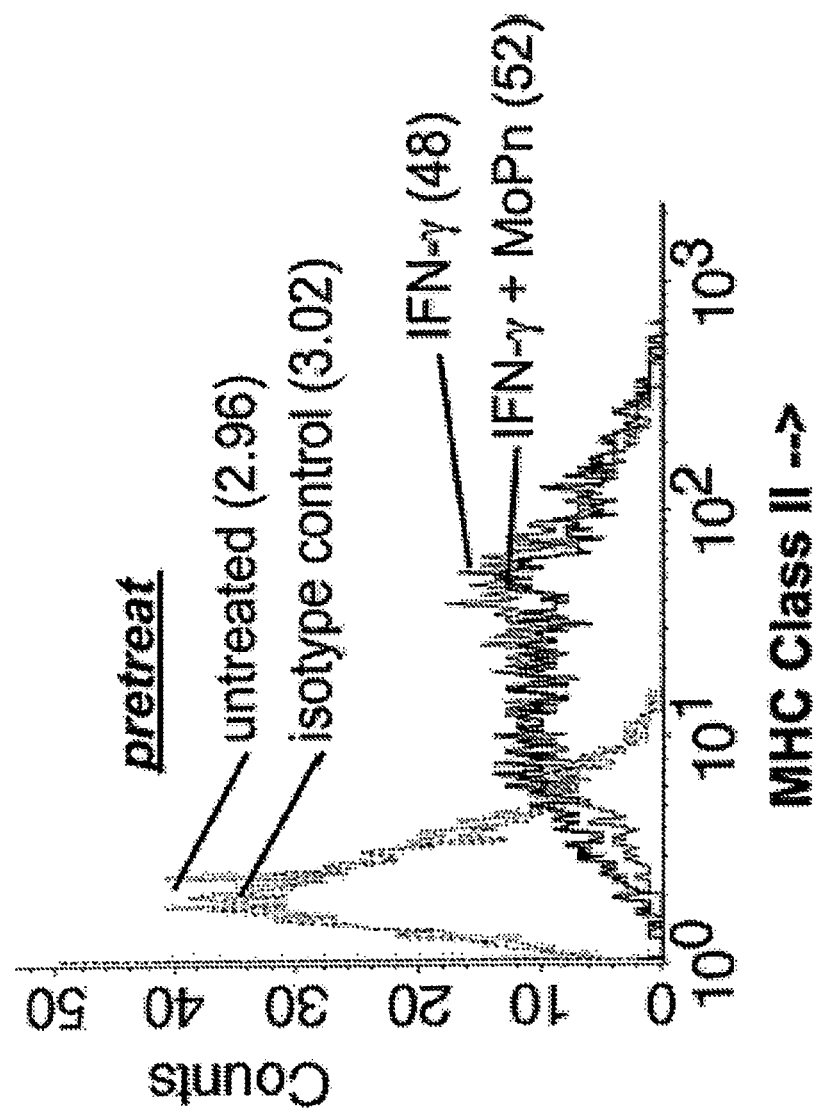
Figure 2D:
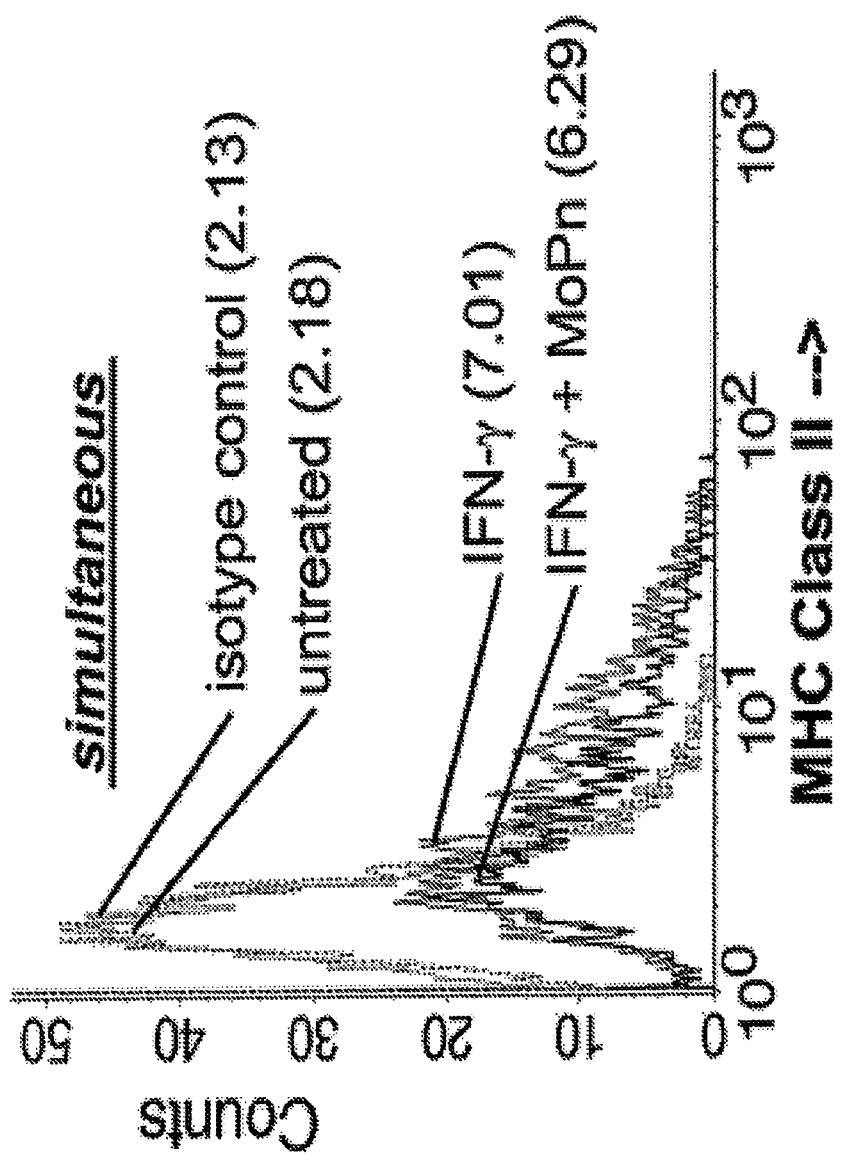
Figure 3A:
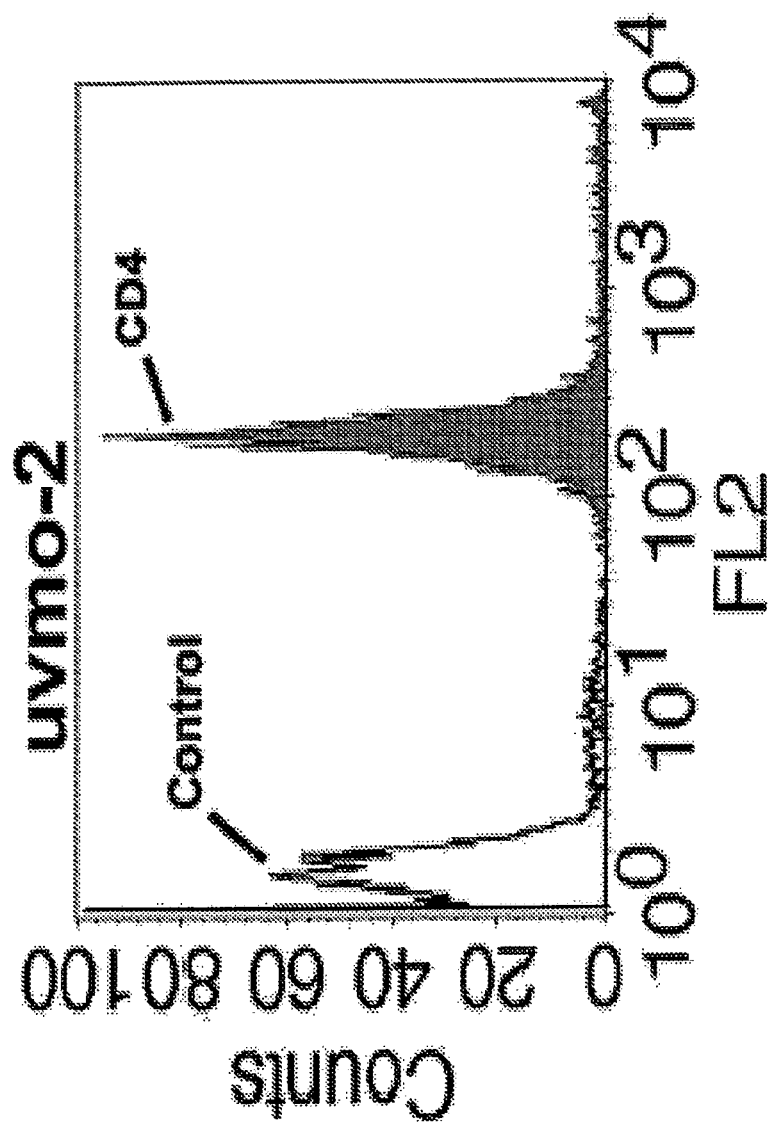
FIG. 3A. MHC class II restriction of CD4 T cell clones. Representative staining of CD4 T cell clone uvmo-2 with an isotype control antibody and a monoclonal antibody specific for CD4.
Figure 3B:
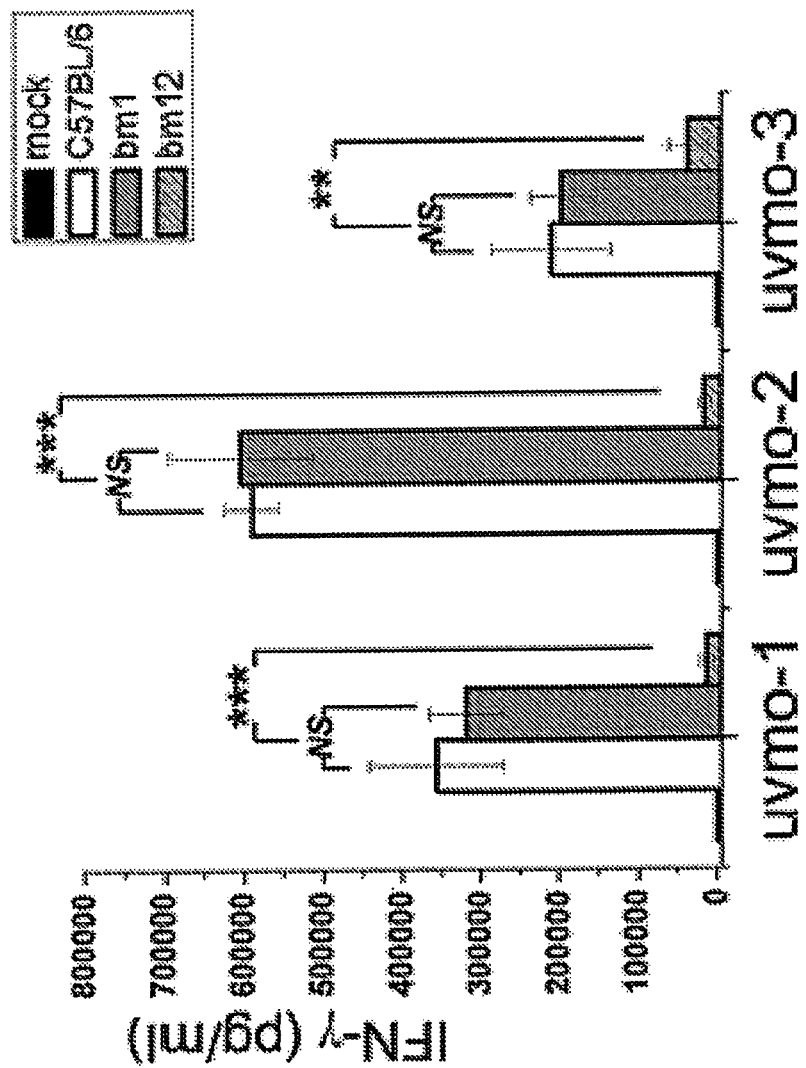
FIG. 3B. Plot of IFN-γ measured with T-cell clones: uvmo-1, uvmo-2 and uvmo-3. The results of MHC restriction mapping with inbred mouse strains.
Figure 4:
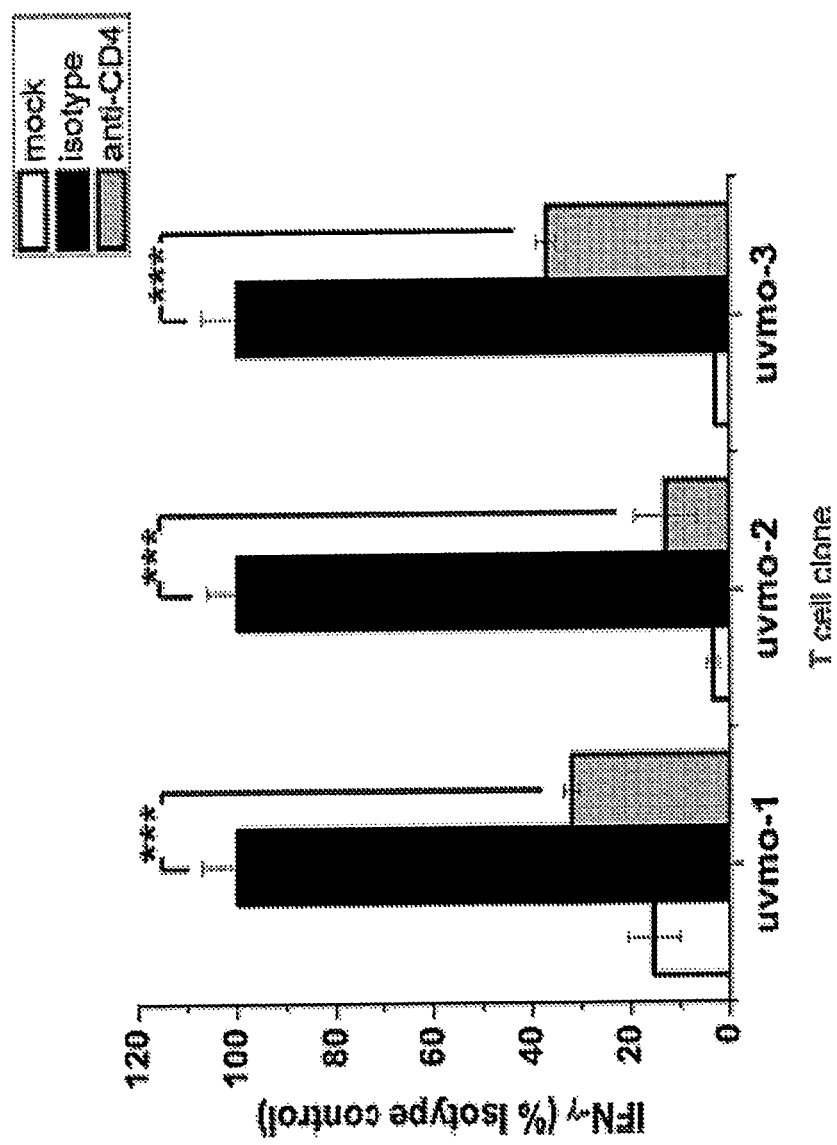
FIG. 4. Plot of IFN-γ (expressed as a % percent of a control) measured for T-cell clones: uvmo-1, uvmo-2 and uvmo-3. *Chlamydia*-specific CD4 T cell clones use the CD4 co-receptor during recognition of infected C57epi.1 epithelial cells.

A previous study with human epithelial tumor cell lines and *C. trachomatis* serovar L2 showed that Chlamydia-infection prior to IFN-γ exposure blocked IFN-γ-mediated up regulation of epithelial MHC class II by degrading an MHC class II transcription factor (Zhong, et al., 1999). To test whether *C. muridarum* could avoid cell mediated immunity via this mechanism in vitro, the experiments shown in FIG. 2A., were repeated except that IFN-γ was added at the time of *C. muridarum* infection. Referring now to FIG. 2B. C57epi.1 monolayers were simultaneously exposed to IFN-γ and infected with *C. muridarum*. Wells were harvested 36 h later and IFUs quantified. Aggregate data from two independent experiments; *=p value<0.05 comparing the untreated monolayer to the IFN-γ treated monolayer for an individual clone. Addition of IFN-γ at the time of infection had no effect on *C. muridarum* replication (media 5.6±0.8×10⁶ IFU/well vs. IFN-γ treatment 5±1×10⁶ IFU/well). When IFN-γ was added at the time of infection only three CD4 clones were able to block≥90% of *C. muridarum* replication (uvmo-1, uvmo-2, uvmo-3), and only four of the ten clones showed improved control of *C. muridarum* replication with IFN-γ treatment of the epithelial monolayers (FIG. 2B., asterisks).

As reported herein, two of ten Chlamydia-specific CD4 T cell clones were ineffective even though they recognized infected epithelial cells, five clones effectively controlled *C. muridarum* in an IFN-γ-dependent fashion, and three clones efficiently controlled *C. muridarum* replication even without exogenous IFN-γ treatment of the epithelial monolayers. In addition, *C. muridarum* infection interfered with the ability of the five IFN-γ-dependent CD4 clones to control replication when IFN-γ was added at the time of infection, but not when added 14 h prior to infection. Based on the existing literature, these data strongly suggested a negative effect of *C. muridarum* infection on IFN-γ-mediated up regulation of MHC class II, and that the level of epithelial MHC class II expression was a limiting factor for the IFN-γ dependent CD4 T cell clones (LN4-10, -12, -13, Sp14-10,-11). There was no clear correlation between lymphoid organ of origin (spleen versus draining lymph node), or antigen used ex vivo to activate T cell lines (U.V.-*C. muridarum* versus soluble antigen), and the ability of the resulting T cell clones to control in vitro *C. muridarum* replication.

The effect of *C. muridarum* on inducible epithelial cell surface MHC class II expression using the same experimental protocol used for the replication control experiments was determined. C57epi.1 cells pretreated with IFN-γ for 14 h prior to infection (FIG. 2C.) were compared to C57epi.1 cells treated with IFN-γ at the time of infection (FIG. 2D.). 18 h post infection the epithelial monolayers were harvested, stained for MHC class II, and analyzed by flow cytometry. The flow cytometry data shown are representative of two independent experiments. Numbers in parentheses are the mean fluorescence values in arbitrary units for each condition. Consistent with the *C. trachomatis* serovar L2 data and the hypothesis that the role of IFN-γ for the IFN-γ-dependent CD4 T cell clones is to up regulate epithelial MHC class II, *C. muridarum* infection modestly but reproducibly blocked MHC class II up regulation by IFN-γ when it was added at the time of infection (FIG. 2D.), but not 14 h prior to infection (FIG. 2C.). Because of the difference in duration of IFN-γ exposure, the absolute amount of cell surface MHC class II was higher with 14 h IFN-γ pretreatment (FIG. 2C.) than IFN-γ addition at the time of infection (FIG. 2D.). The three most effective CD4 clones, uvmo-1,-2,-3, achieved near maximal inhibition of replication with the modest increase in MHC class II induced by addition of IFN-γ at the time of infection, while the IFN-γ dependent CD4 clones (LN4-10,-12,-13, Sp14-10,-11) could not control *C. muridarum* with this lower level of MHC class II. This data, combined with the data in Table 1 showing that uvmo-1,-2,-3 are better activated by infected epithelial cells as measured by IFN-γ production, is consistent with the hypothesis that the IFN-γ independent CD4 clones are better able to control *Chlamydia* replication because they are better activated at lower levels of epithelial MHC class II. At the higher levels of epithelial MHC class II induced by 14 h of IFN-γ pretreatment, there was little difference between uvmo-1,-2,-3 and LN4-10,-12,-13, Sp14-10,-11 in their ability to control *C. muridarum* replication (FIG. 2A.).

3. *Chlamydia*-Specific CD4 T Cell Clones are MHC Class II Restricted and Utilize the CD4 Co-Receptor when Activated by Infected Epithelial Cells.

For logistical reasons, three CD4 T cell clones (uvmo-1, uvmo-2, and uvmo-3) were focused on for further investigate CD4 T cell interactions with infected reproductive tract epithelial cells. These three CD4 T cell clones were derived from independent mice and were the most effective at controlling *C. muridarum* in vitro.

The role of the CD4 co-receptor during activation by infected epithelial cells because this directly addresses the role of MHC class II in T cell activation was investigated. All the CD4 T cell clones were $CD4^+$ $CD8^-$. A representative CD4 staining for T cell clone uvmo-2 is shown in FIG. 3A.

Referring now to FIG. 3B. Briefly, 50,000 CD4 T cell clone cells were co-cultured with $1\times10^6$ UV-*C. muridarum*-pulsed or mock-pulsed irradiated naïve splenocytes for 36 h in the presence of tetracycline; then culture supernatants were harvested and analyzed for IFN-γ content by ELISA. Black bars=C57BL/6J irradiated splenocytes mock-pulsed control (syngeneic); white bars=C57BL/6J irradiated splenocytes pulsed with 2.5 IFU equivalents U.V.-inactivated *C. muridarum* per cell (syngeneic); gray bars=bm1 irradiated splenocytes pulsed with U.V.-inactivated *C. muridarum* (MHC class I mismatch); light gray hatched bars=bm12 irradiated splenocytes pulsed with U.V.-inactivated *C. muridarum* (MHC class II mismatch). Aggregate data from two independent experiments±SEM; =p value<0.01; *=p value<0.001, comparing C57BL/6J to bm1 and bm12. NS=not significant. The MHC restriction element for uvmo-1, -2, -3 was mapped using C57BL/6J (H-$2^b$), bm1 (H-$2Ia^bK^{bm1}$), and bm12 mice (H-$2Ia^{bm12}$) naïve splenocytes mock-pulsed or pulsed with U.V.-inactivated *C. muridarum*. These C57BL/6-derived mouse strains have a single MHC class II αβ heterodimer; C57BL/6J splenocytes are syngeneic with the CD4 T cell clones, bm1 splenocytes are mismatched at the MHC class I K locus, and bm12 splenocytes are mismatched at the MHC class II locus. All three clones recognized C57BL/6J splenocytes and bm1 splenocytes pulsed with U.V.-inactivated *C. muridarum*, but their recognition of bm12 splenocytes (MHC class II mismatch) pulsed with *C. muridarum* was negligible or markedly attenuated (FIG. 3B.). The bm12 MHC class II heterodimer differs from that of the C57BL/6J heterodimer by three amino acids in the beta chain (McIntyre and Seidman, 1984). This small change likely accounts for the residual partial activation of the uvmo-3 clone by U.V.-*C. muridarum*-pulsed bm12 splenocytes. With that small caveat, all three CD4 T cell clones clearly recognize *Chlamydia* antigens presented by an MHC class II molecule.

Referring now to FIG. 4. Having demonstrated that the CD4 T cell clones were MHC class II restricted, experiments were carried out to determine if the CD4 co-receptor was important during activation of CD4 T cells by infected epithelial cells. C57epi.1 epithelial cells were pretreated with 10 ηg/ml IFN-γ for 14 h, infected with 3 IFU/cell for 18 h; then treated with mitomycin C, harvested and used as T cell targets. 50,000 CD4 T cell clone cells were co-cultured with 50,000 mock-infected or infected epithelial cells in the presence of tetracycline, and either 10 μg/ml isotype control antibody or 10 μg/ml anti-CD4 monoclonal antibody GK1.5. Culture supernatants were collected after 24 h and analyzed for IFN-γ content by ELISA. Aggregate data from two independent experiments±SEM; ***=p value<0.001 comparing anti-CD4 treatment to the antibody control. Infected epithelial targets were prepared by pretreating C57epi.1 monolayers with IFN-γ, then mock-infecting or infecting them with *C. muridarum* for 18 h. 18 h post-infection the cell monolayers were harvested and co-cultured with the CD4 T clones in the presence of an anti-CD4 monoclonal antibody (GK1.5) or control antibody. 24 h later culture supernatants were harvested and assayed for IFN-γ content by ELISA to measure T cell activation. Engagement of the CD4 co-receptor by epithelial MHC class II was critical for activation of all three CD4 T cell clones.

4. *Chlamydia*-Specific CD4 T Cell Clones do not Recognize Infected Epithelial Cells Until 12 or More Hours Post-Infection.

The timing of CD4 T cell recognition of infected epithelial cells during the course of infection is unknown. Bone marrow-derived macrophages pulsed with heat-killed *C. muridarum* and fixed at ~2 h intervals showed near maximal activation of *Chlamydia*-specific CD4 T cells by 4 h post-antigenic pulse (Su and Caldwell, 1995). To determine when CD4 T cells could recognize infected epithelial cells over the time course of infection, C57epi.1 monolayers were untreated or pretreated with IFN-β plus IFN-γ prior to infection (mock infection=time 0). C57epi.1 cells were pretreated with both IFN-β and IFN-γ because the reproductive tract epithelium of wild type mice is likely exposed to IFN-β and IFN-γ during *C. muridarum* genital tract infections (addressed in more detail in a subsequent section). Interferon treatments and infections were staggered such that all targets were ready at the same time. Monolayers were harvested and co-cultured with CD4 T cell clones in the presence of tetracycline. Tetracycline served to block progression of the *C. muridarum* infection and additional protein synthesis, the source of the *Chlamydia* polypeptides that serve as T cell antigens. 36 h later culture supernatants were harvested to measure IFN-γ, and experimental wells pulsed with $^3$H thymidine to measure proliferation. CD4 T cell clones did not proliferate to infected epithelial cells at any time point during the course of infection; all clones proliferated to *Chlamydia*-pulsed irradiated splenocytes (data not shown).

Figure 5A:
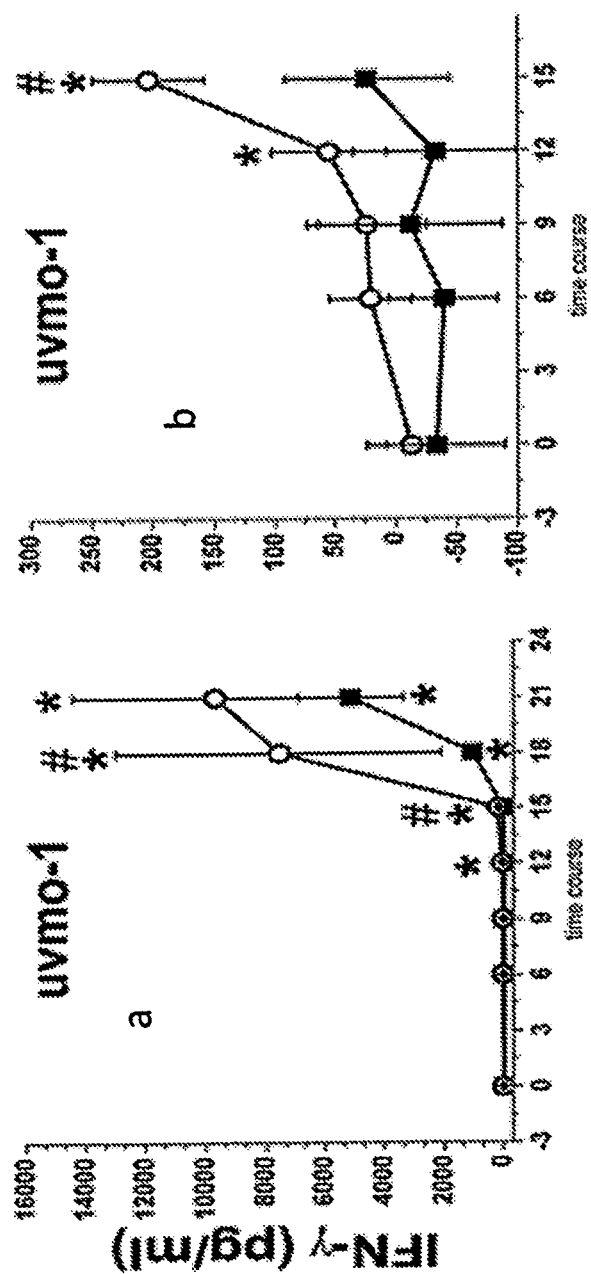
FIG. 5A. Graph of IFN-γ versus time determined for uvmo-1 cells: panel a, is the complete time course; panel b, is the early portion of the time course. Illustrating CD4 T cell clone unmo-1, recognition of infected epithelial cells over the time course of infection.
Figure 5B:
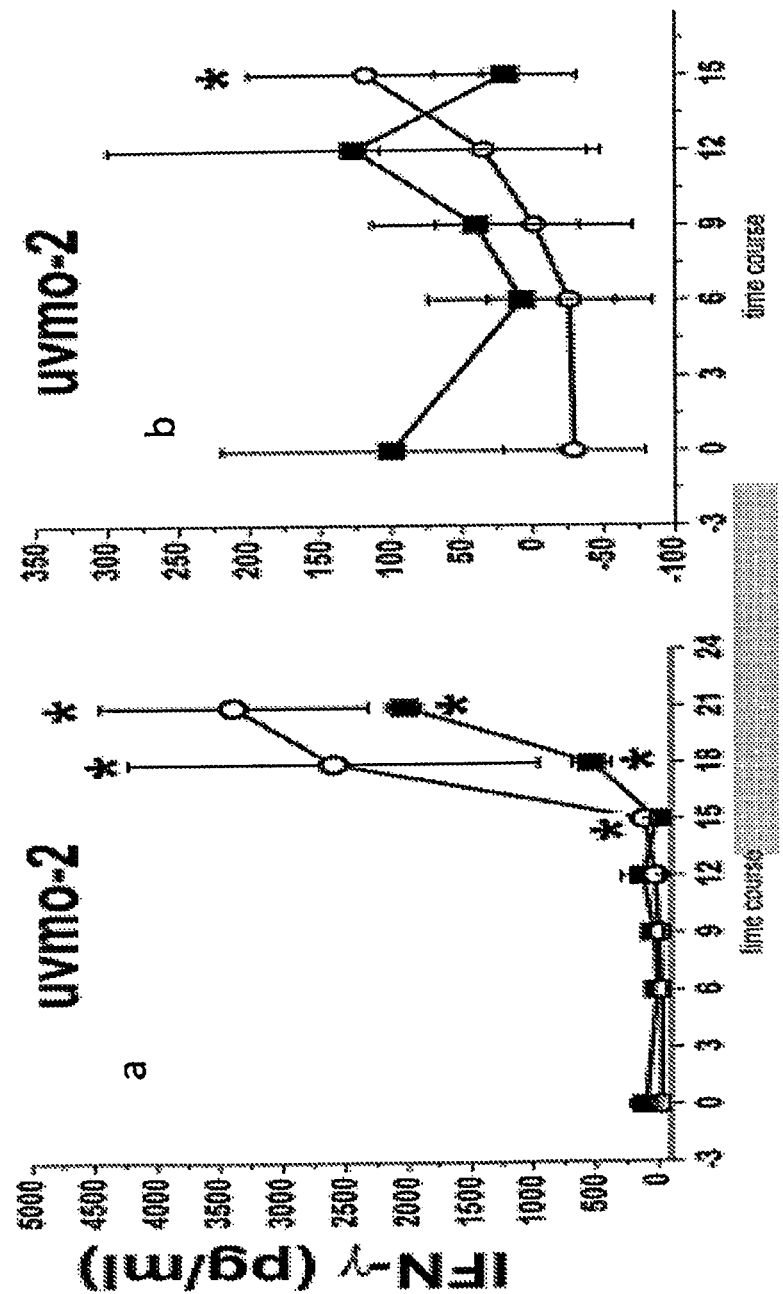
FIG. 5B. Graph of IFN-γ versus time determined for uvmo-2 cells: panel a, is the complete time course; panel b, is the early portion of the time course. Illustrating CD4 T cell clone unmo-2, recognition of infected epithelial cells over the time course of infection.
Figure 5C:
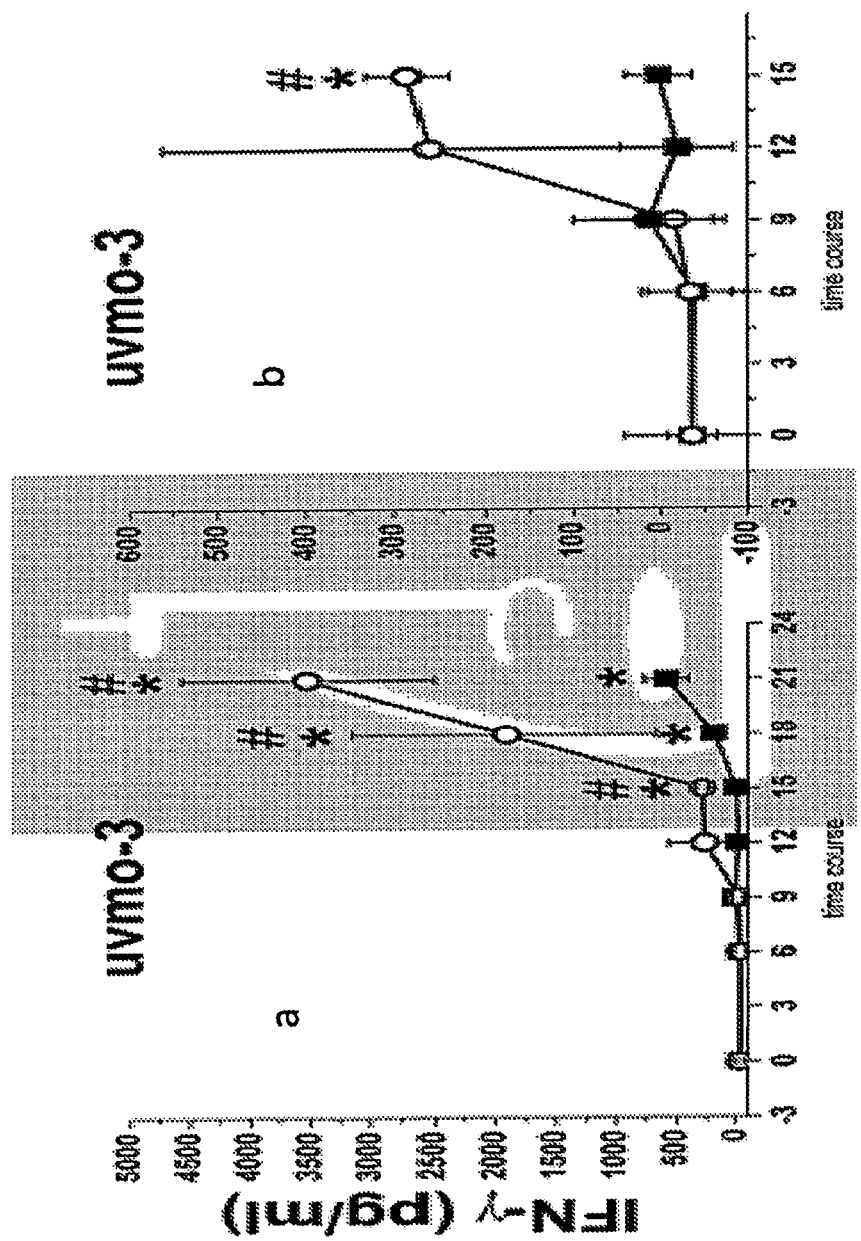
FIG. 5C. Graph of IFN-γ versus time determined for uvmo-3 cells: panel a, is the complete time course; panel b, is the early portion of the time course. Illustrating CD4 T cell clone unmo-3, recognition of infected epithelial cells over the time course of infection.

Referring now to FIG. 5. Uvmo-1,-2,-3 were activated by infected epithelial cells as measured by production of IFN-γ. CD4 T cell clone recognition of infected epithelial cells over the time course of infection; influence of interferons on recognition. C57epi.1 epithelial monolayers were untreated (solid squares) or pretreated with IFN-β/γ (100 units per ml/10 ηg per ml; open circles) for 14 h, then infected with 3 IFU *C. muridarum* per cell in staggered fashion over a time course of infection going from 0 h (mock-infected) to 21 h. Infected monolayers were treated with mitomycin C just prior to harvest. 50,000 CD4 T cell clone cells were co-cultured with 50,000 epithelial targets for 36 h in the presence of tetracycline (10 μg/ml); culture supernatants were collected and analyzed for IFN-γ content by ELISA. CD4 clone uvmo-1. First column=complete time course from 0 h-21 h. Second column=time course from 0 h-15 h plotted on a more sensitive IFN-γ scale to visualize early low level IFN-γ production. Aggregate data from two experiments±SEM; *=p value<0.05 comparing each time point within a treatment (untreated or IFN-β/γ) to its time 0 h (mock-infected); #=p value<0.05 comparing IFN-β/γ pretreated to untreated epithelial cells at each time point>0 h For two of the three CD4 clones pretreatment of the epithelial monolayer with IFN-β/γ improved T cell activation compared to untreated monolayers, as measured by IFN-γ production. Improved T cell activation could represent either increased engagement of the T cell receptor due to more MHC class II antigen complexes on the epithelial cells surface, or changes in epithelial accessory molecules that augment the TCR signal. Plotting the data with a smaller IFN-γ scale allows visualization of the earliest recognition events (FIG. 5 Early events, left sides). For CD4 T cell clone uvmo-1 pretreatment of the epithelial monolayers with IFN-β/γ moved recognition from ~18 h in the untreated state to ~12 h with interferon pretreatment (FIG. 5A.); CD4 clones uvmo-2 (FIG. 5B.) and uvmo-3 (FIG. 5C.) recognition advanced from ~18 h to ~15 h post-infection. These experiments show that input antigen alone was not sufficient for CD4 T cell recognition as infection had to progress for at least 12 h (before addition of tetracycline) to generate a CD4 T cell recognizable target. Interferon pretreatment improved both CD4 T cell activation and recognition, though the magnitude of these effects varied by CD4 T cell clone.

5. IFN-β Augments Epithelial Activation of CD4 T Cells Clones, but Antagonizes IFN-γ by Blunting up Regulation of MHC Class II.

The *Chlamydia* pathogenesis knockout mouse literature shows contrasting roles for type 1 and type 2 interferons during clearance of genital tract infections. As a broad generalization, type 2 interferon (IFN-γ) makes a positive contribution to clearance (Darville, et al., Infect Immun, 69:3556-3561; 69:7419-7424, 2001), while type 1 interferons (IFN-α/β) have a negative effect recently documented in the IFNAR1 knockout mouse (Nagarajan, et al., 2008). Physiologic levels of IFN-γ have been documented in the genital secretions of *Chlamydia*-infected humans (Arno, et al., 1990) and mice (Darville, et al., Infect Immun 69:7419-7424, 2001). IFN-β is secreted by infected epithelial cells (Derbigney, et al., 2005, Derbigney, et al., 2007, Johnson, R. M., 2004), and IFN-β is detectable in the genital secretions of mice infected vaginally with *C. muridarum* (W.A. Derbigny personal communication). The presence of type 1 and type 2 interferons in genital secretions during infection makes it likely that many reproductive tract epithelial cells are exposed to interferons prior to becoming infected with *Chlamydia*. The role of type 1 and type 2 interferons in vitro using the reproductive tract epithelial cell line disclosed herein and CD4 T cell clones was examined One working hypothesis is that untreated epithelial cells mimic the interferon milieu of early infection (low interferon levels), IFN-β pre-treated cells mimic IFN-γ knockout mice (IFN-β with no IFN-γ), IFN-γ pretreated cells mimic IFNAR1 knockout mice (IFN-γ with no functional IFN-α/β), and that IFN-β/γ pretreated cells mimic wild type mice.

C57epi.1 cells were untreated or pretreated for 14 h with IFN-β, IFN-γ, or IFN-β/γ, then infected with *C. muridarum*. 18 h post-infection the epithelial monolayers were harvested and co-cultured with CD4 T cell clones in the presence of tetracycline. 24 h later culture supernatants were harvested and analyzed for IFN-γ to score T cell activation (FIG. 6.).

Figure 6A:
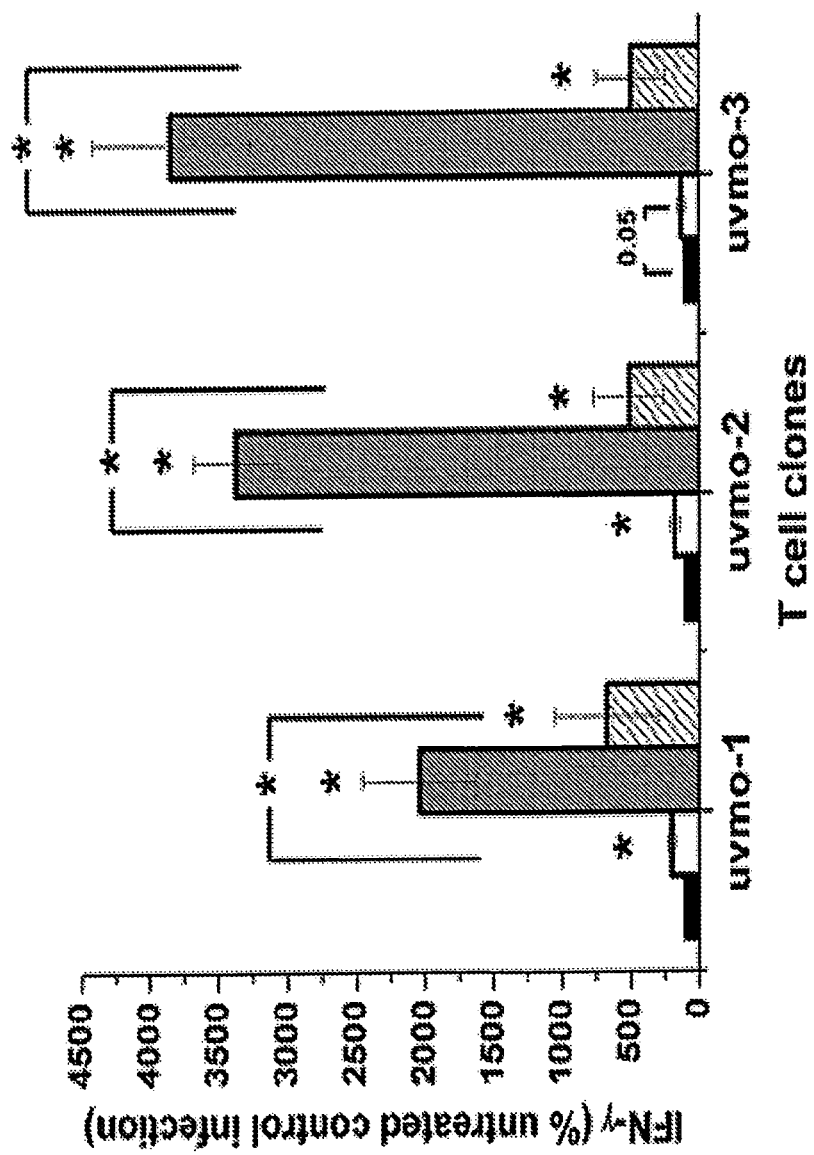
FIG. 6A. IFN-β and IFN-γ pretreatment of epithelial cells had different effects on epithelial MHC class II expression and activation of various CD4 T cell clones. Media (black bars), IFN-β (white bars), IFN-γ (gray bars), IFN-β/IFN-γ (hatched bars).
Figure 6B:
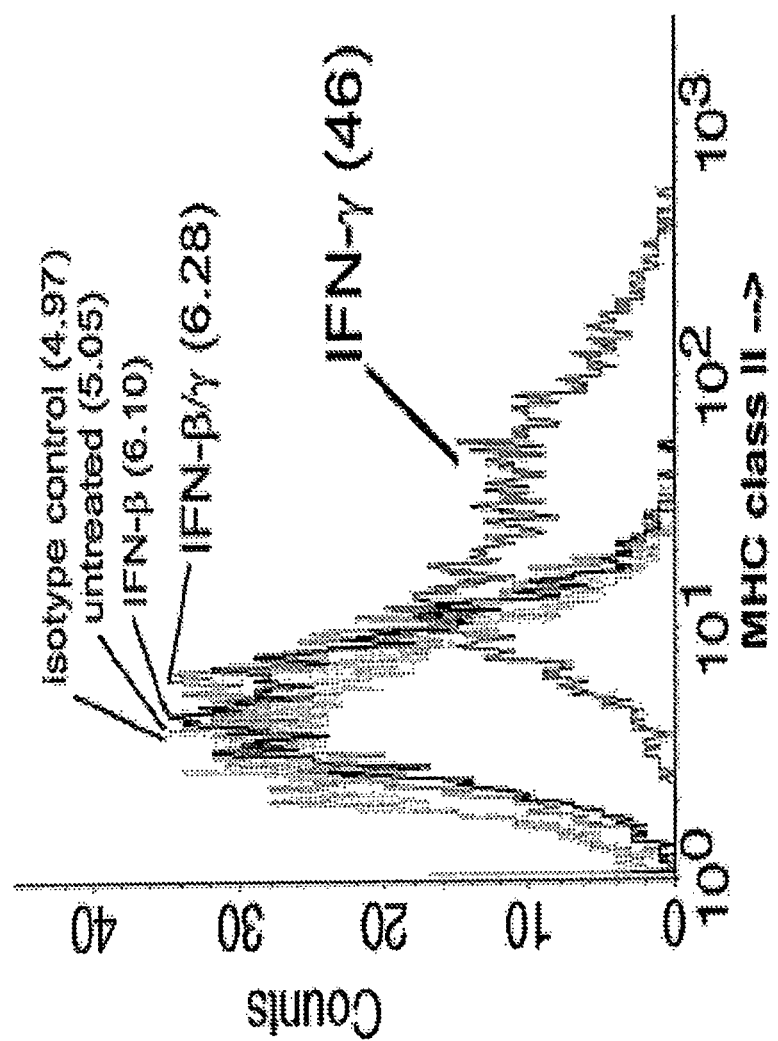
FIG. 6B. MHC class II expression in untreated 18 h-infected C57epi.1 cells versus 14 h IFN-β, IFN-γ, and IFN-β/γ pretreatment followed by infection for 18 h.

Referring now to FIG. 6A. For all three CD4 T cell clones, IFN-β pretreatment of epithelial cells prior to infection augmented CD4 T cell activation compared with untreated infected epithelial cells, with the caveat that the comparison for uvmo-3 had a p value=0.050. C57epi.1 epithelial cells were untreated or pretreated with IFN-β (100 units/ml), IFN-γ (10 ηg/ml), or IFN-β/γ (100 units/10 ηg per ml) for 14 h, infected with 3 IFU *C. muridarum* per cell for 18 h, treated with mitomycin C just prior to harvest and use as targets. 50,000 CD4 T cell clone cells were co-cultured with 50,000 epithelial cells in the presence of tetracycline (10 μg/ml); culture supernatants were collected at 24 h and analyzed for IFN-γ content by ELISA. Black bars=no pretreatment; white bars=IFN-β pretreatment; grey bars=IFN-γ pretreatment; grey hatched bars=IFN-β/γ pretreatment. Aggregate data from three independent experiments±SEM; *=p value<0.05 comparing each condition to untreated cells, and IFN-β/γ cells to IFN-β cells (floating bracket). IFN-γ pretreatment impressively augmented T cell activation beyond that seen with IFN-β for all three CD4 clones; and interestingly, co-pretreatment with IFN-γ and IFN-β blunted IFN-γ augmentation, though co-pretreatment was still better at activating the CD4 T cell clones than was IFN-β pre-treatment alone. These results can be explained by affects of type 1 and type 2 interferons on expression of epithelial MHC class II.

In order to investigate the effects of type 1 and 2 interferons on inducible epithelial cell surface MHC class II expression in the setting of *C. muridarum* infection, the same protocol that was used for preparing the infected epithelial targets as described above. Briefly, C57epi.1 cells were untreated, or pretreated with IFN-β, IFN-γ, or IFN-β/γ, prior to infection. 18 h post-infection the epithelial monolayers were harvested, stained for MHC class II, and analyzed by flow cytometry (approximating the conditions in panel A), these results are presented in FIG. 6B. Numbers in parentheses are the mean fluorescence values in arbitrary units for each experimental condition. Data shown are representative of two independent experiments. The levels of CD4 T cell activation correlated with the relative amount of epithelial cell surface MHC class II induced by the different interferon pretreatments; untreated<IFN-β<IFN-β/γ<<<IFN-γ. The relative cell surface levels of MHC class II correlates with the published *C. muridarum* clearance rate from interferon knockout mice: IFN-γ knockout (IFN-β pretreatment)<wild type (IFN-β/γ pretreatment)<<IFNAR1 knockout (IFN-γ pretreatment).

6. A Subset of CD4 T Cells that Efficiently Clears Genital Tract Infections Expresses the Genes Casd1 and Plac8.

Figure 7:
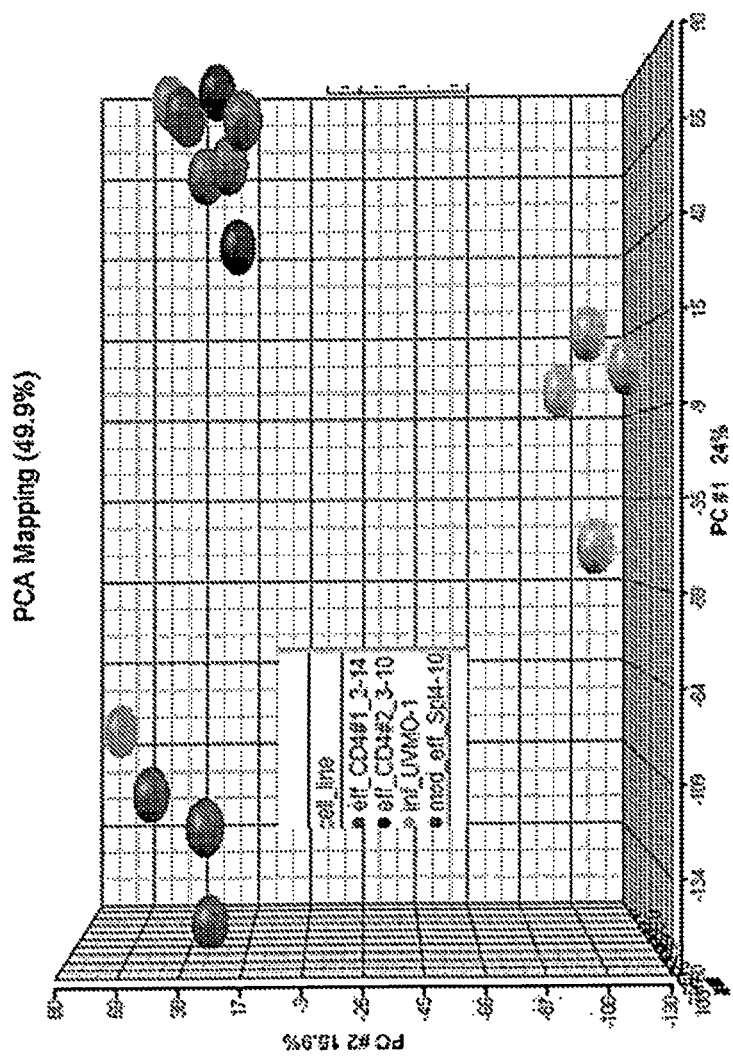
FIG. 7. A comparison of the gene expression pattern associated with the CD4 T cell clones: efficient (CD4#1_2_14); efficient (CD4#2_3_10); inefficient (inf_UVMO-1); and moderately efficient (mod_eff_Sp14-10).

Referring now to Table 2. A gene chip analysis was performed on four *Chlamydia*-specific CD4 T cell clones derived from mice that cleared a genital tract infection and are resistant to re-infection (immune). These mice have protective immunity that was generated during the response to the original infection. Accordingly, these mice provide a model for generating and accessing protective immunity by vaccination in humans. Referring now to FIG. 7. Both clones 2-14 and 3-10 herein otherwise referred to respectively, as uvmo-2 and uvmo-3, exhibit an excellent ability to control *Chlamydia* replication. These two clones also co-segregate in principle component analysis (PCA) demonstrating that they have very similar gene expression patterns. While, uvmo-1 (also referred to as uvmo-4), exhibits no ability to control *Chlamydia* and was deemed to be ineffective) and sp14-10 (which exhibits only an intermediate ability to control *Chlamydia*) map quite differently from one another and from clones 2-14 and 3-10. These results show that there is unique gene expression pattern associated with T-cells that are able to control *Chlamydia* replication in epithelial cells, which has previously been shown Igietseme et al to be a surrogate marker for protective immunity in mice.

Referring now to Table 2, the clone, designated as 'ineffective', is unable to control *Chlamydia* replication in epithelial cells in vitro; the clone designated as intermediate, does an ok job controlling *Chlamydia* but the mechanism for controlling replication (nitric oxide) is not likely relevant in humans; and the two clones, designated as 'effective x2", are excellent at controlling *Chlamydia* and their probable mechanism of action (Plac8) is relevant in humans. *Chlamydia*-specific T cell clones uvmo-1 (known as uvmo-4 in publication), sp14-10, 2-14 (known as uvmo-2 in publication), and 3-10 (known as uvmo-3 in publication) were derived from immune C57BL/6 mice that had previously cleared a genital tract infection with *Chlamydia muridarum*. The antigen presenting cell in culture for uvmo-1 and sp14-10 was irradiated splenocytes from immune C57BL/6 mice. The antigen presenting cell in culture for 2-14 and 3-10 was irradiated splenocytes from naïve C57BL/6 mice. The *Chlamydia* antigen for uvmo-1, 2-14, and 3-10 was ultraviolet irradiated *Chlamydia muridarum*. The antigen for clone sp14-10 was a *C. muridarum* infected cell lysates depleted of elementary bodies by centrifugation. For the microarray experiment, the four T cell clones were harvested at the end of their usual culture cycle, purified by histopaque 1083 centrifugation to remove debris from irradiated splenocyte APC, then cultured for 2.5 days in usual media supplemented with secondary mixed lymphocyte culture supernatant (15% vol/vol), recombinant IL-1a, IL-2, IL-6, IL-7, IL-15. On day 2.5 the media was aspirated off the adherent T cells, and then T cells lysed and total RNA isolated using the RNAeasy Kit with DNAse treatment (Qiagen) according the manufacturers protocol. The experiment was performed four times. Total RNA was delivered to the IU Center for Medical Genomics who performed the Affymetrix microarrays and data analysis. Referring now to FIG. 11, Plac8 is an antibacterial peptide that is common to mice and humans. Referring now to FIG. 7 and Table 2, expression of Casd1/Plac8 appears to be critical to mounting an immune response that is relevant to mice and humans. CasD1 and Plac8 are absent, or nearly so, in both the ineffective clone (−31.68 & −138.39 fold) and the intermediate clone (−35.14 & −171.602 fold). While there may be a very low level of CasD1 on the ineffective and intermediate T cell clones, it is relatively abundant on both of the effective clones as a 30-fold difference is essentially all versus none. Casd1 appears to be a protein of heretofore unknown function having either no or a very limited publication record.

TABLE 2

Summary of differences in gene expression measured with different T-cell clones.

| gene symbol | p-value (ineffective vs. intermediate) | Fold-Change (ineffective vs. intermediate) | p-value (ineffective vs. effective x2) | Fold-Change (ineffective vs. effective x2) | p-value (intermediate vs. effective x2) | Fold-Change (intermediate vs. effective x2) |
|---|---|---|---|---|---|---|
| Casd1 | 1.25E−01 | 1.11 | 1.58E−16 | −31.68 | 1.11E−16 | −35.1479 |
| Plac8 | 3.89E−02 | 1.24 | 2.33E−16 | −138.39 | 1.40E−16 | −171.602 |

7. The Mouse Gene Casd1 Shares About 95 Percent Identity with the Human Gene.

Figure 8:
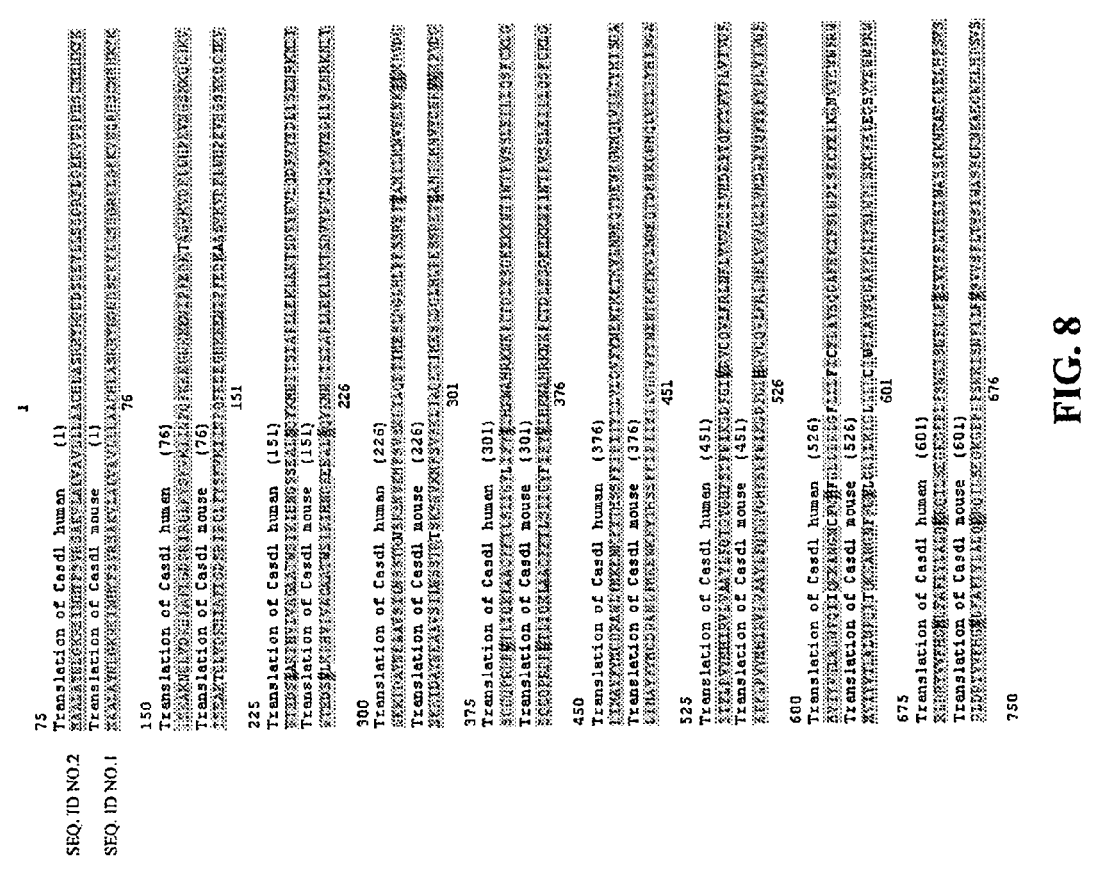

Referring to FIG. 8. A comparison of the proteins encoded by the mouse and human casd1 genes illustrates that the mouse and human proteins are highly conserved suggesting the importance of these proteins and likelihood that these proteins play the same or nearly the same role.

Referring now to FIG. 10, an analysis of the sequence of the Casd1 shows that it includes an extracellular domain a structural feature consistent with it its role in CD4 T cell mediated immunity. Referring now to FIG. 9, a portion of the mouse protein thought to comprise at least a portion of the extra-cellular domain of the protein was compared to its human equivalent. About 98.2% of the amino acids in this domain were conserved between the mouse and human forms and bout 95.5 percent of identical between the two protein sequences. These results suggest that this region plays the same important role in both humans and mice.

The presence of cell surface protein Casd 1 on the surfaces of T-cells isolated from animals that mount an effective immune response to *Chlamydia* or other bacterial or viral pathogens that infect target mammals via the epithelial cell layer, can be used to help control, diagnose and treat diseases such as *Chlamydia* by providing a method for identifying individual humans and animals that have mounted an immune response to either the pathogen or an antigenic portion of the pathogen or an analogue thereof.

Data generated using knockout mice are likely the most definitive with respect to understanding contributions of specific T-cell subsets to *Chlamydia* host defense. A seminal paper utilizing β2-microglobulin knockout mice (deficient in MHC class 1a, non-classical MHC class 1b, and CD1d), CD4 knockout mice, and MHC class II knockout mice has been broadly interpreted as demonstrating that only CD4 T-cells are important for clearing *Chlamydia* from the genital tract (Morrison et al., 1995). The authors' interpretation of their data was that MHC class II was absolutely required for clearance of *Chlamydia* from the reproductive tract. Mice deficient in β2-microglobulin (open circles), which are largely but not entirely CD8 deficient, cleared genital tract infections with approximately normal kinetics (a modest ~5 day delay in clearance; when compared to wild type control (closed circles). MHC class II-deficient mice showed no demonstrable clearance over 70 days (compared to wild type controls) (Morrison et al., 1995). Those data strongly support an unambiguous dominant role for CD4 T-cells in immune-mediated clearance, except that CD4 knockout mice cleared genital tract infections with near normal kinetics (~10 day delay in clearance) (Morrison et al., 1995). It took CD4 knockout mice 40 days to clear *C. muridarum* from the genital tract versus 30 days for wild type mice (Morrison et al., 1995). This discrepancy with respect to "CD4-only" host defense has been minimized as reflecting peculiarities of CD4 knockout mice (Rahemtulla, et al., 1994; Matechak, et al., 1996); the prevailing view is essentially that a fraction of CD8 T-cells in these mice are MHC class II-restricted and likely represent 'true' CD4 T-cells trapped in a 'CD8 T-cell body'. An alternative interpretation of the same data presented in Morrison et al., is that in the absence of 'true' CD4 T-cells a relatively infrequent population of MHC class II-restricted CD8 T-cells expands and mediates delayed clearance. One conclusion consistent with the data presented in Morrison et al., 1995, is that MHC class II-restricted CD8 T-cells are capable of clearing *C. muridarum*, though they are less efficient than 'true' CD4 T-cells due to impaired clonal expansion in the absence of CD4 T-cell help or a less robust mechanism of clearance. Accordingly, the CD4 knockout mouse data provides proof that *Chlamydia*-specific CD8 T-cells can be MHC class II-restricted because MHC class II knockout mice could not clear a genital tract infection, still the overall contribution of these cells to *Chlamydia* host defense in wild type mice is unknown.

Casting further doubt on a "CD4 only" interpretation of the study by Morrison et al. is another important study showing that β2 microglobulin-deficient mice (H-$2^b$) mounted a robust CD8 T-cell response to H-$2^d$ kidney allografts that was equal to that of wild type mice in spite of their paucity of CD8 T-cells at baseline. β2 microglobulin-deficient mice rejecting H-$2^d$ kidney allografts had a paucity CD8 T-cells in the spleen, with a robust recipient CD8 T-cell infiltrate in the kidney allograft (Mannon, et al., 1995). One reasonable conclusion to be drawn from these data is that β2 microglobulin-deficient mice are not completely deficient in functional CD8 T-cells. The lack of splenic reconstitution with CD8 T-cells in β2 microglobulin-deficient mice during allograft rejection suggests that these alloreactive CD8 T-cells were expanding outside the systemic immune compartment. By way of explanation and not of limitation, and without intending to be bound by any one theory or hypothesis, one interpretation consistent with this data is that this expansion was occurring within the allograft stroma based on work by Richards et al. (Richards, et al., 2003). And that the responding CD8 T-cells included MHC class II-restricted clones, as β2 microglobulin-deficient mice lack cell surface MHC class I molecules required for MHC class I driven CD8 differentiation during thymic selection (Hashimoto, et al., 1996).

The immunology literature includes numerous examples of MHC class II-specific alloreactive CD8 T-cell clones isolated from wild type mice without manipulations to selectively enrich for them (see e.g., Vidovic, et al., 1981; Miller and Stutman, 1982; and Nakayama, E., 1982). In MHC class I and II mismatched mixed lymphocyte reactions, roughly 10% of alloreactive CD8 T-cells are specific for MHC class II antigens (Golding and Singer, 1985). These MHC class II-specific CD8 T-cells include clones that recognize alloantigen directly (MHC class II-restricted) and indirectly (MHC class II peptides presented on MHC class I molecules) (Shinohara, et al., 1988). Of particular interest is that two prominent laboratories have isolated panels of *Chlamydia*-specific CD8 T-cell clones from patients with a history of *Chlamydia* genital tract infection (Matyszak and Gaston, 2004; Gervassi, et al., 2033). Remarkably, the majority of these human CD8 T-cell clones were "MHC-unrestricted". The 'unrestricted' *Chlamydia*-specific CD8 T-cells recognized infected targets at an earlier time point post-infection (8 h) than did MHC class I-restricted CD8 T-cell clones (24 h). The "unrestricted" CD8 clones were not CD1-restricted based on blocking antibody experiments (Matyszak and Gaston, 2004). Recognition of infected targets by "unrestricted" CD8 T-cell clones was inhibited by lactacystin, a proteosome inhibitor that blocks MHC class 1a & 1b peptide processing. However, these results do not rule out chaperone-mediated autophagy, an MHC class II antigen processing pathway that is also lactacystin sensitive (Crotzer and Blum, 2005). Neither study directly investigated the possibility that the CD8 T-cell clones were MHC class II-restricted by using, for example, HLA-defined APC or blocking monoclonal antibodies specific for MHC class II. Additionally, neither study appears to have characterized "unrestricted" αβTCR CD8 T-cells, or report on its role in host defense at the epithelial interface.

One approach to investigating *Chlamydia*-specific T-cell interactions with infected epithelial cells is to isolate antigen-specific T-cells from immune mice that had cleared primary and secondary genital tract *C. muridarum* infections using infected epithelial cells as APC. This approach was tried without success. Primary T-cell cultures on infected epithelial cells showed specific lysis of infected monolayers and IFN-γ release, but T-cell expansion failed during sequential passage.

In view of these unfortunate results and in order to investigate T-cell-epithelial cell interactions, it was necessary to develop an alloantigen model based on the bm1 and bm12 experimental transplantation model (Vallera, et al., 1994; Sprent, et al., 1986). Further investigations using the later approach revealed that infected epithelial cells induced anergy in alloreactive CD8 T-cells.

Oviduct epithelial cell lines from bm1 mice (designated Bm1.11) and bm12 mice (designated Bm12.4) were developed. The bm1 mice are identical to C57BL/6 mice except for a 3 amino acid change in the H-2K MHC class I molecule. bm12 mice are identical to C57BL/6 mice except for a 3 amino acid change in the MHC class II beta chain. On that basis, C57BL/6 mice reject bm1 tissue via CD8 T-cells (MHC class I-restricted) and reject bm12 tissue via CD4 T-cells (MHC class II-restricted). As semi professional APC, oviduct epithelial cells cannot prime naïve T-cells. Therefore in order to study effector T-cell populations C57BL/6 mice were primed with full thickness skin grafts from either bm1 or bm12 mice. The donor skin grafts were rejected within two weeks, and the recipient mice then rested for 3 months. Memory splenocytes from mice primed with bm1 skin grafts were plated on Bm1.11 epithelial cells; memory splenocytes from mice primed with bm12 skin grafts were plated on Bm12.4 epithelial cells.

Figure 13:
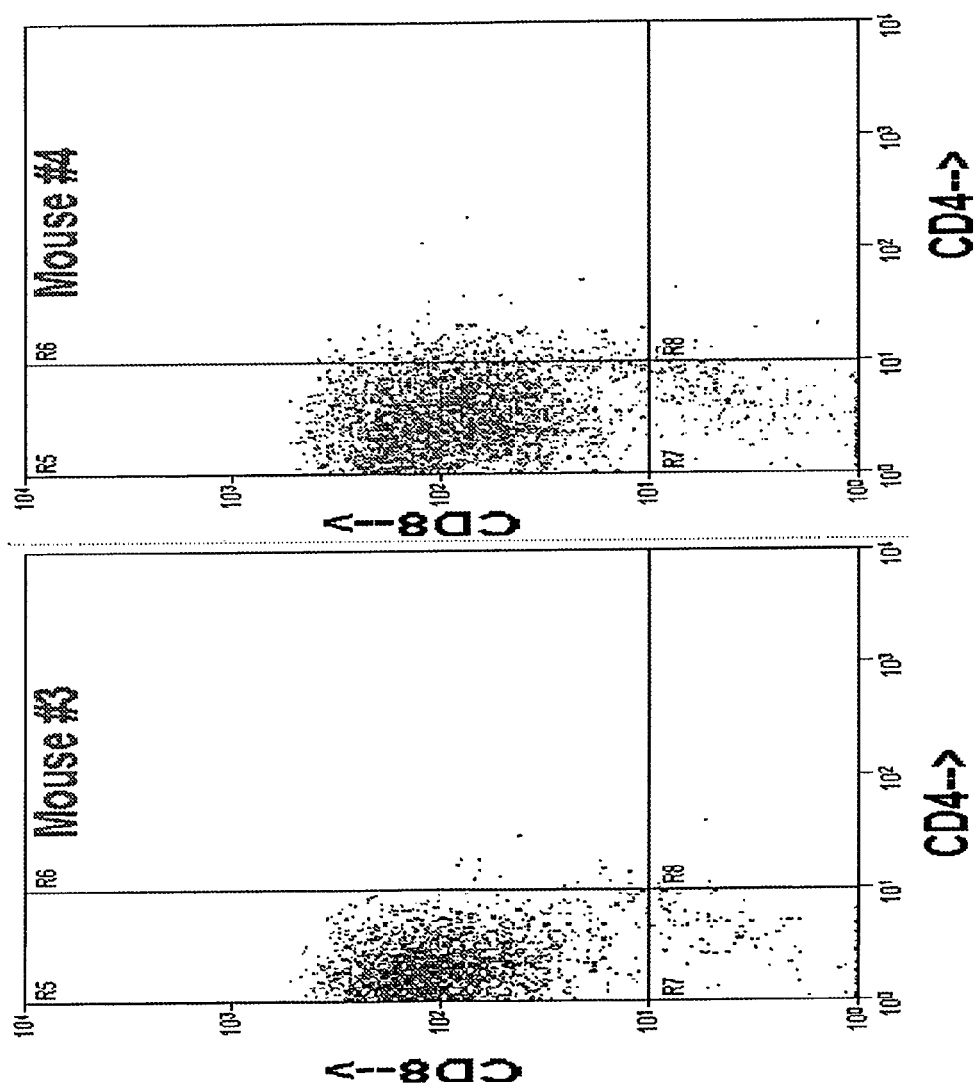
FIG. 13. Plot showing the phenotype of alloactive T-cells derived on Bm12.4 epithelial monolayers for 2 different mice; m#3 left, m#4 right.

Cultures of bm1-primed C57BL/6 splenocytes plated on Bm1.11 epithelial cells yielded exclusively CD8 alloreactive T-cells. Those cultures were limiting-diluted to derive a bm1-specific CD8 T-cell clone designated CD8bm1 that is maintained on Bm1.11 epithelial cell feeder layers without irradiated splenocytes. Quite unexpectedly, instead of the expected CD4 T-cells, cultures of bm12-primed C57BL/6 splenocytes plated on Bm12.4 epithelial cells also yielded exclusively CD8 alloreactive T-cells. These culture conditions were repeated with two additional bm12-primed C57BL/6 mice (Mouse #3 & 4). Referring now to FIG. 13, after the third passage on Bm12.4 epithelial cells, the resulting polyclonal T-cell populations were stained for CD4 and CD8. As in the first experiment, 100% of the T-cells were CD8+CD4$^{neg}$. These cultures were limiting diluted to derive two bm12-specific CD8 T-cell clones designated CD8bm12-1 and CD8bm12-2 that are maintained on Bm12.4 epithelial cell feeder layers without irradiated splenocytes.

TABLE 3

MHC Haplotypes

| Mouse Strain (Cell line) | K | I-A | D |
|---|---|---|---|
| B6.C-H2$^{bm1/ByJ}$ (Bm1.11) | bm1 | b | b |
| B6.C-H2$^{bm12/KhEWg}$ (Bm1.11) | b | bm12 | b |

Figure 14:
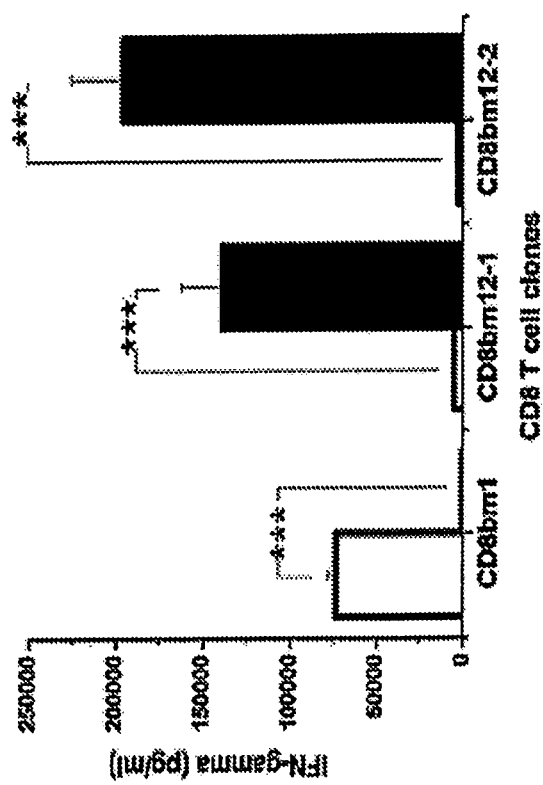
FIG. 14. Bar graph illustrating IFN-γ measured for different T-cell clones that were co-cultured for 48 hours on different epithelial monolayers. Clear bars, Bm1.11 targets; black bars, Bm12.4 targets; pvalue<0.001.

T-cell clone specificity is shown in FIG. 14. Still referring to FIG. 14 which illustrates the specificity of alloreactive CD8 T-cells. Briefly, T-cell clones were co-cultured for 48 h on either Bm1.11 or Bm12.4 epithelial monolayers. Culture supernatants were harvested and IFN-γ quantified by ELISA. Clear bars=Bm1.11 targets; black bars=Bm12.4 targets, with a pvalue<0.001. Data are representative of three independent experiments. The CD8bm1 differs dramatically from CD8bm12-1 & CD8bm12-2 in its ability to kill allo-epithelial cell targets. CD8bm1 kills efficiently allo-epithelial cell targets while CD8bm12-1 and CD8bm12-2 are not cytolytic in short term assays (data not shown). Further testing showed that none of the T-cell clones recognized syngeneic bone marrow-derived macrophages pulsed with allo-epithelial cell ghosts (data not shown); a result consistent with direct allorecognition. Using a bm12 transplant rejection model that should have strongly favored derivation of alloreactive CD4 T-cells, only MHC class II-specific CD8 T-cell lines could be isolated. Accordingly, in view of these unexpected results it appears that T-cell biology at the epithelial interface likely differs from the immunobiology of mixed-lymphocyte-reactions.

Referring now to Table 4, in order to gain further insight into this unusual T-cell biology, Affymetrix murine GeneChip microarrays were used to identify transcripts that differed between the prototypic bm1-specific CD8bm1 T-cell clone and the novel bm12-specific CD8bm12-1 clone. That analysis identified at least three notable genes (CD7, PKCζ, & IL-18 receptor) that differed significantly between CD8bm1 and CD8bm12-1 T-cells (see Table 1). The CD7 and PKCζ mRNA differences between CD8bm1 and CD8bm12-1 T-cells were confirmed by semi quantitative RT-PCR, and have remained stable for 1+ years in culture. RT-PCR confirmation of the IL-18R result is pending. A hypothesis consistent with these results is that PKCζ and IL-18R identify unique CD8 T-cell subsets capable of interacting with oviduct epithelial cells.

TABLE 4

Results of Affymetrix Microarray Analysis

| nRNA | Fold Change CD8bm12-1: CD8bm1 | Welsh T-test (log Signal) p Values |
|---|---|---|
| CD7 | +181.5 | 0.0001 |
| PCKζ | +36.55 | 0.00131 |
| IL-18 receptor | +311.06 | 0.0005 |

CD7 is a member of the immunoglobulin superfamily that is expressed on the large majority of human CD8 and CD4 T-cells. In human peripheral blood, CD8 T-cells can be divided into three subsets by CD7 levels; high (70%)—low (28%)—negative (1-2%). Phenotypic and functional analysis showed that CD7high CD8 T-cells were either naïve cells or effector memory cells that were perforin negative. CD7low and negative CD8 T-cells divided into two mutually exclusive subsets; a perforin+ subset with minimal cytokine production, and a cytokine producing (IFN-γ) subset without perforin. Levels of CD7 that characterized each subset were stable in vitro. (Aandahl, et al., 2003). Human CD4 T-cells are either CD7 positive (81%) or negative (19%) (Reinhold, et al., 1993), with an increasing CD7negative fraction with increasing age (Kukel, et al., 1994). CD7$^{neg}$ CD4 T-cells have a memory phenotype. Little is known about CD7 T-cell subsets in mice as there are no murine CD7-specific antibody reagents available for flow cytometry. CD7 knockout mice appeared to have normal numbers and subsets of peripheral T-cells, though knockout mice had a mild defect in cytolysis and TNFα secretion (Bonilla, et al., 1997). The latter may account for improved survival in CD7 knockout mice challenged with LPS (Sempowski, et al., 1999). CD7 binds extracellular galectin-3 causing T-cell apoptosis (Fukumori, et al., 203); Galectin-3 is expressed by mucosal epithelial cells. It is reasonable to hypothesize that T-cells lacking CD7 have a survival advantage during interactions with *Chlamydia*-infected epithelial cells. The role of CD7$^-$ versus CD7$^{neg}$ CD4 and CD8 T-cells in host defense is largely unknown because manipulation of human subjects is not possible and the necessary CD7 antibody reagents do not exist to perform these studies in mice.

Stable T-cell clone-specific expression of PKCζ suggests an alternative T-cell lineage and T-cell biology that is unique to MHC class II-restricted CD8 T-cells. The role of PKCζ in "CD8zeta" cells is not obvious based on the existing literature. In B cells, PKCζ is a Ca$^{++}$-independent major signal transduction molecule for the immunoglobulin receptor, while the T-cell receptor uses Ca$^{+-}$ dependent PKCθ. In PKCζ transfected Jurkat CD4 T-cells, PKCζ participates in signaling through NFAT (San-Antonio, et al., 2002). PKCζ also plays roles in signal transduction for diverse cytokine receptors including IL-1R and TNFR1 (Baier, G., 2003). There are no definitive data addressing the role of PKCζ in CD8 T-cells, and little or no data (negative or positive) addressing the role of PKCζ as a biomarker for T-cell subsets. Up regulated PKCζ expression may reflect a Ca++ independent signaling pathway that compensates for loss of the CD8-lck co-receptor signal for MHC class II restricted CD8 T-cells, as these T-cells would lack a co-receptor signal through either CD4 (not expressed) or CD8 (not engaged within the immunologic synapse). The IL-18 receptor high phenotype, the microarray data suggests that CD8zeta T-cells may preferentially utilize IL-18; an important cytokine for mucosal immunity (Staats, et al., 2001) and CD8 T-cell survival (Li, et al., 2007) known to be released by *Chlamydia*-infected epithelial cells (Lu, et al., 2000).

Figure 15A:
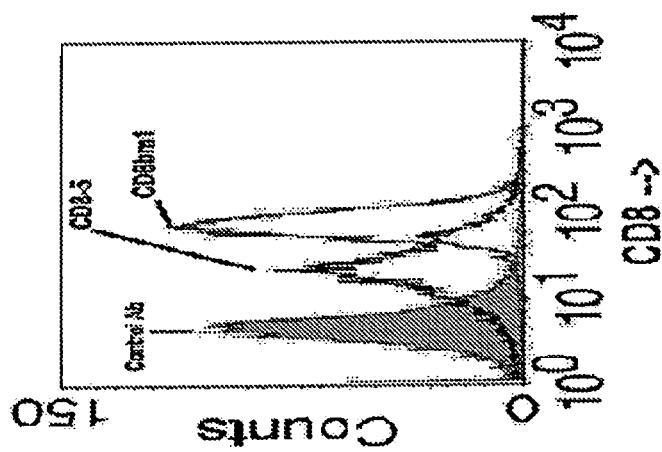
FIG. 15A. Flow cytometry data collected by measuring CD8 levels in alloreactive T-cell clone CD8bm1 and the *Chlamydia*-specific CD8 T-cell clone CD8-5. Background staining levels indicated by control antibody.
Figure 15B:
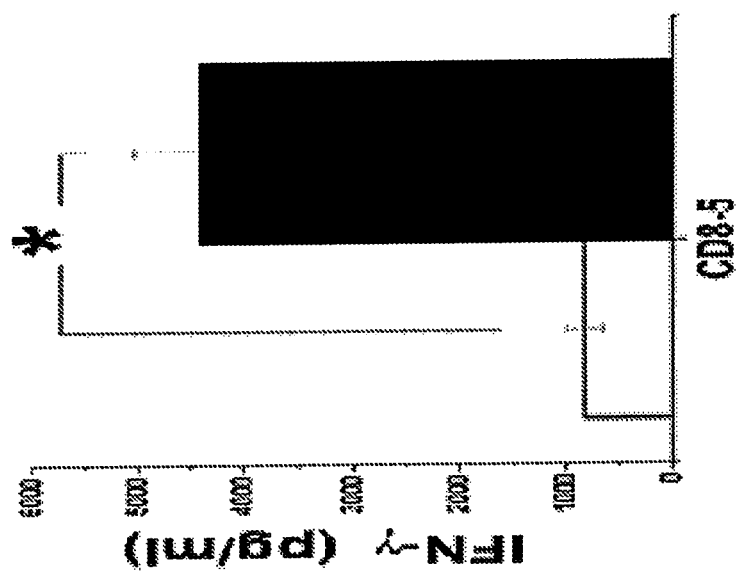
FIG. 15B. Graph of IFN-γ (pg ml$^{-1}$) produced by CD8-5 cells that were co-cultured with either un-infected C57BL/6 oviduct epithelial cells (clear) or infected C57BL/6 oviduct epithelial cells 18 h post infection with 5 IFU of *C. muridarum* per cell.

A panel of *Chlamydia*-specific CD4 T-cell clones were derived from immune mice lymph nodes and spleen using UV-inactivated-*C. muridarum*-pulsed naïve splenocytes as APC. The polyclonal T-cell cultures created were 100% CD4 T-cells. A hypothesis tested using those cells is that an alternative culture system based on immune Ig-receptor-bearing APC may utilize cross-presentation pathways to generate more CD8 T-cell epitopes and promote greater expansion of CD8 T-cells (Regnault, et al., 1999). Activating lymphocytes from immune mice with immune-irradiated splenocytes pulsed with elementary body-depleted-infected-epithelial-cell lysates (soluble *Chlamydia* antigens) yielded polyclonal T-cell populations with small but readily detectable CD8 T-cell populations (3-10%). Immune-irradiated splenocytes pulsed with UV-inactivated-*C. muridarum* also expanded a small but detectable CD8 T-cell population (~1%). CD4 T-cells from those polyclonal populations were selectively depleted using magnetic bead technology. The remaining T-cell populations were cloned by limiting dilution to derive three "UV-*C. muridarum*" CD8 T-cell clones and four "soluble antigen" CD8 T-cell clones. Referring now to FIG. 15A, the majority of the *Chlamydia*-specific CD8 T-cells have significantly lower levels of cell surface CD8 than the alloreactive CD8bm1 T-cell clone, e.g. T-cell clone CD8-5, while CD38 levels are similar (data not shown). In humans, CD8low T-cells are a CD28neg subset comprising ~2% of peripheral blood CD8 T-cells. The human CD8low T-cell subset includes EBV-specific clones (Trautmann, et al., 2003). The *Chlamydia*-specific CD8 clones tested herein specifically recognized infected C57BL/6 oviduct epithelial cells over uninfected controls, and recognized UV-*C. muridarum*-pulsed immune syngeneic C57BL/6 splenocytes (data not shown).

In order to quickly map the MHC class II-restriction of the CD8 T-cell clones available mice and approved animal protocols were used. In these experiments the CD8 T-cell clones were activated by UV-*C. muridarum*-pulsed immune-irradiated bm12 and C57BL/6 splenocytes. This is not a definitive mapping protocol as bm12 mice differ from C57BL/6 mice by only 3 amino acids in the MHC class II beta chain. And it is possible that MHC class II-restricted T-cell clones from C57BL/6 mice (I-A$^b$) could still 'see' antigen in the context of I-A$^{bm12}$. To account for this possibility a small panel of *Chlamydia*-specific CD4 T-cell clones in the mapping assays were included in the assay. Irradiated-immune-splenocyte APCs pulsed with UV-inactivated *C. muridarum* also release IFN-γ (without expanding), adding an additional level of complexity to these assays. Within an individual experiment it is important that the irradiated-immune-splenocyte cytokine response to UV-*C. muridarum* be similar between bm12 and C57BL/6J irradiated splenocytes in order to simplify interpretation of the data. None of the T-cell clones secreted detectable IFN-γ to naïve bm12 or C57BL/6J irradiated splenocytes; i.e. they do not recognize self or the bm12 alloantigen (data not shown).

Figure 16B:
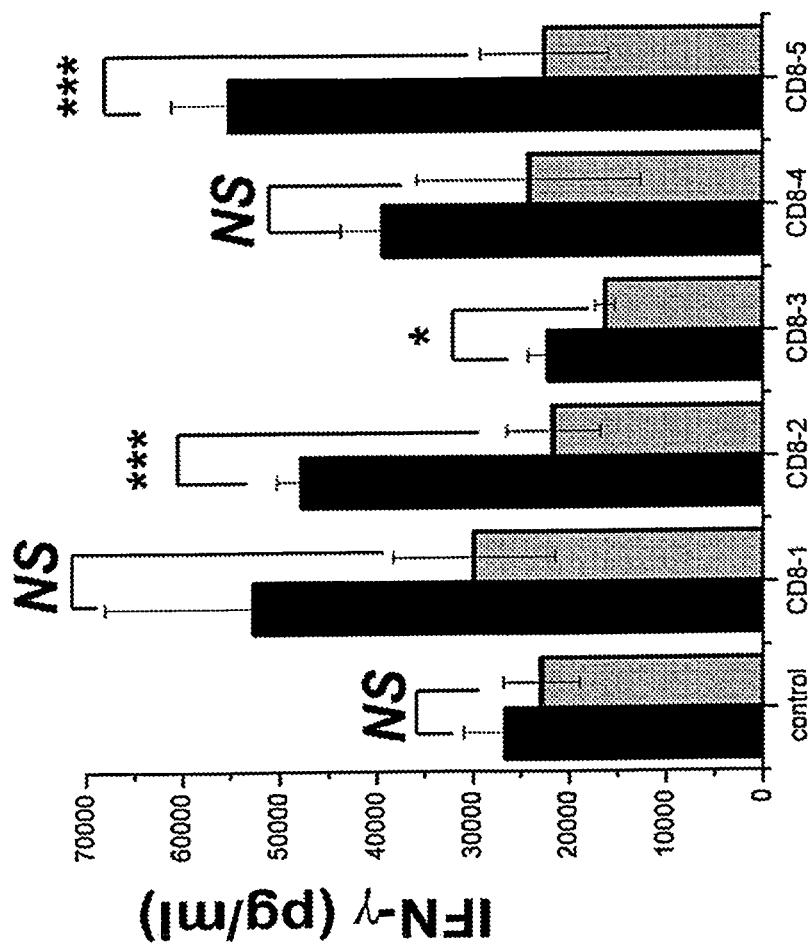
FIG. 16B. Graph of IFN-γ (pg ml$^{-1}$) produced by different CD8 T-cell clones co-cultured with ultraviolet-light-inactivated *C. muridarum* pulsed syngeneic C57BL/6J (H-2 I-A$^b$; black bars) or bm12 (H-2 I-A$^{bm12}$; gray bars) irradiated splenocytes.
Figure 17:
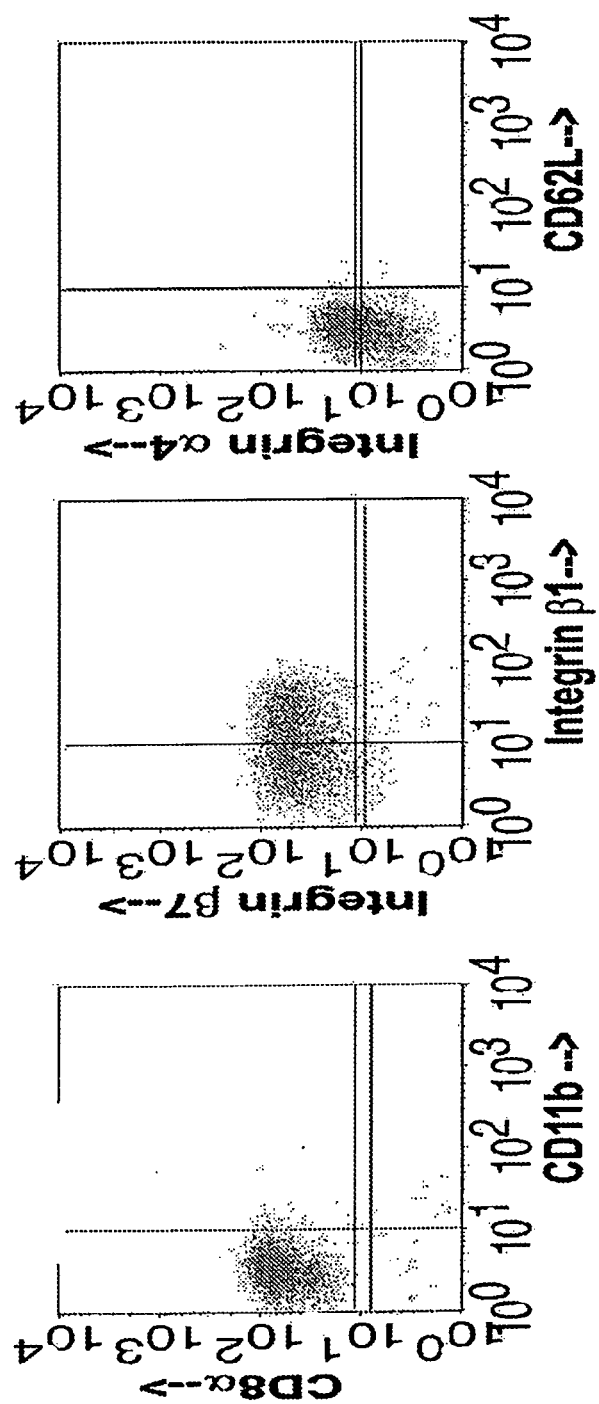
FIG. 17. Cell surface phenotype of the *Chlamydia*-specific T-cell clone CD8-2 measured by flow cytometry. Right most panel, CD8α versus CD11b; middle panel, integrin β7 versus integrin β1; left panel, integrin α4 versus CD62L.

A representative experiment with a good match between control immune-irradiated bm12 and C57BL/6J splenocyte activation by UV-*C. muridarum* is shown in FIG. 16. Referring now to FIG. 16A, some of these experiments revealed that three of the five CD8 T cell clones tested were less activated by bm12 (I-A$^{bm12}$) APC than syngeneic C57BL/6J (I-A$^b$) APC, but that two CD4 T-cell clones, CD4-4 & CD4-5, were indifferent to the 3 amino acid change in the MHC class II beta chain I-A$^{bm12}$ (FIG. 16A). Referring now to FIG. 16B, two of the CD8 T-cell clones, CD8-2 & CD8-5, were unable to recognize UV-*C. muridarum*-pulsed immune-irradiated bm12 splenocytes, as the level of IFN-γ triggered by the bm12 APC was no greater than that of UV-*C. muridarum*-pulsed-immune-irradiated bm12 splenocytes alone. These results are consistent with MHC class II-restriction for at least two of the five CD8 T-cell clones that were tested. Definitive mapping of MHC restriction element for the CD8 T-cell clones may require the use of MHC class I-deficient mice. Referring now to FIG. 17, the cell surface phenotype of *Chlamydia*-specific T-cell clone CD8-2 was studied by flow cytometry. Still referring to FIG. 17, both putative MHC class II-restricted *Chlamydia*-specific CD8 T-cell clones, CD8-2 & CD8-5, express the mucosal homing receptor α4β7$^+$ (e.g. CD8-2) consistent with their generation during clearance of the original *C. muridarum* genital tract infection.

Figure 18:
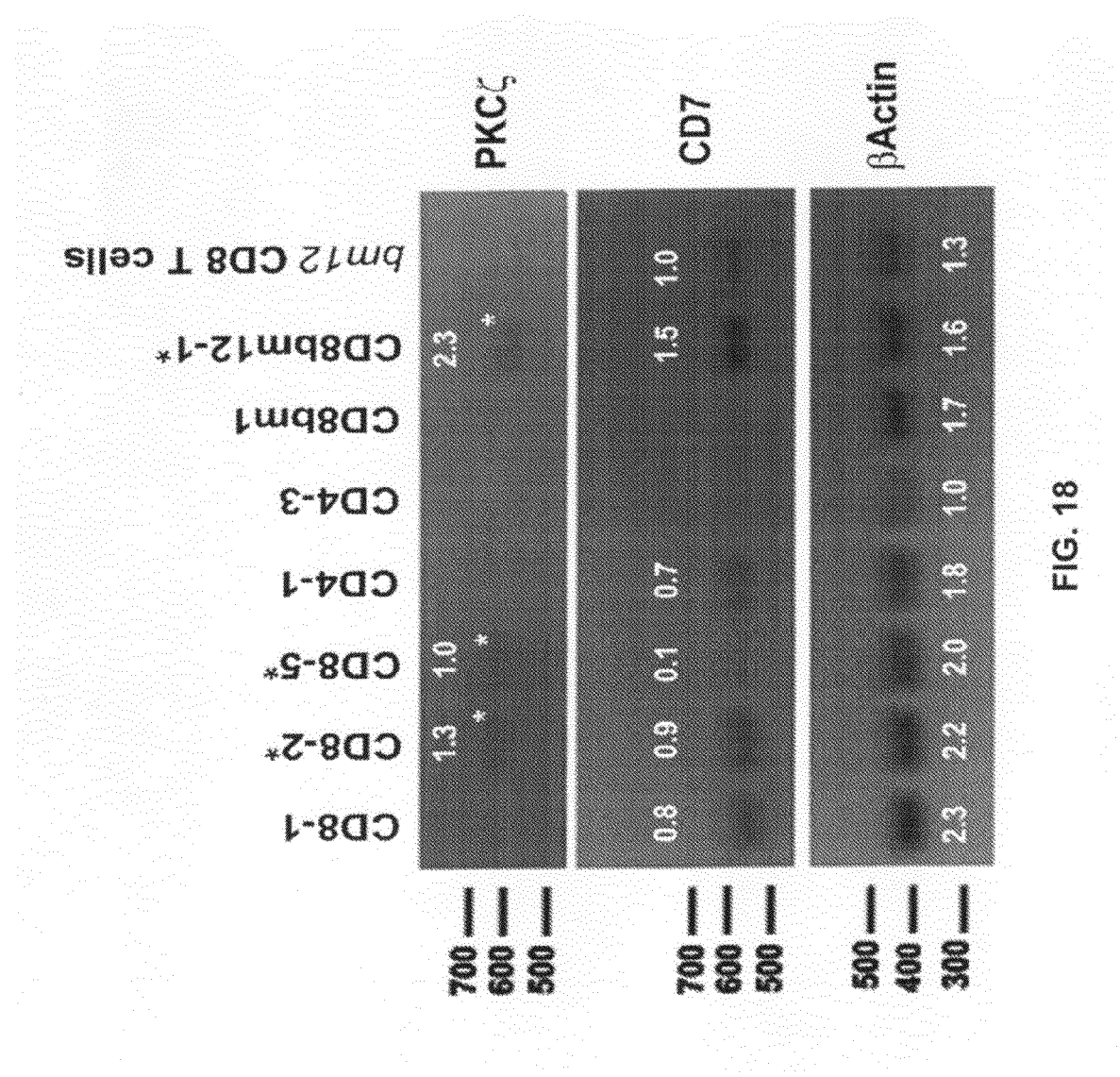
FIG. 18. Gels showing the results of semi-quantitative RT-PCR run on PCKζ, CD7 and β-actin in various selected *Chlamydia*-specific T-cell clones.

Of immediate interest was whether these *Chlamydia*-specific CD8 T-cell clones were CD7$^+$ and expressed PKCζ, as seen with the MHC class II-specific alloreactive CD8 T-cell clone CD8bm12-1 (Table 1). To test this, total RNA was isolated from CD8bm1, CD8bm12-1, histopaque purified *Chlamydia*-specific CD4 & CD8 T-cell clones, and splenic CD8 T-cells purified from a bm12 mouse spleen using magnetic bead technology (>90% pure by flow cytometry; data not shown) was isolated. 100 ηg of total RNA was RT-PCR amplified using a semi quantitative protocol with primers for β-actin, CD7, and PKCζ. Referring now to FIG. 18 densitometry was performed on an inverted image to quantify mRNA. All densitometry values were normalized to β-actin levels in order to make valid comparisons between cell lines. The T-cell clones apparently restricted by MHC class II are noted with asterisks. As seen consistently in over 1+ years in culture, the CD8bm1 T-cell clone was CD7negPKCζneg while the CD8bm12-1 T-cell clone was CD7+PKCζ+. PKCζ expression correlated with putative MHC class II-restriction as 3 out of 3 'class II-restricted' CD8 clones, CD8-2, CD8-5, CD8bm12-1, were positive, while four other CD8 and CD4 T-cell clones were negative (Chi-square analysis of PKCζ vs. MHC class II-restriction based on seven T-cell clones pvalue=0.06). In addition, PKCζ is not expressed by the majority of splenic CD8 T-cells as no PKCζ RT-PCR product was detected for purified splenic CD8 T-cells isolated from a bm12 mouse (last lane in FIG. 18). Unlike PKCζ, CD7 levels did not correlate with 'MHC class II restriction'.

*Chlamydia*-specific CD8 and CD4 T-cells differed dramatically in levels of CD7 mRNA. These murine *Chlamydia*-specific CD8 T-cells showed a high-low-negative phenotype, analogous to the high-low-negative CD8 phenotypes described in human peripheral blood. In humans CD7low & CD7negative CD8 T-cells represent 1-2% & 28% of the circulating CD8 T lymphocytes, respectively. One of the two *Chlamydia*-specific CD4 T-cell clones tested was CD7negative. In human peripheral blood CD7 negCD4 T-cells make up 19% of circulating CD4 T-cells (Reinhold, et al., 1993). Though data about CD7 T-cell subsets is absent in mice, having analyzed a limited number of clones, it is interesting to speculate that there may be an over representation of CD7$^{neg}$ CD4 T-cells (50%) and CD7$^{low}$ CD8 T-cells (25%) among these *Chlamydia*-specific T-cell clones. A lack of murine CD7 antibody reagents has limited a functional understanding of the role of CD7+ and CD7$^{neg}$ T-cells in host defense. Antigen-specific CD7$^{neg}$ T lymphocytes have been described for human microbial pathogens (Aandahl, et al., 2004). CD7$^{neg}$CD4 T-cells may be dependent on IL-15 for survival (Rappl, et al., 2001), potentially linking their biology to the mucosal immune compartment where IL-15 is an important cytokine made by multiple cell types including epithelial cells (Di Sabatino, et al., 2006). IL-15 mRNA is up regulated in this Bm1.11 oviduct epithelial cells in response to infection with *C. muridarum* (Johnson, R. M., 2004). An hypothesis that is consistent with the data is that *Chlamydia*-specific α4β7$^l$CD7 low/negative CD4 or CD8 T-cells correlate with protection in the genital tract of mice infected with *C. muridarum* based on their generation during clearance of a genital tract infection.

T-cell subset differentiation utilizing PKCζ or CD7 as biomarkers would be useful during evaluation of putative *Chlamydia* vaccines if either biomarker identified T-cells that were functional in the reproductive tract. Based on the preliminary "epithelial" data, it appears that that CD8zeta T-cells (CD8 T cells that are PKCζ+) uniquely reflect T-cell activation via MHC class II at the epithelial interface, and that CD7$^{low/neg}$ CD4 & CD8 T lymphocytes and CD8zeta T-cells expand during clearance of a *C. trachomatis* infection from the genital tract. Also consistent with these results is that MHC class II-restricted CD8zeta T-cells can mediate protective host immunity based on data from the CD4 knockout mice (clearance delayed 10 days) versus MHC class II-deficient mice (no clearance). These results in the mouse, suggest that it may be possible to use this data to evaluate vaccines against *Chlamydia* in human clinical trials. For example, human subjects enrolled in a candidate *Chlamydia* vaccine trial such as CPAF/IL-12 administered nasally (Murthy, et al., 2007) or rVCG-MOMP/CTA2B administered vaginally (Ekong, et al., 2008)), would have peripheral blood collected on, for example, day zero, two weeks, and four weeks after vaccination. Peripheral blood samples would be activated in vitro with recombinant antigen (CPAF or MOMP) or UV-*C. trachomatis*, and flow cytometry performed to assess the frequency of $CD7^{neg}CD4+$ T-cells (or $CD7^{low/neg}$ CD8+ T-cells or CD8zeta T-cells) producing IFN-γ prior-to and after vaccination. Tetramer analysis could be substituted for the UV-*Chlamydia* T-cell activation step if appropriate tetramer and HLA-defined patient population were available. Successful vaccination would be reflected by a vaccine-associated increase in the frequency of *Chlamydia*-specific (i.e. IFN-γ-producing or tetramer positive) $CD7^{neg}CD4$ T-cells. Using the murine model it is possible to test this type of vaccine assessment strategy.

One of the principle differences between mouse and human immune defenses against *Chlamydia* infections relates to innate defense functions induced by interferon gamma. Human epithelial cells exposed to interferon gamma induce indoleamine-2,3-dioxygenase (IDO) (Nelson, et al., 2005; Roshick, et al., 2006). IDO depletes the intracellular tryptophan pool, thereby starving invading intracellular pathogens dependent on the host cell for tryptophan. This effect can be demonstrated in vitro using human epithelial cells and interferon gamma, and was originally described as a persistent state in which *Chlamydia* replication was suspended while the bacteria remained viable (Beatty, et al., 1994). However subsequent work showed that human *Chlamydia* strains that cause genital tract infections have evolved a mechanism to evade this innate interferon gamma induced defense mechanism. Human *Chlamydia* genital serovars have a tryptophan salvage pathway that allows them to synthesize their own tryptophan from indole, a substrate readily available in the human genital tract (Fehlner-Gardiner, et al., 2002). This indole-based evasion mechanism is dependent on a tryptophan operon encoded in the human *Chlamydia* serovars "plasticity zone"; the only region of the genome that differs significantly between the human and rodent *Chlamydia* serovars. The rodent *Chlamydia, Chlamydia muridarum*, does not have a tryptophan operon, and on that basis cannot be rescued by indole when growing in human epithelial cells treated with interferon gamma (Nelson, et al., 2005). *C. muridarum* is helpless, i.e. cannot replicate, in human epithelials treated with interferon gamma.

The murine model is potentially deficient in that reproductive tract epithelial cells do not express IDO, however this is not likely biologically important to the mouse model as human *C. trachomatis* genital tract serovars have a mechanism for evading IDO in human cells, and *C. muridarum* is not subject to IDO in murine cells/mouse model. It appears that at the functional level, IDO does not restrict human or murine *Chlamydia* strains from replicating in the mouse model, and IDO is unlikely to restrict human *Chlamydia* strains during human infections.

Conversely, the plasticity zone of *Chlamydia muridarum* has a set of Yop-T-related cytotoxins that are not present in the human *C. trachomatis* plasticity zone. These cytotoxins are believed to be responsible for inactivating interferon gamma inducible p47 GTPases that would otherwise prevent *C. muridarum* from replicating in murine epithelial cells exposed to interferon gamma (Nelson, et al., 2005). Consistent with this hypothesis, murine *C. muridarum* is able to replicate well in murine epithelial cells treated with interferon gamma while human genital serovars of *C. trachomatis* cannot (Al-Zeer, et al., 2009; Coers, et al., 2008; Nelson, et al., 2005). *Chlamydia trachomatis* is helpless, i.e. cannot replicate, in murine epithelial cells treated with interferon gamma because of p47 GTPases. This difference may account for why the murine model is suboptimal for infection with human *C. trachomatis* strains in that reproductive tract epithelial cells express p47 GTPases that do not exist in human reproductive tract epithelial cells, which limit human (but not rodent) *C. trachomatis* strains from replicating in murine epithelial cells. At the functional level, interferon gamma-inducible p47 GTPases have no effect on *C. muridarum* replication in the mouse model, but p47 GTPases represent a major innate barrier to replication of human *C. trachomatis* strains in the mouse model.

The existence of species specific murine p47 GTPases make it highly problematic to do vaccine development or to study pathogenesis using human *Chlamydia* strains in the mouse model because the uncomplicated regional production of interferon gamma, even by innate mechanisms such as NK cells, is likely sufficient to induce p47 GTPases and abort human *Chlamydia trachomatis* strain replication in murine reproductive tract epithelium. This difference creates an unacceptably low bar for defining protective immunity because human and mouse serovars have known mechanisms for evading innate interferon gamma defense mechanisms when they are replicating in their natural host species; tryptophan operon for human strains and Yop-T related cytotoxins for *C. muridarum*.

It has been suggested that the murine model could be optimized by knocking out p47 GTPases in order to realistically use human strains in the mouse model (Nelson, et al., 2005). However, there are seven different p47 GTPases, there is no agreement within the field on which ones are important or how they work, and there is always the possibility that they may be redundant.

This approach to optimizing the mouse model also ignores thousands of years of evolution in separate species that is reflected in amino acid differences in homologous human and mouse serovar genes encoded outside the plasticity zone.

Moreover, the *C. muridarum* mouse model has one major problem as a model for studying human *Chlamydia* infections. Murine epithelial cells have interferon gamma inducible nitric oxide synthetase (iNOS) that is not expressed by human reproductive tract epithelial cells (Nelson, et al., 2005; Roshick, et al., 2006). There is clear evidence that T cells can mediate protective immunity through induction of epithelial iNOS (Igietseme, J. U., 1996; Igietseme, et al., 1996). This was initially thought to be the mechanism by which CD4 T cells mediated protective immunity against *Chlamydia*, however subsequent studies showed normal clearance kinetics of *C. muridarum* in iNOS knockout mice (Igietseme, et al., 1998; Ramsey, et al., 1998); therefore T cell induced iNOS is not a critical protective mechanism. T cell induction of iNOS in murine epithelial cells represents a non-human mechanism for controlling/resolving *Chlamydia* infection in the mouse model. Fortunately, iNOS is dispensable for resolving murine *C. muridarum* genital tract infections.

Recently published data shows that CD4 T cell clones specific for *C. muridarum* had variable ability to control *C. muridarum* replication in murine reproductive tract epithelial cells (Jayarapu, et al., 2009). That publication shows that some CD4 T cells were unable to control *C. muridarum* replication, some were ok/intermediate, and some were very potent. The novel finding that drives this invention disclosure is the finding that some CD4 T cell clones are entirely dependent on iNOS for controlling *C. muridarum* replication, while the most potent CD4 T cell clones can control replication of epithelial cells in the presence of inhibitors that completely block iNOS production of nitric oxide.

Figure 12:
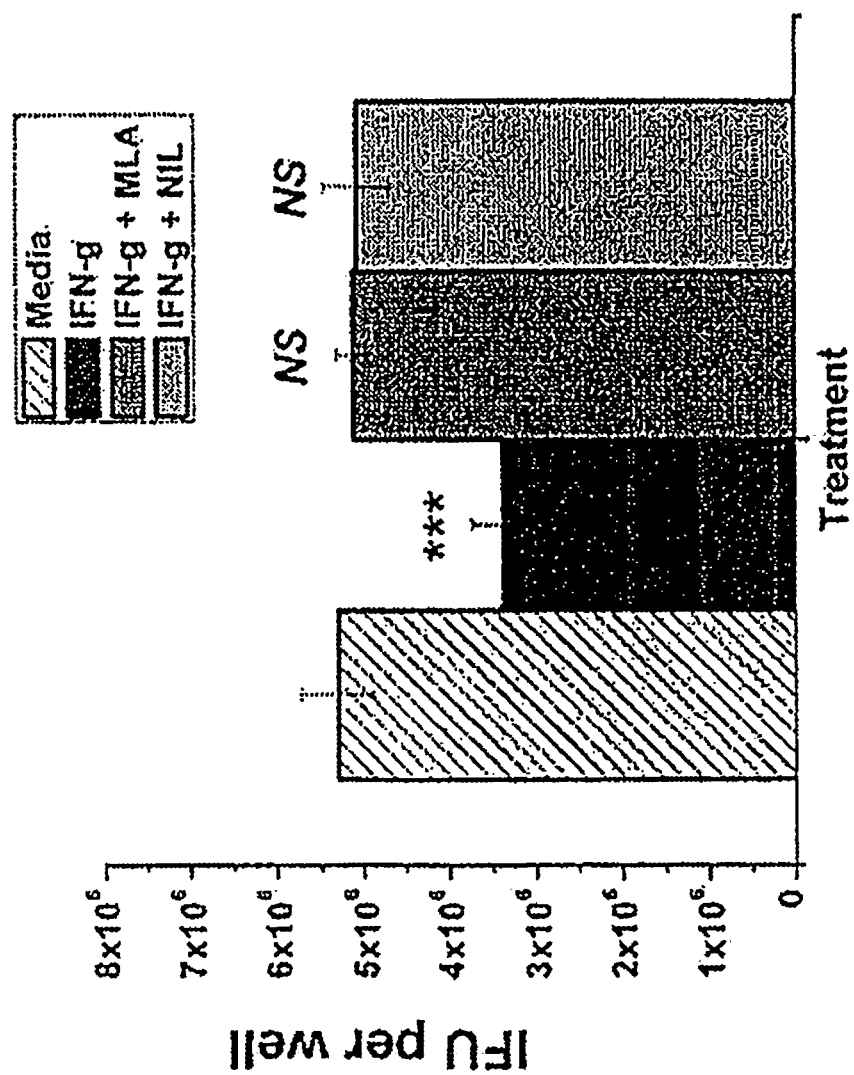
FIG. 12. Bar graph showing the effect of iNOS inhibitors on *C. muridarum* replication in infected C57epi.1 epithelial cells.

Referring now to FIG. 12A, the modest inhibitory effect of IFN-γ was reversed by blocking NO production with either MLA or NIL. FIG. 12B shows effects of iNOS inhibitors on *C. muridarum* replication in infected C57epi.1 epithelial cells. According to FIG. 12B, C57.1epi cells were untreated (hatched bar) or pretreated with IFN-γ (10 ηg/ml×14 hours) in absence (black bar) or presence of MLA (gray bar) or NIL (light gray bar), and then infected with *C. muridarum* (3 IFU/cell). Wells were harvested at 36 hours postinfection and *C. muridarum* (IFU) quantified on McCoy monolayers. Comparisons were made to the infected (hatched bar).

Figure 19A:
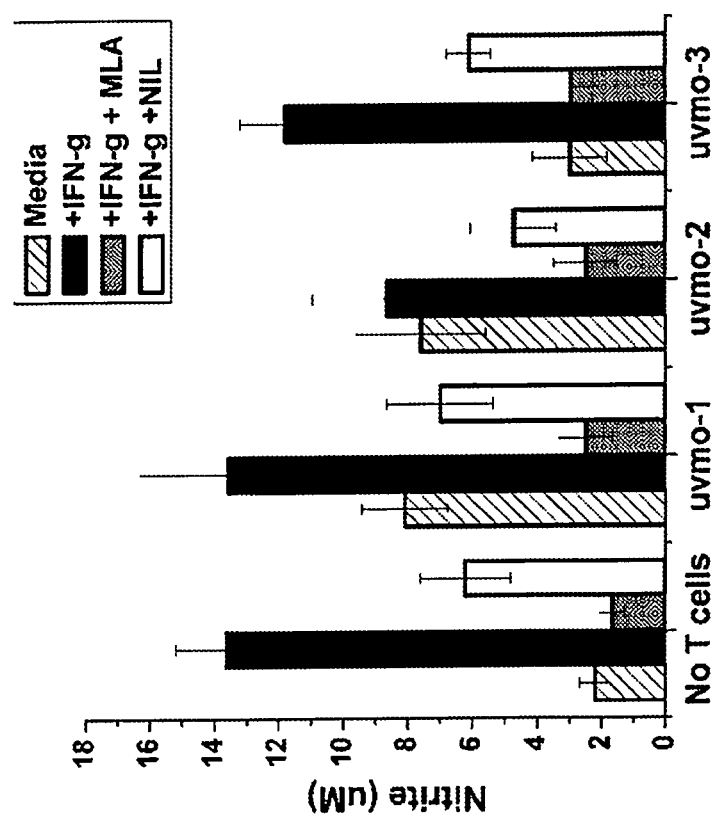
FIG. 19A. Bar graph showing iNOS inhibitors MLA & NIL blocking infection- and IFN-γ-induced nitric oxide production by C57epi.1 epithelial cells, in the absence or presence of T cell clones.

Production of NO by C57.epi.1 epithelial cells (in the absence or presence of CD4 T Cell clones) is effectively inhibited by N-monomethyl-$_L$-arginine (MLA) and $_L$-N$^6$-(1-iminoethyl)lysine hydrocholoride (NIL). Referring now to FIG. 19A, C57 epi.1 epithelial cells, untreated (hatched bars) or pretreated with IFN-γ (10 ηg/ml×14 hours) in the absence (black bars) or presence of iNOS inhibitors MLA (gray bars) or NIL (light gray bars),—were infected with *C. muridarum* (3 IFU/cell). Four hours later, the inocula were removed and monolayers cocilted with and with CD4 T-cell clones uvmo-1, -2, and -3 for an additional 32 hours. Supernatants were collected at 36 hour post infection, 32 hour post T cell coculture, and analyzed for NO production measured as nitrite. As shown, IFN-γ significantly induced NO production in C57.1 epithelial cells, roughly 6-fold with p<0.0001. Also, MLA and NIL were effective inhibitors of NO production, as MLA blocked>90% of IFN-γ-induced NO; NIL blocked ~60%. Further, the presence of CD4 T Cell coculture did not effect the levels of NO production in the presence of MLA.

Still referring to FIG. 19A, the iNOS inhibitor MLA blocks infected epithelial nitrite production to the background level of 2 uM even in the presence of exogenous interferon gamma and CD4 T cell clones uvmo-1,-2,-3. Inhibition of iNOS activity induced by interferon gamma, and interferon gamma plus CD4 T cell clones uvmo-1,-2,-3, in infected C57epi.1 murine epithelial cells using the iNOS inhibitors N$^G$-Monomethyl-L-arginine (MLA) and L-N$^6$-(1-Iminoethyl)lysine (NIL). iNOS activity was measured as nitrite in 24 h culture supernatants. MLA is the more potent inhibitor, blocking nitrite levels down to background levels seen in infected epithelial cells absent exposure to interferon gamma and T cell clones. 24 h supernatants from uninfected C57epi.1 murine epithelial cells have nitrite levels>0<1.5 uM.

Figure 19B:
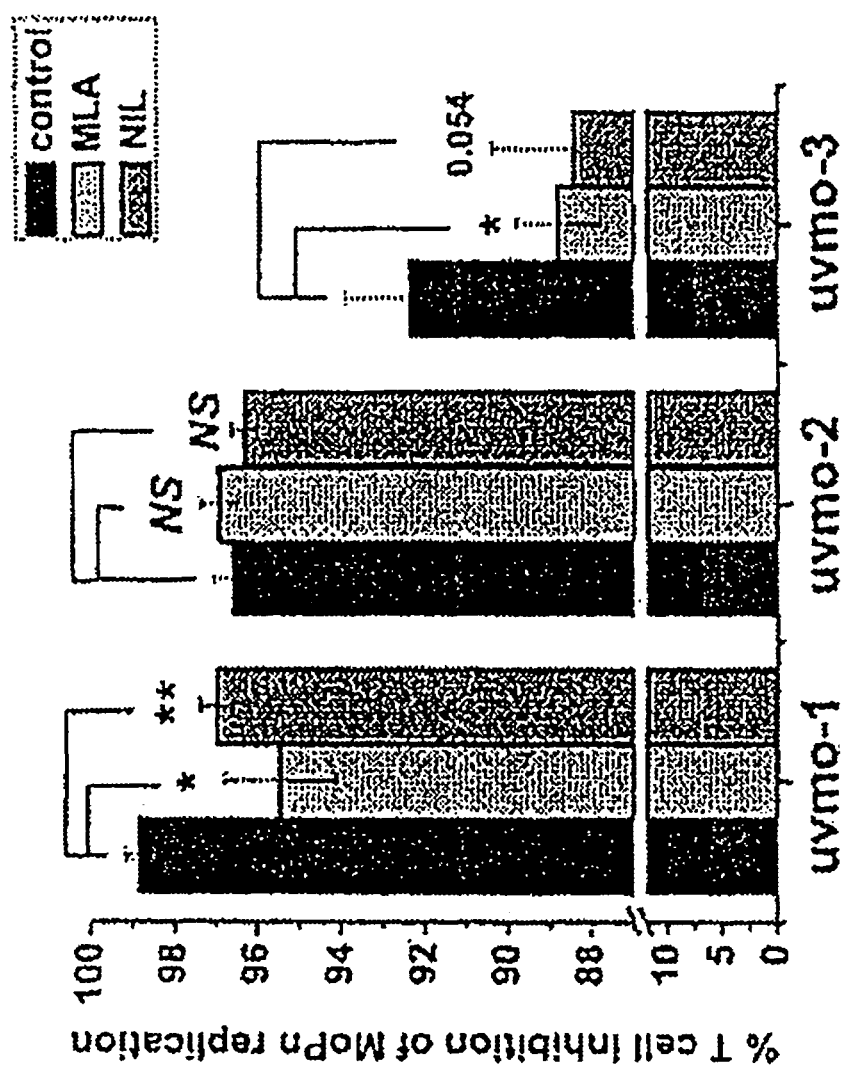
FIG. 19B. Bar graph showing the percent T cell inhibition of *C. muridarum* replication in epithelial cells by an iNOS-independent mechanism.

Referring now to FIG. 19B, *C. muridarum* replication in epithelial cells, by an iNOS-independent mechanism, is controlled by IFN-γ-independent CD4 T cell clones. According to FIG. 19B, C57epi.1 epithelial cells were pretreated for 14 hours with IFN-γ in the absence (black bars) or presence of iNOS inhibitors MLA (light gray bars) or NIL (gray bars), then infected with 3 IFU/cell *C. muridarum*. Inocula were removed 4 hours later and 1.5×10$^5$ T cell clone cells were added in the absence or presence of MLA or NIL. Wells were harvested 36 hours post infection and *C. muridarum* quantified on McCoy monolayers. Comparisons were made to the no inhibitor control (black bar) for each of the three T cell clones.

Figure 20A:
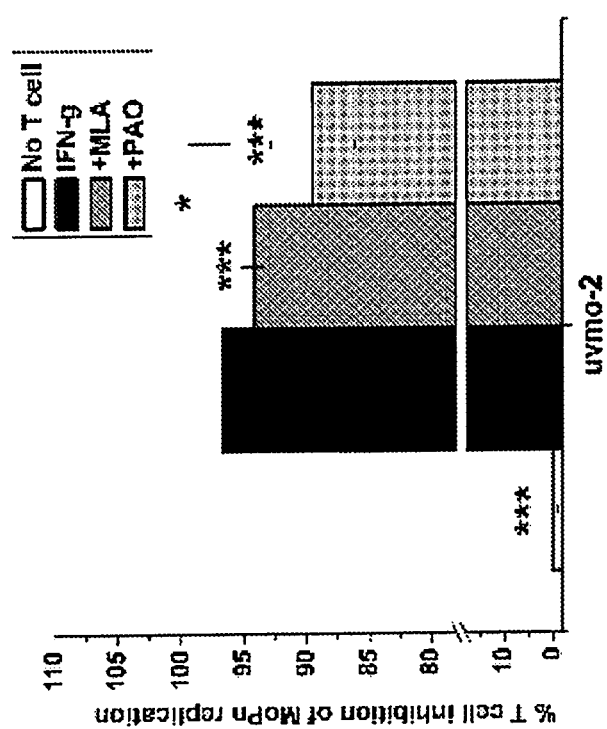
FIG. 20A. Plot of % T-cell control of *C. muridarum* replication in epithelial cells measured with the protective T cell clone uvmo-2: control (no T-cells); added IFN-γ; added MLA; or added PAO.
Figure 20B:
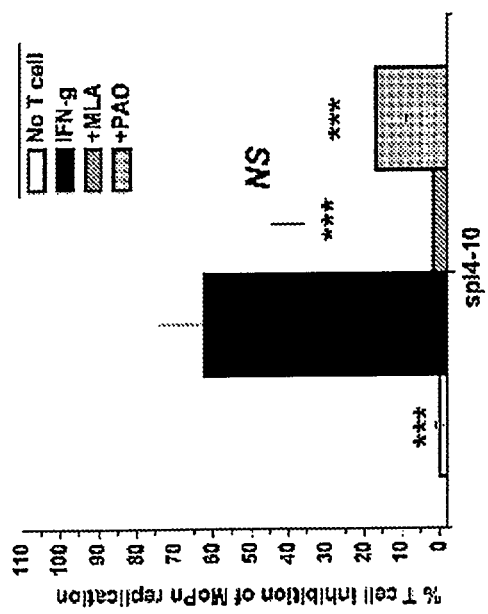
FIG. 20 B. Plot of % T-cell inhibition of MoPn (*C. muridarum*) replication measured with the IFN-γ dependent T cell clone sp14-10: control (no T-cells); added IFN-γ; added MLA; or added PAO. muridarum replication in epithelial cells.
Figure 21:
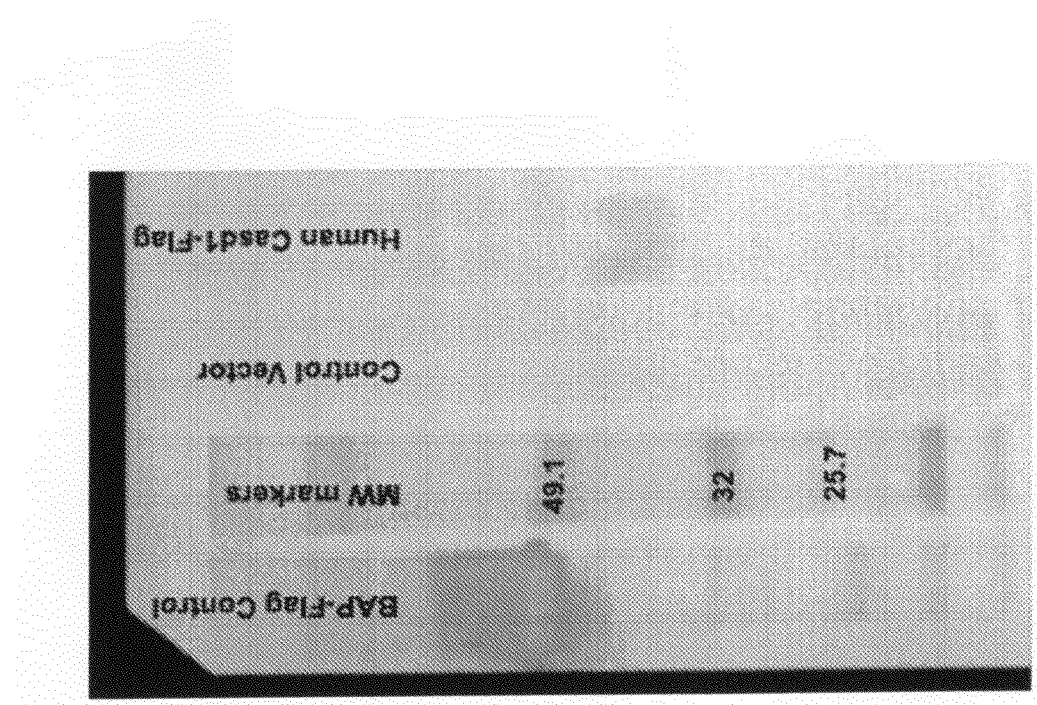
FIG. 21. Western blot of the extracellular domain of human Casd1 with a c-terminal Flag-epitope tag, secreted into the media by transiently transfected 293T cells.
Figure 22:
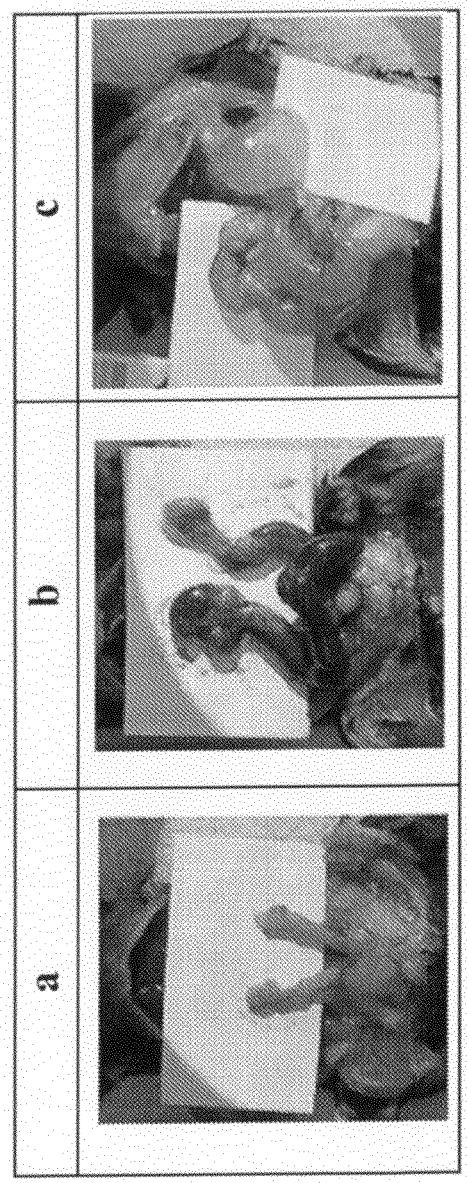
FIG. 22. Photograph of the genital tracts of Plac8ko mice (panels B & C) infected with *Chlamydia muridarum*; panel A is a normal C57BL/6J mouse genital tract for comparison.
Figure 23A:
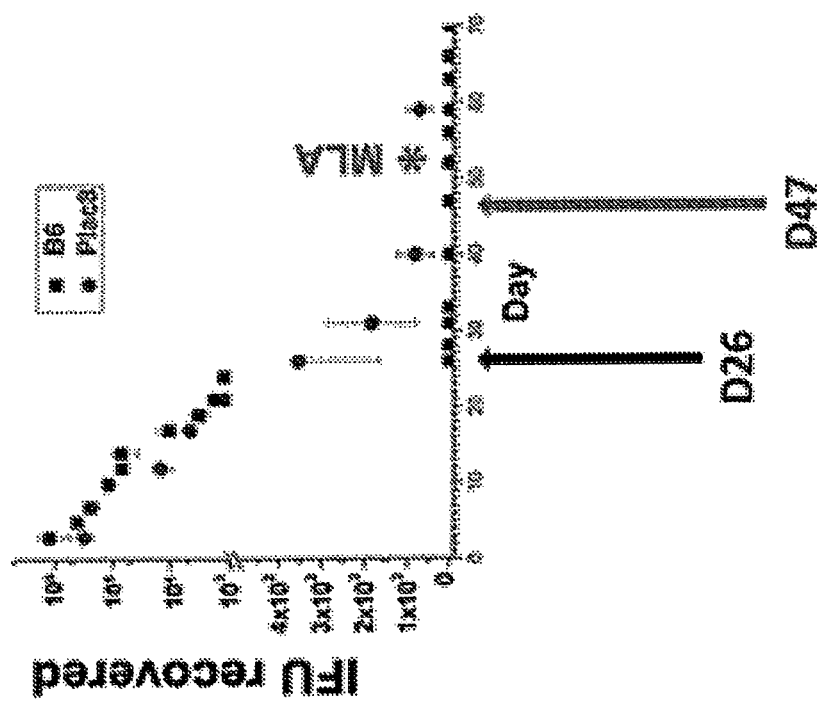
FIG. 23A. Plot of IFU shed over time from either control C57BL/6J mice or experimental Plac8ko mice; iNOS inhibitor MLA added to drinking water at day 52 post-infection.
Figure 23B:
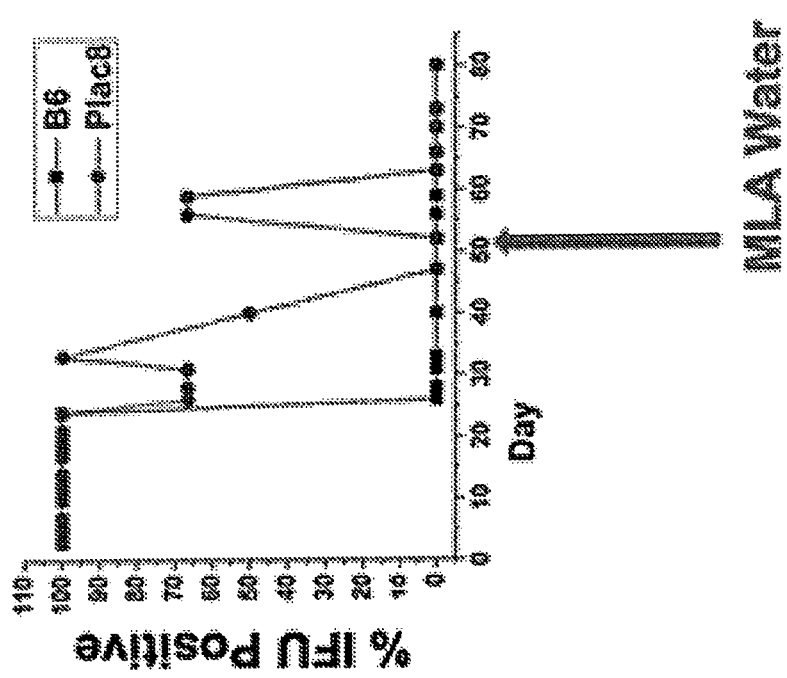
FIG. 23B. Plot of % of mice shedding *C. muridarum* over time from either control C57BL/6J mice or experimental Plac8ko mice treated with the iNOS inhibitor MLA added to drinking water at day 52.
Figure 24A:
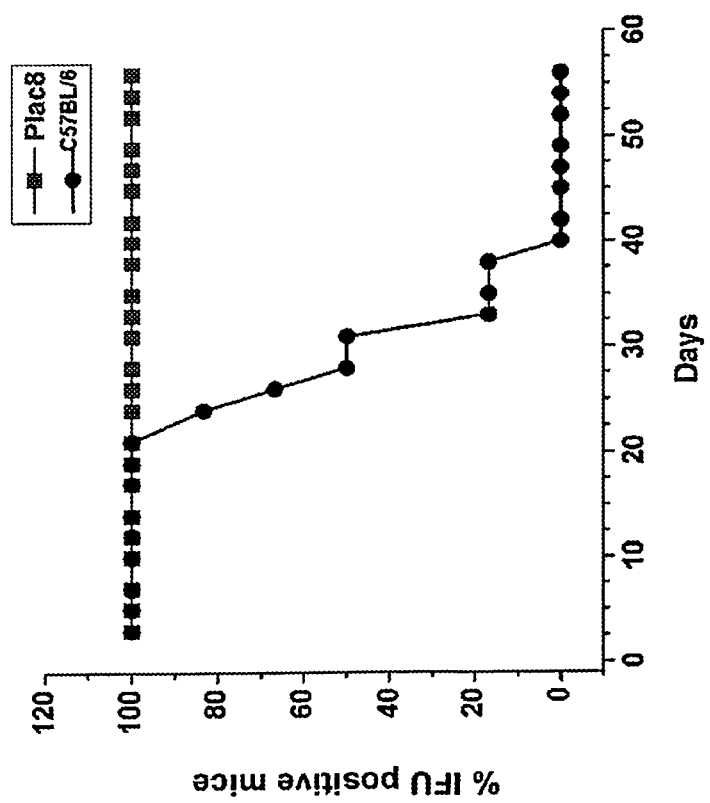
FIG. 24A. Percent of mice shedding *C. muridarum*; Plac8ko mice compared with C57BL/6J control mice in presence of MLA (iNOS inhibitor in drinking water on day 0) throughout course of infection.
Figure 24B:
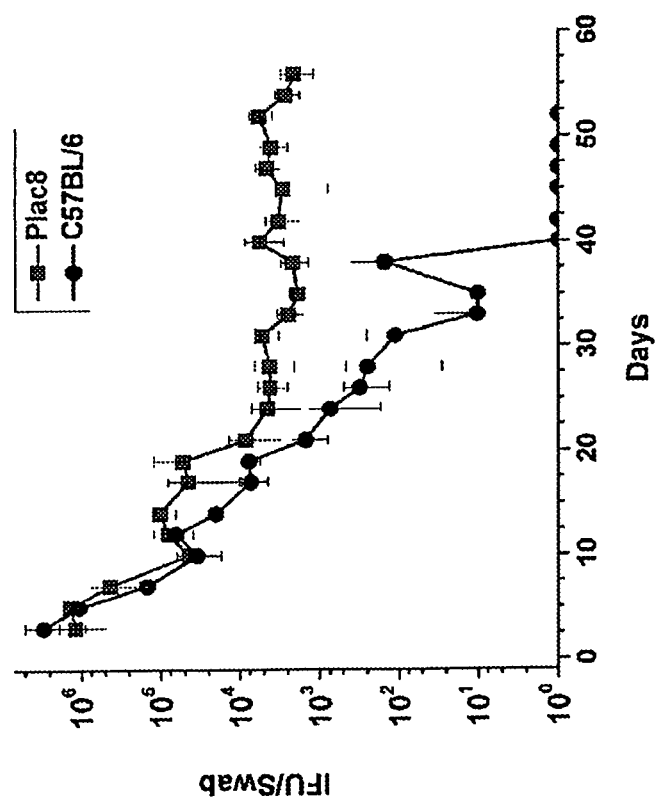
FIG. 24B. Intensity of shedding measured as IFU per swab at indicated time points.

Referring now to FIGS. 20A and 20B, discovery of two distinct subsets of *Chlamydia*-specific CD4 T cell clones; one iNOS-dependent and one iNOS-independent. Ability of T cell clones uvmo-2 and sp14-10 to control replication of *C. muridarum* in C57epi.1 epithelial cells in the absence and presence of inhibitors of iNOS (MLA) and T cell degranulation (phenylarsine oxide; PAO). Blocking T cell degranulation had an effect on both clones' ability to control *C. muridarum* replication. Inhibition of iNOS with MLA completely abrogated the ability of clone sp14-10 to control *C. muridarum* replication (iNOS-dependent), while having a statistically significant but biologically trivial effect on uvmo-2's ability to control *C. muridarum* replication (iNOS-independent). Degranulation also occurs in these subset of T-cells (Jayarapu, et al., 2010).

Still referring to FIGS. 20A and 20B., the role of iNOS in controlling *C. muridarum* replication in epithelial cells, was examined, there were two distinct types of protective T cells. One type, represented by sp14-10 (FIG. 20B), was entirely dependent on iNOS to control *C. muridarum* replication; in this type the iNOS inhibitor MLA completely abolished its ability to control *C. muridarum*. The second more potent type, represented by T cell clone uvmo-2 (FIG. 20A), was able to control *C. muridarum* replication independent of iNOS as it was largely unaffected by MLA; i.e. inhibition of replication went from ~96% to ~94% in the presence of MLA. Because human reproductive tract epithelial cells do not express iNOS, the T cell clone protective mechanism dependent on iNOS utilized by sp14-10 is irrelevant to human host defense. The iNOS independent mechanism utilized by uvmo-2 is likely the T cell mechanism relevant to human vaccine development and human-relevant studies of protective immunity and immunopathology. A tissue-specific knockout of iNOS in epithelial cell lines would remove the non-human iNOS-dependent mechanism for controlling/resolving *Chlamydia* infections from the mouse model. Human *Chlamydia* strains would still be compromised in an epithelial tissue-specific iNOS knockout mouse model because of p47 GTPases, however using *C. muridarum* would likely accurately model the iNOS-independent adaptive host defense mechanism relevant for clearing *C. trachomatis* from the human reproductive tract. An epithelial tissue-specific iNOS knockout mouse would be an optimized animal model for studying pathogenesis and vaccination strategies relevant to human *C. trachomatis* genital tract infections.

Some critical factors to guide development of an optimized mouse model for vaccine development and pathogenesis research include:

1) Murine and human *Chlamydia* genital tract serovars are indifferent to innate effects of interferon gamma when they are replicating in their natural host; i.e. p47 GTPases & iNOS (mouse) and IDO (human) are not important for host defense in the natural hosts.

2) iNOS & p47 GTPases are unique to mouse epithelium, but neither is critical for controlling *C. muridarum* replication, with or without T cells present.

3) Murine and human *Chlamydia* genital serovars have evolved independently in their natural host for many thousands of years, which is reflected by amino acid changes in homologous proteins encoded outside the plasticity zone.

4) The currently available mouse models are highly problematic when used to model infections with strains of *Chlamydia* that infect humans because human serovars are unable to evade murine p47 GTPases. Strains of *Chlamydia* that infect humans are evolved to replicate in human reproductive tract epithelium, and these strains have not evolved to resist the toxic effects of nitric oxide found in the epithelium of wild-type mice.

5) CD4 T cells and MHC class II are critical to host protective immunity to *Chlamydia* infection in mice, and likely in humans because of the high degree of conservation of function seen between the human and mouse adaptive immune response.

6) Using human *Chlamydia* in a mouse model does not impart a vaccine development advantage as mouse and human T cell epitopes for individual *Chlamydia* proteins will be different based on differences in mouse MHC class II versus human HLA-D antigen presenting molecules.

7) Mice have two classes of *Chlamydia*-specific CD4 T cell clones that can mediate protective immunity; iNOS-dependent (irrelevant to human immunobiology) and iNOS-independent (relevant to human immunobiology).

8) An epithelial tissue-specific iNOS knockout mouse would remove the human-irrelevant T cell-mediated mechanism from the mouse model, thereby optimizing it to reflect only the immunobiology likely to be relevant in humans.

Some aspects of the invention include an optimized mouse model that is a tissue specific knockout mouse in which iNOS expression is knocked out in epithelial cells and preserved in hematopoietic lineage cells such as monocytes, macrophages, and dendritic cells. One method for generating such mice is by making two separate transgenic mice each homozygous in a different set of desirable genetic traits and then mating them.

One mouse in the mating pair designated as mouse 1, is a homozygous knock-in mouse with iNOS gene/exon flanked by loxP sites. The loxP flanked iNOS construct would homologously recombine with the native iNOS genomic DNA in order to replace it. Still another mouse in the mating pair is a homozygous Cre-recombinase knockin with Cre-recombinase expression under the control of an epithelial-specific promotor. Cre-recombinase recognizes adjacent loxP sites and excises the DNA residing between them. Homozygous mouse 1 would be mated with homozygous mouse 2 to generate mice expressing Cre-recombinase in epithelial cells, leading to epithelial cell-specific deletion of iNOS.

A transgenic mouse according to the instant disclosure will possess a number of advantages for modeling the pathology of microorganisms such as *Chlamydia* that infect humans including, for example, epithelium-specific iNOS-deficient mouse would not be able to utilize the human-irrelevant iNOS-dependent CD4 T cell mechanism to control *Chlamydia*-replication. Such a mouse would be dependent on the T cell mechanism operative in the iNOS-deficient mouse that results in normal clearance of *C. muridarum* from the genital tract; this is likely the relevant mechanism in humans as human reproductive tract epithelial cells do not express iNOS, and murine and human T cell biology is highly conserved across the species. Preserving iNOS expression in hematopoietic cell types would mirror the immunobiology of human iNOS, and likely limit artifactual dissemination of *C. muridarum* from the genital tract in iNOS deficient macrophages.

The transgenic mouse model disclosed herein, or its functional equivalent, when used in combination with *C. muridarum* genital tract infections preserves the requirement for a CD4 T cell mediated immune response that is more robust than simply making local interferon gamma to induce nitric oxide production and p47 GTPases. This more realistic threshold for protective immunity will be critical for assessing components of a *Chlamydia* subunit vaccine, and vaccination strategies that generate protective immune responses.

Referring now to FIG. 21. Expression of the predicted extracellular domain of human Casd1 tagged with a 3×Flag epitope. 293T cells were transiently transfected with the following vectors; a BAP-Flag vector (bacterial alkaline phosphatase tagged with a Flag epitope), an empty control Flag vector, and a new vector construct containing the predicted extracellular domain of human Casd1, including its endogenous signal sequence (predicted), tagged with a 3×Flag epitope. 200 k cell lysate equivalents (BAP-Flag) or 1 ml of conditioned media (control vector & Casd1-Flag) were immunoprecipitated with anti-Flag magnetized agarose beads, run on a 10% SDS PAGE gel, transferred to nitrocellulose, and probed with anti-Flag antibody coupled to HRP (horse radish peroxidase). Predicted size of the flag-tagged Casd1 extracellular domain, based on its amino acid sequence with a 3×Flag epitope tag, is roughly 34 kd. Slower migration in the SDS gel likely reflects N-linked & O-linked glycosylation of predicted sites in the Casd1 extracellular domain. Transfection of Casd1extracellular domain with its endogenous signal peptide led to secretion of a ~40 kd flag-tagged protein into the culture medium, consistent with a bona fide mammalian gene.

Referring now to FIG. 22. Extreme genital tract pathology in Plac8ko mice when MLA (iNOS inhibitor) is included in the drinking water at initiation of infection with *C. muridarum*. Control C57BL/6 mice (not shown) and experimental Plac8ko mice were vaginally infected with $5\times10^4$ IFU *C. muridarum* with addition of MLA to the drinking water at day 0. Two Plac8ko mice could not have genital swabs performed because local swelling related to the infection blocked the vaginal vault. These mice were killed at 4 weeks post-infection when they developed obvious abnormal abdominal swelling. A) upper and lower reproductive tract from an uninfected C57BL/6 mouse (normal anatomy). B) gangranous reproductive tract of an infected Plac8ko mouse 4 weeks post-infection. C) extreme hydrosalpinx and hydrouterus in an infected Plac8ko mouse 4 weeks post-infection. The severe pathology seen in the Plac8ko mice at 4 weeks has not been seen previously in the *C. muridarum* C57BL/6 mouse model.

Referring now to FIG. 23 A. Prolonged genital tract shedding of *Chlamydia muridarum* in Plac8ko mice compared with C57BL/6 control mice. Control C57BL/6 mice and experimental Plac8ko mice were infected vaginally with $5\times10^4$ IFU *C. muridarum* on day 0, and monitored for shedding in vaginal secretions (swabs). Control C57BL/6 mice (6 mice) cleared infection by day 26 post-infection while Plac8ko mice (6 mice) cleared infection by day 47 post-infection.

Referring now to FIG. 23 B. IFU shedding before and after the addition of MLA (iNOS inhibitor) to drinking water at day 52 resulted in recurrent shedding of viable *C. muridarum* in all Plac8ko mice, but no C57BL/6 control mice.

Referring now to FIGS. 24A and 24B. Prolonged genital tract shedding of *Chlamydia muridarum* in Plac8ko mice compared with C57BL/6 control mice in presence of MLA (iNOS inhibitor in drinking water). Control C57BL/6 mice and experimental Plac8ko mice continuously treated with MLA were infected vaginally with $5\times10^4$ IFU *C. muridarum* on day 0, and monitored for shedding in vaginal secretions (swabs). Control C57BL/6 mice (6 mice) cleared infection by day 40 post-infection while Plac8ko mice (4 mice) did not clear infection even by day 56 post-infection. FIG. 24A shows % mice shedding *C. muridarum*; FIG. 24B shows intensity of shedding measured as IFU per swab at indicated time points.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES

Al-Zeer, M. A., H. M. Al-Younes, P. R. Braun, J. Zerrahn, and T. F. Meyer. 2009. IFN-gamma-inducible Irga6 mediates host resistance against *Chlamydia trachomatis* via autophagy. PLoS ONE 4:e4588.

Aandahl, E. M., J. K. Sandberg, K. P. Beckerman, K. Tasken, W. J. Moretto, and D. F. Nixon. 2003. CD7 is a differentiation marker that identifies multiple CD8 T cell effector subsets. J Immunol 170:2349-2355.

Aandahl, E. M., M. F. Quigley, W. J. Moretto, M. Moll, V. D. Gonzalez, A. Sonnerborg, S. Lindback, F. M. Hecht, S. G. Deeks, M. G. Rosenberg, D. F. Nixon, and J. K. Sandberg. 2004. Expansion of CD7(low) and CD7(negative) CD8 T-cell effector subsets in HIV-1 infection: correlation with antigenic load and reversion by antiretroviral treatment. Blood 104:3672-3678.

Arno, J. N., V. A. Ricker, B. E. Batteiger, B. P. Katz, V. A. Caine, and R. B. Jones. 1990. Interferon-gamma in endocervical secretions of women infected with *Chlamydia trachomatis*. J Infect Dis 162:1385-1389.

Baier, G. 2003. The PKC gene module: molecular biosystematics to resolve its T cell functions. Immunol Rev 192:64-79.

Beatty, W. L., T. A. Belanger, A. A. Desai, R. P. Morrison, and G. I. Byrne. 1994. Tryptophan depletion as a mechanism of gamma interferon-mediated chlamydial persistence. Infect Immun 62:3705-3711.

Bernstein-Hanley, I., J. Coers, Z. R. Balsara, G. A. Taylor, M. N. Starnbach, and W. F. Dietrich. 2006. The p47 GTPases Igtp and Irgb10 map to the *Chlamydia trachomatis* susceptibility locus Ctrq-3 and mediate cellular resistance in mice. Proc Natl Acad Sci USA 103:14092-14097.

Bonilla, F. A., C. M. Kokron, P. Swinton, and R. S. Geha. 1997. Targeted gene disruption of murine CD7. Int Immunol 9:1875-1883.

Brunham, R. C., B. Pourbohloul, S. Mak, R. White, and M. L. Rekart. 2005. The Unexpected Impact of a *Chlamydia trachomatis* Infection Control Program on Susceptibility to Reinfection. J Infect Dis 192:1836-1844.

CDC. 2004. DSTDP Facts—*Chlamydia* in the U.S., Atlanta, Ga. 2

Coers, J., I. Bernstein-Hanley, D. Grotsky, I. Parvanova, J. C. Howard, G. A. Taylor, W. F. Dietrich, and M. N. Starnbach. 2008. *Chlamydia muridarum* evades growth restriction by the IFN-gamma-inducible host resistance factor Irgb10. J Immunol 180:6237-6245.

Copin, M. C., C. Noel, M. Hazzan, A. Janin, F. R. Pruvot, J. P. Dessaint, G. Lelievre, and B. Gosselin. 1995. Diagnostic and predictive value of an immunohistochemical profile in asymptomatic acute rejection of renal allografts. Transpl Immunol 3:229-239.

Cotter, T. W., K. H. Ramsey, G. S. Miranpuri, C. E. Poulsen, and G. I. Byrne. 1997. Dissemination of *Chlamydia trachomatis* chronic genital tract infection in gamma interferon gene knockout mice. Infect Immun 65:2145-2152.

Cotter, T. W., K. H. Ramsey, G. S. Miranpuri, C. E. Poulsen, and G. I. Byrne. 1997. Dissemination of *Chlamydia trachomatis* chronic genital tract infection in gamma interferon gene knockout mice. Infect Immun 65:2145-2152.

Crotzer, V. L., and J. S. Blum. 2005. Autophagy and intracellular surveillance: Modulating MHC class II antigen presentation with stress. Proc Natl Acad Sci USA 102:7779-7780.

Darville, T., C. W. Andrews, Jr., J. D. Sikes, P. L. Fraley, L. Braswell, and R. G. Rank. 2001. Mouse strain-dependent chemokine regulation of the genital tract T helper cell type 1 immune response. Infect Immun 69:7419-7424.

Darville, T., C. W. Andrews, Jr., J. D. Sikes, P. L. Fraley, and R. G. Rank. 2001. Early local cytokine profiles in strains of mice with different outcomes from chlamydial genital tract infection. Infect Immun 69:3556-3561.

Derbigny, W. A., S. C. Hong, M. S. Kerr, M. Temkit, and R. M. Johnson. 2007. *Chlamydia muridarum* infection elicits a beta interferon response in murine oviduct epithelial cells dependent on interferon regulatory factor 3 and TRIF. Infect Immun 75:1280-1290.

Derbigny, W. A., M. S. Kerr, and R. M. Johnson. 2005. Pattern recognition molecules activated by *Chlamydia muridarum* infection of cloned murine oviduct epithelial cell lines. J Immunol 175:6065-6075.

Di Sabatino, A., R. Ciccocioppo, F. Cupelli, B. Cinque, D. Millimaggi, M. M. Clarkson, M. Paulli, M. G. Cifone, and G. R. Corazza. 2006. Epithelium derived interleukin 15 regulates intraepithelial lymphocyte Th1 cytokine production, cytotoxicity, and survival in coeliac disease. Gut 55:469-477.

el-Asrar, A. M., M. H. Emarah, J. J. Van den Oord, K. Geboes, V. Desmet, and L. Missotten. 1989. Conjunctival epithelial cells infected with *Chlamydia trachomatis* express HLA-DR antigens. Br J Ophthalmol 73:399-400.

el-Asrar, A. M., J. J. Van den Oord, K. Geboes, L. Missotten, M. H. Emarah, and V. Desmet. 1989. Immunopathology of trachomatous conjunctivitis. Br J Ophthalmol 73:276-282.

Ekong, E. E., D. N. Okenu, J. Mania-Pramanik, Q. He, J. U. Igietseme, G. A. Ananaba, D. Lyn, C. Black, and F. O. Eko. 2008. A *Vibrio cholerae* ghost-based subunit vaccine induces cross-protective chlamydial immunity that is enhanced by CTA2B, the nontoxic derivative of cholera toxin. FEMS Immunol Med Microbiol.

Fehlner-Gardiner, C., C. Roshick, J. H. Carlson, S. Hughes, R. J. Belland, H. D. Caldwell, and G. McClarty. 2002. Molecular basis defining human *Chlamydia trachomatis* tissue tropism. A possible role for tryptophan synthase. J Biol Chem 277:26893-26903

Fukumori, T., Y. Takenaka, T. Yoshii, H. R. Kim, V. Hogan, H. Inohara, S. Kagawa, and A. Raz. 2003. CD29 and CD7 mediate galectin-3-induced type II T-cell apoptosis. Cancer Res 63:8302-8311.

Gervassi, A. L., P. Probst, W. E. Stamm, J. Marrazzo, K. H. Grabstein, and M. R. Alderson. 2003. Functional characterization of class Ia- and non-class Ia-restricted *Chlamydia*-reactive CD8+ T cell responses in humans. J Immunol 171:4278-4286.

Grayston, J. T., S. P. Wang, L. J. Yeh, and C. C. Kuo. 1985. Importance of reinfection in the pathogenesis of trachoma. Rev Infect Dis 7:717-725.

Golding, H., and A. Singer. 1985. Specificity, phenotype, and precursor frequency of primary cytolytic T lymphocytes specific for class II major histocompatibility antigens. J Immunol 135:1610-1615.

Golding, H., T. Mizuochi, S. A. McCarthy, C. A. Cleveland, and A. Singer. 1987. Relationship among function, phenotype, and specificity in primary allospecific T cell populations: identification of phenotypically identical but functionally distinct primary T cell subsets that differ in their recognition of MHC class I and class II allodeterminants. J Immunol 138:10-17.

Hashimoto, K., S. J. Sohn, S. D. Levin, T. Tada, R. M. Perlmutter, and T. Nakayama. 1996. Requirement for p56lck tyrosine kinase activation in T cell receptor-mediated thymic selection. J Exp Med 184:931-943.

Igietseme, J. U., I. M. Uriri, R. Hawkins, and R. G. Rank. 1996. Integrin-mediated epithelial-T cell interaction enhances nitric oxide production and increased intracellular inhibition of Chlamydia. J Leukoc Biol 59:656-662.

Igietseme, J. U., P. B. Wyrick, D. Goyeau, and R. G. Rank. 1994. An in vitro model for immune control of chlamydial growth in polarized epithelial cells. Infect Immun 62:3528-3535.

Igietseme, J. U., K. H. Ramsey, D. M. Magee, D. M. Williams, T. J. Kincy, and R. G. Rank. 1993. Resolution of murine chlamydial genital infection by the adoptive transfer of a biovar-specific, Th1 lymphocyte clone. Reg Immunol 5:317-324.

Igietseme, J. U., I. M. Uriri, R. Hawkins, and R. G. Rank. 1996. Integrin-mediated epithelial-T cell interaction enhances nitric oxide production and increased intracellular inhibition of Chlamydia. J Leukoc Biol 59:656-662.

Igietseme, J. U., P. B. Wyrick, D. Goyeau, and R. G. Rank. 1994. An in vitro model for immune control of chlamydial growth in polarized epithelial cells. Infect Immun 62:3528-3535.

Igietseme, J. U. 1996. The molecular mechanism of T-cell control of Chlamydia in mice: role of nitric oxide. Immunology 87:1-8.

Igietseme, J. U. 1996. The molecular mechanism of T-cell control of Chlamydia in mice: role of nitric oxide. Immunology 87:1-8.

Igietseme, J. U., L. L. Perry, G. A. Ananaba, I. M. Uriri, O. O. Ojior, S. N. Kumar, and H. D. Caldwell. 1998. Chlamydial infection in inducible nitric oxide synthase knockout mice. Infect Immun 66:1282-1286.

Igietseme, J. U., I. M. Uriri, R. Hawkins, and R. G. Rank. 1996. Integrin-mediated epithelial-T cell interaction enhances nitric oxide production and increased intracellular inhibition of Chlamydia. J Leukoc Biol 59:656-662.

Igietseme, J. U., D. M. Magee, D. M. Williams, and R. G. Rank. 1994. Role for CD8+ T cells in antichlamydial immunity defined by Chlamydia-specific T-lymphocyte clones. Infect Immun 62:5195-5197.

Jayarapu, K., M. Kerr, S. Ofner, and R. M. Johnson. 2010. Chlamydia-Specific CD4 T Cell Clones Control Chlamydia muridarum Replication in Epithelial Cells by Nitroc Oxide Dependent and Independent Mechanisms. J. if Immunol 185: 6911-6920.

Jayarapu, K., M. S. Kerr, A. Katschke, and R. M. Johnson. 2009. Chlamydia muridarum-specific CD4 T-cell clones recognize infected reproductive tract epithelial cells in an interferon-dependent fashion. Infect Immun 77:4469-4479.

Jennings, S. R., R. H. Bonneau, P. M. Smith, R. M. Wolcott, and R. Chervenak. 1991. CD4-positive T lymphocytes are required for the generation of the primary but not the secondary CD8-positive cytolytic T lymphocyte response to herpes simplex virus in C57BL/6 mice. Cell Immunol 133: 234-252.

Joesoef, M. R., and D. J. Mosure. 2006. Prevalence of Chlamydia in young men in the United States from newly implemented universal screening in a national job training program. Sex Transm Dis 33:636-639.

Joesoef, M. R., and D. J. Mosure. 2006. Prevalence trends in chlamydial infections among young women entering the national job training program, 1998-2004. Sex Transm Dis 33:571-575.

Johnson, R. M. 2004. Murine oviduct epithelial cell cytokine responses to Chlamydia muridarum infection include interleukin-12-p70 secretion. Infect Immun 72:3951-3960.

Johnson, R. M. 2004. Murine oviduct epithelial cell cytokine responses to Chlamydia muridarum infection include interleukin-12-p70 secretion. Infect Immun 72:3951-3960.

Kiviat, N. B., P. Wolner-Hanssen, M. Peterson, J. Wasserheit, W. E. Stamm, D. A. Eschenbach, J. Paavonen, J. Lingenfelter, T. Bell, V. Zabriskie, and et al. 1986. Localization of Chlamydia trachomatis infection by direct immunofluorescence and culture in pelvic inflammatory disease. Am J Obstet Gynecol 154:865-873.

Kukel, S., U. Reinhold, I. Oltermann, and H. W. Kreysel. 1994. Progressive increase of CD7-T cells in human blood lymphocytes with ageing. Clin Exp Immunol 98:163-168.

Li, W., S. Kashiwamura, H. Ueda, A. Sekiyama, and H. Okamura. 2007. Protection of CD8+ T cells from activation-induced cell death by IL-18. J Leukoc Biol 82:142-151.

Low, N. 2004. Current status of chlamydia screening in Europe. Eurosurveillance Weekly 8.

Lu, H., C. Shen, and R. C. Brunham. 2000. Chlamydia trachomatis infection of epithelial cells induces the activation of caspase-1 and release of mature IL-18. J Immunol 165: 1463-1469.

Lu, H. T., J. L. Riley, G. T. Babcock, M. Huston, G. R. Stark, J. M. Boss, and R. M. Ransohoff. 1995. Interferon (IFN) beta acts downstream of IFN-gamma-induced class II transactivator messenger RNA accumulation to block major histocompatibility complex class II gene expression and requires the 48-kD DNA-binding protein, ISGF3-gamma. J Exp Med 182:1517-1525.

Mannon, R. B., C. Nataraj, B. L. Kotzin, R. Griffiths, S. Geier, S. Ibrahim, F. P. Sanfilippo, J. L. Platt, R. Kurlander, and T. M. Coffman. 1995. Rejection of kidney allografts by MHC class I-deficient mice. Transplantation 59:746-755.

Matloubian, M., R. J. Concepcion, and R. Ahmed. 1994. CD4+ T cells are required to sustain CD8+ cytotoxic T-cell responses during chronic viral infection. J Virol 68:8056-8063.

Matechak, E. O., N. Killeen, S. M. Hedrick, and B. J. Fowlkes. 1996. MHC class II-specific T cells can develop in the CD8 lineage when CD4 is absent. Immunity 4:337-347

Marelli-Berg, F. M., and R. I. Lechler. 1999. Antigen presentation by parenchymal cells: a route to peripheral tolerance? Immunol Rev 172:297-314.

Matyszak, M. K., and J. S. Gaston. 2004. Chlamydia trachomatis-specific human CD8+ T cells show two patterns of antigen recognition. Infect Immun 72:4357-4367.

McIntyre, K. R., and J. G. Seidman. 1984. Nucleotide sequence of mutant I-A beta bm12 gene is evidence for genetic exchange between mouse immune response genes. Nature 308:551-553.

Miller, R. A., and O. Stutman. 1982. Monoclonal antibody to Lyt 2 antigen blocks H-2I- and H-2K-specific mouse cytotoxic T cells. Nature 296:76-78.

Morrison, R. P., and H. D. Caldwell. 2002. Immunity to murine chlamydial genital infection. Infect Immun 70:2741-2751.

Morrison, R. P., K. Feilzer, and D. B. Tumas. 1995. Gene knockout mice establish a primary protective role for major histocompatibility complex class II-restricted responses in *Chlamydia trachomatis* genital tract infection. Infect Immun 63:4661-4668.

Morrison, S. G., and R. P. Morrison. 2005. A predominant role for antibody in acquired immunity to chlamydial genital tract reinfection. J Immunol 175:7536-7542.

Morrison, R. P., K. Feilzer, and D. B. Tumas. 1995. Gene knockout mice establish a primary protective role for major histocompatibility complex class II-restricted responses in *Chlamydia trachomatis* genital tract infection. Infect Immun 63:4661-4668.

Morrison, R. P., and H. D. Caldwell. 2002. Immunity to murine chlamydial genital infection. Infect Immun 70:2741-2751.

Murthy, A. K., J. P. Chambers, P. A. Meier, G. Zhong, and B. P. Arulanandam. 2007. Intranasal vaccination with a secreted chlamydial protein enhances resolution of genital *Chlamydia muridarum* infection, protects against oviduct pathology, and is highly dependent upon endogenous gamma interferon production. Infect Immun 75:666-676.

Nagarajan, U. M., D. Prantner, J. D. Sikes, C. W. Andrews, Jr., A. M. Goodwin, S. Nagarajan, and T. Darville. 2008. Type I interferon signaling exacerbates *Chlamydia muridarum* genital infection in a murine model. Infect Immun 76:4642-4648.

Nakayama, E. 1982. Blocking of effector cell cytotoxicity and T-cell proliferation by Lyt antisera. Immunol Rev 68:117-134.

Nakhleh, R. E., D. C. Snover, S. Weisdorf, and J. L. Platt. 1989. Immunopathology of graft-versus-host disease in the upper gastrointestinal tract. Transplantation 48:61-65.

Nelson, D. E., D. P. Virok, H. Wood, C. Roshick, R. M. Johnson, W. M. Whitmire, D. D. Crane, O. Steele-Mortimer, L. Kari, G. McClarty, and H. D. Caldwell. 2005. Chlamydial IFN-{gamma} immune evasion is linked to host infection tropism. Proc Natl Acad Sci USA 102:10658-10663.

Nelson, D. E., D. P. Virok, H. Wood, C. Roshick, R. M. Johnson, W. M. Whitmire, D. D. Crane, O. Steele-Mortimer, L. Kari, G. McClarty, and H. D. Caldwell. 2005. Chlamydial IFN-{gamma} immune evasion is linked to host infection tropism. Proc Natl Acad Sci USA 102:10658-10663.

Nelson, D. E., D. P. Virok, H. Wood, C. Roshick, R. M. Johnson, W. M. Whitmire, D. D. Crane, O. Steele-Mortimer, L. Kari, G. McClarty, and H. D. Caldwell. 2005. Chlamydial IFN-{gamma} immune evasion is linked to host infection tropism. Proc Natl Acad Sci USA 102:10658-10663.

Olson, M. R., and S. M. Varga. 2007. CD8 T cells inhibit respiratory syncytial virus (RSV) vaccine-enhanced disease. J Immunol 179:5415-5424.

Pal, S., T. J. Fielder, E. M. Peterson, and L. M. de la Maza. 1994. Protection against infertility in a BALB/c mouse salpingitis model by intranasal immunization with the mouse pneumonitis biovar of *Chlamydia trachomatis*. Infect Immun 62:3354-3362.

Perry, L. L., K. Feilzer, and H. D. Caldwell. 1997. Immunity to *Chlamydia trachomatis* is mediated by T helper 1 cells through IFN-gamma-dependent and -independent pathways. J Immunol 158:3344-3352.

Perry, L. L., K. Feilzer, S. Hughes, and H. D. Caldwell. 1999. Clearance of *Chlamydia trachomatis* from the murine genital mucosa does not require perforin-mediated cytolysis or Fas-mediated apoptosis. Infect Immun 67:1379-1385

Pierres, A., P. Naquet, A. Van Agthoven, F. Bekkhoucha, F. Denizot, Z. Mishal, A. M. Schmitt-Verhulst, and M. Pierres. 1984. A rat anti-mouse T4 monoclonal antibody (H129.19) inhibits the proliferation of Ia-reactive T cell clones and delineates two phenotypically distinct (T4+, Lyt-2,3−, and T4−, Lyt-2,3+) subsets among anti-Ia cytolytic T cell clones. J Immunol 132:2775-2782.

Prabhala, R. H., and C. R. Wira. 1995. Sex hormone and IL-6 regulation of antigen presentation in the female reproductive tract mucosal tissues. J Immunol 155:5566-5573.

Prevention, C. f. D. C. a. 2007. Sexually Transmitted Disease Surveillance 2007 Supplement, *Chlamydia* Prevalence Monitoring Project Annual Report 2007.

Regnault, A., D. Lankar, V. Lacabanne, A. Rodriguez, C. Thery, M. Rescigno, T. Saito, S. Verbeek, C. Bonnerot, P. Ricciardi-Castagnoli, and S. Amigorena. 1999. Fcgamma receptor-mediated induction of dendritic cell maturation and major histocompatibility complex class I-restricted antigen presentation after immune complex internalization. J Exp Med 189:371-380.

Rahemtulla, A., T. M. Kundig, A. Narendran, M. F. Bachmann, M. Julius, C. J. Paige, P. S. Ohashi, R. M. Zinkernagel, and T. W. Mak. 1994. Class II major histocompatibility complex-restricted T cell function in CD4-deficient mice. Eur J Immunol 24:2213-2218.

Ramsey, K. H., G. S. Miranpuri, C. E. Poulsen, N. B. Marthakis, L. M. Braune, and G. I. Byrne. 1998. Inducible nitric oxide synthase does not affect resolution of murine chlamydial genital tract infections or eradication of chlamydiae in primary murine cell culture. Infect Immun 66:835-838.

Rappl, G., H. Abken, D. O. Hasselmann, W. Tilgen, S. Ugurel, and U. Reinhold. 2001. The CD7(−) subset of CD4(+) memory T cells is prone to accelerated apoptosis that is prevented by interleukin-15 (IL-15). Cell Death Differ 8:395-402.

Reinhold, U., H. Abken, S. Kukel, M. Moll, R. Muller, I. Oltermann, and H. W. Kreysel. 1993. CD7− T cells represent a subset of normal human blood lymphocytes. J Immunol 150:2081-2089.

Riberdy, J. M., J. P. Christensen, K. Branum, and P. C. Doherty. 2000. Diminished primary and secondary influenza virus-specific CD8(+) T-cell responses in CD4-depleted Ig(−/−) mice. J Virol 74:9762-9765.

Richards, D. M., S. L. Dalheimer, M. I. Hertz, and D. L. Mueller. 2003. Trachea allograft class I molecules directly activate and retain CD8+ T cells that cause obliterative airways disease. J Immunol 171:6919-6928.

Roan, N. R., and M. N. Starnbach. 2008. Immune-mediated control of *Chlamydia* infection. Cell Microbiol 10:9-19.

Rock, K. L., B. Benacerraf, and A. K. Abbas. 1984. Antigen presentation by hapten-specific B lymphocytes. I. Role of surface immunoglobulin receptors. J Exp Med 160:1102-1113.

Roshick, C., H. Wood, H. D. Caldwell, and G. McClarty. 2006. Comparison of gamma interferon-mediated antichlamydial defense mechanisms in human and mouse cells. Infect Immun 74:225-238.

Roshick, C., H. Wood, H. D. Caldwell, and G. McClarty. 2006. Comparison of gamma interferon-mediated antichlamydial defense mechanisms in human and mouse cells. Infect Immun 74:225-238.

San-Antonio, B., M. A. Iniguez, and M. Fresno. 2002. Protein kinase Czeta phosphorylates nuclear factor of activated T cells and regulates its transactivating activity. J Biol Chem 277:27073-27080.

Sempowski, G. D., D. M. Lee, R. M. Scearce, D. D. Patel, and B. F. Haynes. 1999. Resistance of CD7-deficient mice to lipopolysaccharide-induced shock syndromes. J Exp Med 189:1011-1016.

Shaw, J. H., V. R. Grund, L. Durling, and H. D. Caldwell. 2001. Expression of genes encoding Th1 cell-activating cytokines and lymphoid homing chemokines by *chlamydia*-pulsed dendritic cells correlates with protective immunizing efficacy. Infect Immun 69:4667-4672.

Shedlock, D. J., and H. Shen. 2003. Requirement for CD4 T cell help in generating functional CD8 T cell memory. Science 300:337-339.

Shinohara, N., N. Hozumi, M. Watanabe, J. A. Bluestone, R. Johnson-Leva, and D. H. Sachs. 1988. Class II antigen-specific murine cytolytic T lymphocytes (CTL). II. Genuine class II specificity of Lyt-2+ CTL clones. J Immunol 140:30-36.

Shinohara, N. 1987. Class II antigen-specific murine cytolytic T lymphocytes (CTL). I. Analysis of bulk populations and establishment of Lyt-2+L3T4- and Lyt-2-L3T4+ bulk CTL lines. Cell Immunol 107:395-407

Sprent, J., M. Schaefer, D. Lo, and R. Korngold. 1986. Properties of purified T cell subsets. II. In vivo responses to class I vs. class II H-2 differences. J Exp Med 163:998-1011.

Staats, H. F., C. P. Bradney, W. M. Gwinn, S. S. Jackson, G. D. Sempowski, H. X. Liao, N. L. Letvin, and B. F. Haynes. 2001. Cytokine requirements for induction of systemic and mucosal CTL after nasal immunization. J Immunol 167:5386-5394.

Steele, L. N., Z. R. Balsara, and M. N. Starnbach. 2004. Hematopoietic cells are required to initiate a *Chlamydia trachomatis*-specific CD8+ T cell response. J Immunol 173:6327-6337.

Su, H., and H. D. Caldwell. 1995. Kinetics of chlamydial antigen processing and presentation to T cells by paraformaldehyde-fixed murine bone marrow-derived macrophages. Infect Immun 63:946-953.

Su, H., R. Morrison, R. Messer, W. Whitmire, S. Hughes, and H. D. Caldwell. 1999. The effect of doxycycline treatment on the development of protective immunity in a murine model of chlamydial genital infection. J Infect Dis 180:1252-1258.

Sun, J. C., and M. J. Bevan. 2003. Defective CD8 T cell memory following acute infection without CD4 T cell help. Science 300:339-342.

Swanson, J., D. A. Eschenbach, E. R. Alexander, and K. K. Holmes. 1975. Light and electron microscopic study of *Chlamydia trachomatis* infection of the uterine cervix. J Infect Dis 131:678-687.

Trautmann, A., B. Ruckert, P. Schmid-Grendelmeier, E. Niederer, E. B. Brocker, K. Blaser, and C. A. Akdis. 2003. Human CD8 T cells of the peripheral blood contain a low CD8 expressing cytotoxic/effector subpopulation. Immunology 108:305-312.

Varga, S. M., X. Wang, R. M. Welsh, and T. J. Braciale. 2001. Immunopathology in RSV infection is mediated by a discrete oligoclonal subset of antigen-specific CD4(+) T cells. Immunity 15:637-646.

Vallera, D. A., P. A. Taylor, J. Sprent, and B. R. Blazar. 1994. The role of host T cell subsets in bone marrow rejection directed to isolated major histocompatibility complex class I versus class II differences of bm1 and bm12 mutant mice. Transplantation 57:249-256.

Vidovic, D., A. Juretic, Z. A. Nagy, and J. Klein. 1981. Lyt phenotypes of primary cytotoxic T cells generated across the A and E region of the H-2 complex. Eur J Immunol 11:499-504.

Wang, S. P., J. T. Grayston, and E. R. Alexander. 1967. Trachoma vaccine studies in monkeys. Am J Ophthalmol 63:Supp1:1615-1630.

Wira, C. R., R. M. Rossoll, and R. C. Young. 2005. Polarized Uterine Epithelial Cells Preferentially Present Antigen at the Basolateral Surface: Role of Stromal Cells in Regulating Class II-Mediated Epithelial Cell Antigen Presentation. J Immunol 175:1795-1804.

Zhong, G., T. Fan, and L. Liu. 1999. *Chlamydia* inhibits interferon gamma-inducible major histocompatibility complex class II expression by degradation of upstream stimulatory factor 1. J Exp Med 189:1931-1938.

---

I claim:

1. A method of identifying an agent that elicits an immune response in the epithelial tissue of a mammal, comprising the steps of:
    culturing epithelial cells under a condition in which the epithelial cells do not exhibit interferon gamma inducible nitric oxide synthetase (iNOS) activity;
    exposing a sample of epithelial tissue from the mammal said epithelial cells to an agent;
    co-culturing said exposed epithelial cells with CD8zeta cells or CD4 T-cells;
    performing at least one of the following assays on the CD8zeta cell or the CD4 T-cell selected from the group consisting of:
    flow cytometry to identify at least one of the following cell types, CD4 T-cells or CD8zeta cells that express Casd1 and Plac8;
    mRNA hybridization that is indicative of messenger RNA encoding at least one of the following polypeptides SEQ ID NO. 1, SEQ ID NO. 2, SEQ ID NO. 3, SEQ ID NO. 4, SEQ ID NO. 5, SEQ ID NO. 6;
    micro array that binds to at least one polynucleotide that encodes information of the translation of one of the following polypeptides SEQ ID NO. 1, SEQ ID NO. 2, SEQ ID NO. 3, SEQ ID NO. 4, SEQ ID NO. 5, SEQ ID NO. 6; and
    Western blotting that preferentially detects at least one of the following polypeptides SEQ ID NO. 1, SEQ ID NO. 2, SEQ ID NO. 3, SEQ ID NO. 4, SEQ ID NO. 5, SEQ ID NO. 6; and
detecting the presence of CD8zeta cells or CD4 T-cells, wherein said cells express Casd1 and/or Plac8.

2. The method according to claim 1, wherein identifying Casd1 is dependent upon the expression of at least one polypeptide selected from the group consisting of: SEQ ID NO. 1, SEQ ID NO. 2, SEQ ID NO. 3, SEQ ID NO. 4, SEQ ID NO. 5, SEQ ID NO. 6.

3. The method according to claim 1, wherein the identifying step further comprises identifying a gene expressed in the CD4 T-cells that has at least 80 percent homology to Casd1 or to Plac8.

4. The method according to claim 1, wherein the mammal is a human.

5. The method according to claim 1, wherein the mammal is a transgenic mouse.

6. The method according to claim 5, wherein the epithelial tissue of the transgenic mouse is genetically altered such that the cells in its epithelial tissue do not exhibit iNOS activity while cells in other portions of its body may exhibit iNOS activity.

7. The method according to claim 1, wherein the agent that elicits an immune response is at least one microorganism that infects mammalian epithelial cells.

8. The method according to claim 7, wherein the microorganism is an infectious strain of *Chlamydia*.

9. The method according to claim 8, wherein the strain of *Chlamydia* is selected from the group consisting of *C. muridarum* and *C. trachomatis*.

10. A kit for identifying an agent that elicits an immune response in mammalian epithelial tissue, comprising:
    at least one reagent that preferentially interacts with CD8zeta cells or a subset of CD4 T-cells that express Casd1 and/or Plac8 genes, which are found in the epithelial tissue of mammals;
    at least one iNOS inhibitor; and
    at least one purified interferon gamma from mouse or human.

11. The kit according to claim 10, wherein the reagent is an antibody that binds to at least one amino acid sequence selected from the group consisting of: SEQ ID NO. 1, SEQ ID NO. 2, SEQ ID NO. 3, SEQ ID NO. 4, SEQ ID NO. 5, SEQ ID NO. 6.

12. The kit according to claim 11, wherein the antibody binds to an amino acid sequence that has at least 95 percent homology to at least one amino acid sequence selected from the group consisting of SEQ ID NO. 1, SEQ ID NO. 2, SEQ ID NO. 3, SEQ ID NO. 4, SEQ ID NO. 5, SEQ ID NO. 6.

13. The kit according to claim 11, wherein the antibody binds to an amino acid sequence that has at least 90 percent identity to at least one amino acid sequence selected from the group consisting of SEQ ID NO. 1, SEQ ID NO. 2, SEQ ID NO. 3, SEQ ID NO. 4, SEQ ID NO. 5, SEQ ID NO. 6.

14. The kit according to claim 11, wherein the antibody binds to an amino acid sequence that has at least 95 percent identity to at least one amino acid sequence selected from the group consisting of SEQ ID NO. 1, SEQ ID NO. 2, SEQ ID NO. 3, SEQ ID NO. 4, SEQ ID NO. 5, SEQ ID NO. 6.

15. The kit according to claim 10, wherein the reagent is a portion of a nucleic acid that hybridizes to a portion of the mRNA produced by the expression of at least one of the following genes Casd1 or Plac8.

16. The kit according to claim 10, wherein the immune response is caused by an antigen that elicits an epithelial tissue based response, wherein the antigen is a microbial infection of mammalian epithelial tissue.

17. The kit according to claim 16, wherein the microbial infection is caused by a strain of *Chlamydia*.

18. The kit according to claim 17, wherein the strain of *Chlamydia* is selected from the group consisting of *C. muridarum* and *C. trachomatis*.

19. The method according to claim 1, the culturing step further comprises treating said epithelial cells with interferon-gamma (IFN-g).

20. The method according to claim 1, the culturing step further comprises treating said epithelial cells with iNOS inhibitor.

21. The method according to claim 1, wherein the exposing step continues for at least 12 hours.

22. The method according to claim 1, wherein said epithelial cells are derived from the group consisting of human and mouse.

23. The method according to claim 1, wherein said epithelial cells are murine epithelial cells.

* * * * *